(12) United States Patent
Embers et al.

(10) Patent No.: US 12,638,446 B2
(45) Date of Patent: May 26, 2026

(54) MULTI-ANTIGEN DIAGNOSTIC FOR DETECTING LYME DISEASE

(71) Applicants: Focus on Lyme Foundation, Paradise Valley, AZ (US); The Administrators of The Tulane Educational Fund, New Orleans, LA (US)

(72) Inventors: Monica Embers, New Orleans, LA (US); Tammy Crawford, Paradise Valley, AZ (US); Holly Ahern, Charlton, NY (US)

(73) Assignees: Focus on Lyme Foundation, Paradise Valley, AZ (US); The Administrators of The Tulane Educational Fund, New Orleans, LA (US)

( * ) Notice: Subject to any disclaimer, the term of this patent is extended or adjusted under 35 U.S.C. 154(b) by 0 days.

(21) Appl. No.: 18/814,445

(22) Filed: Aug. 23, 2024

(65) Prior Publication Data

US 2025/0067736 A1     Feb. 27, 2025

Related U.S. Application Data

(60) Provisional application No. 63/534,783, filed on Aug. 25, 2023.

(51) Int. Cl.
*G01N 33/569*     (2006.01)
(52) U.S. Cl.
CPC .............................. *G01N 33/56911* (2013.01)
(58) Field of Classification Search
CPC ......... G01N 33/56911; G01N 33/6854; G01N 33/563; G01N 33/48; G01N 33/53; G01N 33/569; G01N 2333/20; C07K 14/20; C07K 2319/00; C07K 2319/40; Y02A 50/30; A61K 39/00; A61K 39/0225; A61K 38/00; A61K 2039/54
See application file for complete search history.

(56) References Cited

U.S. PATENT DOCUMENTS

| | | | |
|---|---|---|---|
| 4,888,276 | A | 12/1989 | Shelburne |
| 5,155,022 | A | 10/1992 | Naqui et al. |
| 5,187,065 | A | 2/1993 | Schutzer |
| 5,217,872 | A | 6/1993 | Dorward et al. |
| 5,246,844 | A | 9/1993 | Norris et al. |
| 5,264,342 | A | 11/1993 | Osther et al. |

(Continued)

FOREIGN PATENT DOCUMENTS

| | | |
|---|---|---|
| WO | 1997042221 | 11/1997 |
| WO | 2000065064 | 11/2000 |

(Continued)

OTHER PUBLICATIONS

Embers et al., (ASM Journals. Clinical and Vaccine Immunology. vol. 23, No. 4). (Year: 2016).*

(Continued)

*Primary Examiner* — Jana A Hines
(74) *Attorney, Agent, or Firm* — Snell & Wilmer, L.L.P.

(57) ABSTRACT

This application relates to methods of diagnosing Lyme disease. In some embodiments, the methods include detecting levels of at least one antigen in a sample. In some embodiments, the methods include a combination of detecting levels of at least one antigen in a sample and classifying samples using one or more decision trees.

6 Claims, 31 Drawing Sheets

Non-Normalized Controls From IgG Plates by Antigen

Control Sample Labels

(56) References Cited

U.S. PATENT DOCUMENTS

| | | | |
|---|---|---|---|
| 5,308,753 | A | 5/1994 | Dorward et al. |
| 5,324,630 | A | 6/1994 | LeFebvre et al. |
| 5,403,718 | A | 4/1995 | Dorward et al. |
| 5,470,712 | A | 11/1995 | Simpson et al. |
| 5,478,753 | A | 12/1995 | Wong et al. |
| 5,523,089 | A | 6/1996 | Bergstrom et al. |
| 5,585,102 | A | 12/1996 | Barbour et al. |
| 5,618,533 | A | 4/1997 | Flavell et al. |
| 5,620,862 | A | 4/1997 | Padula |
| 5,643,733 | A | 7/1997 | Robinson et al. |
| 5,643,751 | A | 7/1997 | Robinson et al. |
| 5,747,294 | A | 5/1998 | Flavell et al. |
| 5,807,685 | A | 9/1998 | Flavell et al. |
| 5,965,702 | A | 10/1999 | Robinson et al. |
| 5,977,339 | A | 11/1999 | LeFebvre et al. |
| 5,985,595 | A | 11/1999 | Krider |
| 6,013,460 | A | 1/2000 | Levin |
| 6,045,804 | A | 4/2000 | Persing |
| 6,143,872 | A | 11/2000 | Barbour et al. |
| 6,165,736 | A | 12/2000 | Fawcett |
| 6,183,755 | B1 | 2/2001 | Motz et al. |
| 6,197,301 | B1 | 3/2001 | Flavell et al. |
| 6,210,676 | B1 | 4/2001 | Callister et al. |
| 6,248,538 | B1 | 6/2001 | Motz et al. |
| 6,300,101 | B1 | 10/2001 | Sadziene et al. |
| 6,437,116 | B1 | 8/2002 | Norris et al. |
| 6,464,985 | B1 | 10/2002 | Callister et al. |
| 6,475,492 | B1 | 11/2002 | Philipp et al. |
| 6,509,019 | B1 | 1/2003 | Fuchs et al. |
| 6,610,301 | B1 | 8/2003 | Motz et al. |
| 6,610,838 | B1 | 8/2003 | Bergstrom |
| 6,660,274 | B2 | 12/2003 | Philipp |
| 6,665,652 | B1 | 12/2003 | Porwancher |
| 6,716,591 | B1 | 4/2004 | Flavell et al. |
| 6,740,744 | B2 | 5/2004 | Norris et al. |
| 6,753,183 | B2 | 6/2004 | Fuchs et al. |
| 6,838,247 | B2 | 1/2005 | Whitaker et al. |
| 7,045,134 | B2 | 5/2006 | Qiu et al. |
| 7,083,792 | B2 | 8/2006 | Fuchs et al. |
| 7,105,311 | B2 | 9/2006 | Kovalenko |
| 7,125,517 | B2 | 10/2006 | Kovalenko |
| 7,135,176 | B2 | 11/2006 | Norris et al. |
| 7,390,626 | B2 | 6/2008 | Vojdani |
| 7,582,304 | B2 | 9/2009 | Dattwyler et al. |
| 7,785,597 | B2 | 8/2010 | Norris et al. |
| 7,847,084 | B2 | 12/2010 | Norris |
| 7,887,815 | B2 | 2/2011 | Dattwyler et al. |
| 8,005,627 | B2 | 8/2011 | Porwancher |
| 8,071,109 | B2 | 12/2011 | Norris et al. |
| 8,076,470 | B2 | 12/2011 | Norris |
| 8,129,165 | B2 | 3/2012 | Lundberg et al. |
| 8,163,500 | B2 | 4/2012 | Komorowski et al. |
| 8,247,181 | B2 | 8/2012 | Barbour et al. |
| 8,338,566 | B2 | 12/2012 | Pal et al. |
| 8,354,240 | B2 | 1/2013 | Norris et al. |
| 8,431,135 | B2 | 4/2013 | Komorowski et al. |
| 8,568,989 | B2 | 10/2013 | Mehra et al. |
| 8,694,265 | B2 | 4/2014 | Porwancher |
| 8,758,772 | B2 | 6/2014 | Mehra et al. |
| 8,895,257 | B2 | 11/2014 | Levet et al. |
| 8,946,393 | B2 | 2/2015 | Wagner |
| 9,115,193 | B2 | 8/2015 | Norris |
| 9,182,412 | B2 | 11/2015 | Barbour et al. |
| 9,194,870 | B2 | 11/2015 | Mehra et al. |
| 9,201,071 | B2 | 12/2015 | Mehra et al. |
| 9,207,233 | B2 | 12/2015 | Schollhorn |
| 9,212,218 | B2 | 12/2015 | Norris et al. |
| 9,310,367 | B2 | 4/2016 | Burbelo et al. |
| 9,316,652 | B2 | 4/2016 | Joosten et al. |
| 9,347,943 | B2 | 5/2016 | Levet et al. |
| 9,395,365 | B2 | 7/2016 | Levine et al. |
| 9,500,648 | B1 | 11/2016 | Tate, Jr. |
| 9,534,021 | B2 | 1/2017 | Earnhart et al. |
| 9,670,254 | B2 | 6/2017 | Norris |
| 9,733,246 | B2 | 8/2017 | Deml et al. |
| 9,766,238 | B2 | 9/2017 | Mehra et al. |
| 9,816,991 | B2 | 11/2017 | Dattwyler et al. |
| 9,977,020 | B2 | 5/2018 | Levet et al. |
| 10,006,912 | B2 | 6/2018 | Dattwyler et al. |
| 10,073,095 | B2 | 9/2018 | Mehra et al. |
| 10,086,057 | B2 | 10/2018 | Marconi et al. |
| 10,100,092 | B2 | 10/2018 | Atkinson et al. |
| 10,287,636 | B2 | 5/2019 | Hillebrand et al. |
| 10,288,608 | B2 | 5/2019 | Kozlov et al. |
| 10,294,531 | B2 | 5/2019 | Jewett et al. |
| 10,323,070 | B2 | 6/2019 | Norris |
| 10,336,808 | B2 | 7/2019 | Schøller et al. |
| 10,386,373 | B2 | 8/2019 | Daugherty et al. |
| 10,401,358 | B1 | 9/2019 | Bradshaw et al. |
| 10,457,721 | B2 | 10/2019 | Wang et al. |
| 10,466,240 | B2 | 11/2019 | Marconi et al. |
| 10,718,767 | B2 | 7/2020 | Shah et al. |
| 10,802,022 | B1 | 10/2020 | Bradshaw et al. |
| 10,921,321 | B2 | 2/2021 | Mehra et al. |
| 10,928,394 | B2 | 2/2021 | Kage |
| 10,968,269 | B2 | 4/2021 | Schøller et al. |
| 10,983,121 | B2 | 4/2021 | Callister et al. |
| 11,061,028 | B2 | 7/2021 | Lukinova et al. |
| 11,131,670 | B2 | 9/2021 | Reed et al. |
| 11,209,431 | B2 | 12/2021 | Delanoy et al. |
| 11,300,519 | B2 | 4/2022 | Tabb et al. |
| 11,320,423 | B2 | 5/2022 | Upmeier et al. |
| 11,353,455 | B2 | 6/2022 | Gilbert et al. |
| 11,353,457 | B2 | 6/2022 | Shah et al. |
| 11,360,086 | B2 | 6/2022 | Johnston et al. |
| 11,548,938 | B2 | 1/2023 | Sun et al. |
| 11,573,227 | B2 | 2/2023 | Mehra et al. |
| 2001/0046499 | A1 | 11/2001 | Kantor et al. |
| 2002/0106706 | A1 | 8/2002 | Qiu et al. |
| 2003/0134345 | A1 | 7/2003 | Brunner |
| 2003/0138868 | A1 | 7/2003 | Jungblut et al. |
| 2004/0067517 | A1 | 4/2004 | Philipp |
| 2005/0233394 | A1 | 10/2005 | Raoult |
| 2006/0034862 | A1 | 2/2006 | Lahdenne et al. |
| 2006/0281139 | A1 | 12/2006 | Kintrup et al. |
| 2009/0196852 | A1 | 8/2009 | Watkinson |
| 2010/0159488 | A1 | 6/2010 | Drancourt et al. |
| 2010/0278752 | A1 | 11/2010 | Kotsyfakis et al. |
| 2010/0292096 | A1 | 11/2010 | Luft et al. |
| 2011/0105355 | A1 | 5/2011 | Luft et al. |
| 2012/0142023 | A1 | 6/2012 | Ascoli et al. |
| 2012/0201746 | A1 | 8/2012 | Liu et al. |
| 2012/0208176 | A1 | 8/2012 | Bedouelle et al. |
| 2013/0085076 | A1 | 4/2013 | Douglas et al. |
| 2014/0228455 | A1 | 8/2014 | Nilsson et al. |
| 2014/0274925 | A1 | 9/2014 | Jin et al. |
| 2014/0308677 | A1 | 10/2014 | Ascoli et al. |
| 2015/0219646 | A1 | 8/2015 | Branda et al. |
| 2015/0241426 | A1 | 8/2015 | Kaldjian et al. |
| 2015/0285798 | A1 | 10/2015 | Jin et al. |
| 2016/0097768 | A1 | 4/2016 | Marconi et al. |
| 2016/0195527 | A1 | 7/2016 | Barbour et al. |
| 2016/0237478 | A1* | 8/2016 | Jewett ................... C07K 14/20 |
| 2016/0266112 | A1 | 9/2016 | Norris et al. |
| 2017/0212114 | A1 | 7/2017 | Luft et al. |
| 2017/0218091 | A1 | 8/2017 | Ambrosi |
| 2018/0238874 | A1 | 8/2018 | Levet et al. |
| 2018/0238902 | A1 | 8/2018 | Bhatt et al. |
| 2018/0246095 | A1 | 8/2018 | Zhang et al. |
| 2019/0276877 | A1 | 9/2019 | Clokie et al. |
| 2020/0200745 | A1 | 6/2020 | Mehra et al. |
| 2020/0255889 | A1 | 8/2020 | Tokarz et al. |
| 2020/0347114 | A1 | 11/2020 | Schøller et al. |
| 2021/0047383 | A1 | 2/2021 | Schøller et al. |
| 2021/0068697 | A1 | 3/2021 | Baig et al. |
| 2021/0072257 | A1 | 3/2021 | Lee et al. |
| 2021/0079048 | A1 | 3/2021 | Norris |
| 2021/0156858 | A1 | 5/2021 | Kage |
| 2021/0188971 | A1 | 6/2021 | Sun et al. |
| 2021/0215715 | A1 | 7/2021 | Chang et al. |
| 2021/0325393 | A1 | 10/2021 | Shah et al. |
| 2021/0364514 | A1 | 11/2021 | Jutras et al. |
| 2021/0382052 | A1 | 12/2021 | Joung et al. |
| 2021/0396752 | A1 | 12/2021 | Reed et al. |

(56)　　　　References Cited

U.S. PATENT DOCUMENTS

| | | | |
|---|---|---|---|
| 2022/0034880 | A1 | 2/2022 | Weissman et al. |
| 2022/0057397 | A1 | 2/2022 | Callister et al. |
| 2022/0064226 | A1 | 3/2022 | Brix et al. |
| 2022/0137047 | A1 | 5/2022 | Delanoy et al. |
| 2022/0160856 | A1 | 5/2022 | Thomas |
| 2022/0170066 | A1 | 6/2022 | Belisle et al. |
| 2022/0220546 | A1 | 7/2022 | Sabeti et al. |
| 2022/0229055 | A1 | 7/2022 | Shah et al. |
| 2022/0244251 | A1 | 8/2022 | Aucoin et al. |
| 2022/0268771 | A1 | 8/2022 | Zhang |
| 2022/0298572 | A1 | 9/2022 | Wallace et al. |
| 2022/0325324 | A1 | 10/2022 | Driebe et al. |
| 2023/0063066 | A1 | 3/2023 | Wang et al. |

FOREIGN PATENT DOCUMENTS

| | | |
|---|---|---|
| WO | 2001042790 | 6/2001 |
| WO | 2002016422 | 10/2002 |
| WO | 2006024466 | 3/2006 |
| WO | 2006093651 | 2/2007 |
| WO | 2007065098 | 6/2007 |
| WO | 2008031082 | 12/2008 |
| WO | 2009004056 | 1/2009 |
| WO | 2009033163 | 3/2009 |
| WO | 2009131665 | 10/2009 |
| WO | 2009106073 | 5/2010 |
| WO | 2011023909 | 3/2011 |
| WO | 2011023914 | 3/2011 |
| WO | 2010132758 | 4/2011 |
| WO | 2011063003 | 9/2011 |
| WO | 2011112805 | 9/2011 |
| WO | 2011163258 | 12/2011 |
| WO | 2012039614 | 3/2012 |
| WO | 2011117844 | 7/2012 |
| WO | 2012047607 | 8/2012 |
| WO | 2012054580 | 8/2012 |
| WO | 2013036187 | 4/2013 |
| WO | 2013067524 | 5/2013 |
| WO | 2013110026 | 7/2013 |
| WO | 2013116668 | 10/2014 |
| WO | 2014122467 | 10/2014 |
| WO | 2014185803 | 11/2014 |
| WO | 2015054319 | 6/2015 |
| WO | 2015085323 | 6/2015 |
| WO | 2016057562 | 4/2016 |
| WO | 2016057793 | 4/2016 |
| WO | 2017031216 | 2/2017 |
| WO | 2017053167 | 3/2017 |
| WO | 2017062535 | 5/2017 |
| WO | 2018083491 | 5/2018 |
| WO | 2019053175 | 3/2019 |
| WO | 2019060885 | 3/2019 |
| WO | 2019173569 | 9/2019 |
| WO | 2020127222 | 7/2020 |
| WO | 2020163568 | 8/2020 |
| WO | 2020186223 | 9/2020 |
| WO | 2020243159 | 5/2021 |
| WO | 2021127547 | 6/2021 |
| WO | 2021142294 | 7/2021 |
| WO | 2021211637 | 10/2021 |
| WO | 2022155279 | 7/2022 |
| WO | 2022169876 | 8/2022 |
| WO | 2022197351 | 9/2022 |
| WO | 2023069725 | 4/2023 |
| WO | 2023086901 | 5/2023 |

OTHER PUBLICATIONS

Wagner et al., (Clin Vaccine Immunol. Apr. 2012; 19(4):527-35.). (Year: 2012).*
Nouri et al (Infection, Genetics & Evolution. vol. 91, Jul. 2021:104793). Availble online Feb. 27, 2021. (Year: 2021).*
Nouri et al., (Infection, Genetics and Evolution, vol. 91, Jul. 2021, 104793). (Year: 2021).*
Wormser et al., (Diagn Microbiol Infect Dis. Oct. 11, 2012;75(1):9-15). (Year: 2012).*
Adams, W., et al. "Lyme with a side- or two- of Babesia: The most common co-infection that is frequently missed" Bay Area Lyme Foundation, pp. 1-7 (2021).
Adkison, H., et al. "Lyme disease and the pursuit of a clinical cure" Frontiers in Medicine, pp. 1-14 (2023).
Advances in Lyme Disease (2016).
Alruwaili, Y., et al. "Superior efficacy of combination antibiotic therapy versus monotherapy on a mouse model of Lyme disease" Frontiers in Microbiology, pp. 1-13 (2023).
Arumugam, S., et al. "A Multiplexed Serologic Test for Diagnosis of Lyme Disease for Point-of-Care Use" Journal of Clinical Microbiology, 57(12) pp. 1-12 (2019).
Blum et al. "Robust B Cell Responses Predict Rapid Resolution of Lyme Disease" Frontiers in Microbiology, 9 (1634) pp. 1-13 (2018).
Bobe, J., et al. ":Recent Progress in Lyme Disease and Remaining Challenges" Frontiers in Medicine, 8 (666554) pp. 1-25 (2021).
Brandt, K. S., et al. "Evaluation of Patient IgM and IgG Reactivity Against Multiple Antigens for Improvement of Serodiagnostic Testing for Early Lyme Disease" Frontiers in Public Health, 7(370) pp. 1-7 (2019).
Brandt, K. S., et al. "Evaluation of in vivo expressed Borrelia burgdorferi antigens for improved IgM serodiagnosis of early Lyme disease" Diagnostic Microbiology and Infectious Disease 93, pp. 196-202 (2019).
Bransfield, R., et al. "Late-stage borreliosis and substance abuse" Heliyon, 10, pp. 1-12 (2024).
Cabello, F., et al. "Reply to Luger, Why Is It So Hard to Find Persistent Borreliella burgdorferi?" American Society for Microbiology, 13 (5), pp. 1-2 (2022).
Cabello, F., et al. "Borreliella burgdorferi Antimicrobial-Tolerant Persistence in Lyme Disease and Posttreatment Lyme Disease Syndromes" American Society of Microbiology, 13 (3), pp. 1-19 (2022).
Carlson, D., et al. "Targeting Borrelia burgorferi HtpG with a berserker molecule, a strategy for anti-microbial development" Cell Chemical Biology, 31 pp. 465-476.31-e12 (2024).
Caskey, J., et al. "Persister Development by Borrelia burgdorferi Populations In Vitro" Antimicrobial Agents and Chemotherapy, 59 (10) pp. 6288-6295 (2015).
Caskey, J., et al. "The Functional and Molecular Effects of Doxycycline Treatment on Borrelia burgdorferi Phenotype" Frontiers in Microbiology, 10 (690) pp. 1-11 (2019).
Crossland, N., et al. "Late Disseminated Lyme Disease Associated Pathology and Spirochete Persistence Posttreatment in Rhesus Macaques" The American Journal of Pathology, 188 (3) pp. 672-682 (2018).
Curtis, M., et al. "Characterization of Immunological Responses to Borrelia Immunogenic Protein A (BipA), a Species-Specific Antigen for North American Tick-Borne Relapsing Fever," American Society of Microbiology, Microbiology Spectrum, 10 (3) pp. 1-14 (2022).
Donta, S., et al. "Report of the Pathogenesis and Pathophysiology of Lyme Disease Subcommittee of the HHS Tick Borne Disease Working Group" Frontiers in Medicine, 8 (643235) pp. 1-8 (2021).
Embers, M.E., et al. "Survival strategies of Borrelia burgdorferi, the etiologic agent of Lyme disease" Microbes and Infection, 6, pp. 1, 313-318 (2004).
Embers, M. E., et al. "Borrelia burgdorferi Spirochetes That Harbor Only a Portion of the 1p28-1 Plasmid Elicit Antibody Responses Detectable with the C6 Test for Lyme Disease" Clinical and Vaccine Immunology, 14 (1) pp. 90-93 (2006).
Embers, M.E., et al. "Dominant Epitopes of the C6 Diagnostic Peptide of Borrelia burgdorferi Are Largely Inaccessible to Antibody on the Parent VIsE Molecule" Clinical and Vaccine Immunology, 14 (8) pp. 931-936 (2007).
Embers, M.E., et al. "Antigenicity and recombination of VIsE, the antigenic variation protein of Borrelia burgdorferi, in rabbits, a host putatively resistant to long-term infection with this spirochete" Federation of European Microbiological Societies, 50, pp. 421-429 (2007).

(56) References Cited

OTHER PUBLICATIONS

Embers, M.E., et al. "The Failure of Immune Response Evasion by Linear Plasmid 28-1-Deficient Borrelia burgdorferi Is Attributable to Persistent Expression of an Outer Surface Protein" Infection and Immunity, 76 (9) pp. 3984-3991 (2008).

Embers, M.E., et al. "Dynamic Longitudinal Antibody Responses during Borrelia burgdorferi Infection and Antibiotic Treatment of Rhesus Macaques" Clinical and Vaccine Immunology, 19 (8) pp. 1218-1226 (2012).

Embers, M.E., et al. "Borrelia burgdorferi Persistence Post-antibiotic Treatment" The Pathogenic Spirochetes: strategies for evasion of host immunity and persistence (2012).

Embers, M.E., et al. "Persistence of Borrelia burgdorferi in Rhesus Macaques following Antibiotic Treatment of Disseminated Infection" PLoS ONE, 7 (1), pp. 1-12 (2012).

Embers, M.E., et al. "Correction: Persistence of Borrelia burgdorferi in Rhesus Macaques following Antibiotic Treatment of Disseminated Infection" PLoS ONE (2013).

Embers, M.E., et al. "Feeding of Ticks on Animals for Transmission and Xenodiagnosis in Lyme Disease Research" Journal of Visualized Experiments, (78) pp. 1-8 (2013).

Embers, M.E., et al. "Vaccination against Lyme disease: past, present, and future" Frontiers in Cellular and Infection Microbiology, 3 (6) pp. 1-15 (2013).

Embers, M. E., et al. "Five-Antigen Fluorescent Bead-Based Assay for Diagnosis of Lyme Disease" American Society For Microbiology, Clinical and Vaccine Immunology, 23(4) pp. 294-303 (2016).

Embers, M.E., et al. "Variable manifestations, diverse seroreactivity and post-treatment persistence in non-human primates exposed to Borrelia burgdorferi by tick feeding" Plos One, pp. 1-22 (2017).

Embers, M.E., et al. "Immunological Responses to the Relapsing Fever Spirochete Borrelia turicatae in Infected Rhesus Macaques: Implications for Pathogenesis and Diagnosis" American Society for Microbiology, Infection and Immunity, 87 (4) pp. 1-14 (2019).

Embers, M.E., et al. "Diagnostic challenges in Lyme disease" (2024).

Embers, M.E., et al. "Combination Antibiotic Therapy for Treatment of Lyme Disease" (2024).

Feng, J. "Stationary Phase Persister/Biofilm Microcolony of Borrelia burgdorferi Causes More Severe Disease in a Mouse Model of Lyme Arthritis: Implications for Understanding Persistence, Post-Treatment Lyme Disease Syndrome (PTLDS), and Treatment Failure" Discovery Medicine, pp. 1-11 (2024).

Gadila, S., et al. "Detecting Borrelia Spirochetes: A Case Study With Validation Among Autopsy Specimens" Frontiers in Neurology, 12 (628045) pp. 1-14 (2021).

Gadila, S., et al. "Direct Detection of Borrelia Species in Tissues" Methods Mol Biol. (2024).

Gautam, A., et al. "Differential expression and regulation of inflammatory mediators in macrophages from Lyme disease-resistant C57BL/6J and disease-susceptible C3H/HeN mice (37.6)" J Immunol (2010).

Goddard, J., et al. "Comparison of Tick Feeding Success and Vector Competence for Borrelia burgdorferi Among Immature Ixodes scapularis (Ixodida: Ixodidae) of Both Southern and Northern Clades" Population Biology/Genetics, 52 (1) pp. 81-85 (2015).

Izac, J., et al. "Analysis of the antigenic determinants of the OspC protein of the Lyme disease spirochetes: Evidence that the C10 motif is not immunodominant or required to elicit bactericidal antibody responses" Vaccine, 37, pp. 1, 2402-2407 (2019).

Jacobs, M., et al. "Borrelia burgdorferi Migration Assays for Evaluation of Chemoattractants in Tick Saliva" Pathogens, 11 (530) pp. 1-13 (2022).

Kight, E., et al. "Direct Capture and Early Detection of Lyme Disease Spirochete in Skin with a Microneedle Patch" Biosensors, 12 (819) pp. 1-18 (2022).

Koetsveld, J., et al. "Borrelia miyamotoi infection leads to cross-reactive antibodies to the C6 peptide in mice and men" Clinical Microbiology and Infection, 26, pp. 513.e1-513.e6 (2020).

Kumar, D., et al. "Is selenoprotein K required for Borrelia burgdorferi infection within the tick vector Ixodes scapularis?" Parasites & Vectors, 12 (289) pp. 1-8 (2019).

Kumar, D., et al. "Identification of microRNAs in the Lyme Disease Vector Ixodes scapularis" International Journal of Molecular Sciences, 23 (5565) pp. 1-16 (2022).

Lahey, L. J. "Development of a Multiantigen Panel for Improved Detection of Borrelia burgdorferi Infection in Early Lyme Disease" Journal of Clinical Microbiology, 53:12 pp. 3834-3841 (2015).

Lopez, J., et al. "Real-Time Monitoring of Disease Progression in Rhesus Macaques Infected With Borrelia turicatae by Tick Bite" The Journal of Infectious Diseases, 210, pp. 1639-1648 (2014).

Narasimhan, S., et al. "Repeated Tick Infestations Impair Borrelia burgdorferi Transmission in a Non-Human Primate Model of Tick Feeding" Pathogens, 12 (132) pp. 1-12 (2023).

Pflughoeft, K., et al. "Multi-platform Approach for Microbial Biomarker Identification Using Borrelia burgdorferi as a Model" Frontiers in Cellular and Infection Microbiology, 9 (179) pp. 1-10 (2019).

Phillips, S., et al. "Author's response to comments by Sigal and Hassett, Phillips et al., and Shapiro et al. From Victoria Cairns" International Journal of Epidemiology, pp. 1440-1443 (2005).

Romer, T., et al. "The DEXA-PSYCH Study: Repurposing Dexamethasone for Treatment of Moderate-to-Severe Depression—A Study Protocol" Journal of Affective Disorders Reports, 12, pp. 100517 (2023).

Schiller, Z., et al. "Blocking Borrelia burgdorferi transmission from infected ticks to nonhuman primates with a human monoclonal antibody" The Journal of Clinical Investigation, 131 (11) pp. 1-12 (2021).

Scholl, D., et al. "Immunomodulatory effects of tick saliva on dermal cells exposed to Borrelia burgdorferi, the agent of Lyme disease" Parasites & Vectors, pp. 1-17 (2016).

Sell, M., et al. "Visualizing Borrelia burgdorferi Infection Using a Small-Molecule Imaging Probe" American Society for Microbiology, Journal of Clinical Microbiology, 59 (7) pp. 1-11 (2021).

WO: International Search Report and Written Opinion dated Feb. 6, 2025 in PCT Application No. PCT/US2024/43773.

Wormser, G., et al. "Effect of Borrelia burgdorferi Genotype on the Sensitivity of C6 and 2-Tier Testing in North American Patients with Culture-Confirmed Lyme Disease" Clinical Infectious Diseases, 47, pp. 910-914 (2008).

* cited by examiner

Non-Normalized Controls From IgG Plates by Antigen

Control Sample Labels

Non-Normalized Controls From IgG Plates by Antigen

Control Sample Labels

Non-Normalized Controls From IgG Plates by Antigen

Control Sample Labels

Fluorescence (Normalized with Mean Control per Plate) From IgG Plates Combined

Antigen

PC = Plate Control
DC = Disease Control
HC = Healthy Patient
LD – Lyme
LDA = Acute Lyme

Fluorescence (Normalized with Mean Control per Plate) From IgM Plates Combined

PC = Plate Control
DC = Disease Control
HC = Healthy Patient
LD – Lyme
LDA = Acute Lyme

| LymeSeq | Disease State | | |
| --- | --- | --- | --- |
| | Pos | Neg | Total |
| Pos | 144 | 13 | 157 |
| Neg | 14 | 137 | 151 |
| Total | 158 | 150 | |

FIG. 6

| Samples | 2-tier positive | C6 positive* | 5-plex positive |
|---|---|---|---|
| Control (endemic, healthy) | 0/20 (0%) | 0/20 (0%) | 1(equiv)/20 (0%) |
| PTLDS | 30/75 (40.0%) | 24-27 (5 equiv)/75 (32.0%) | 55/75 (73.3%) |
| 2-tier negative patients that are 5-plex positive | | 26/45 (57.8%) | |
| C6-negative patients that are 5-plex positive | | 24/51 (47.1%) | |

FIG. 9

MULTI-ANTIGEN DIAGNOSTIC FOR DETECTING LYME DISEASE

CROSS REFERENCE TO RELATED APPLICATION

This application claims priority to, and the benefit of, U.S. Provisional Patent Application 63/534,783 filed on Aug. 25, 2023, and entitled "Multi-Antigen Diagnostic for Detecting Lyme Disease," the entire contents of which are incorporated by reference herein.

FIELD

This disclosure relates to methods of diagnosing Lyme disease, using one or more antigens.

BACKGROUND

Lyme disease continues to increase in the Western hemisphere. With almost 500,000 cases per year, Lyme disease is the number one vector borne disease in the US and $3^{rd}$ most prevalent bacterial infectious disease behind chlamydia and gonorrhea (both sexually transmitted diseases). The global seroprevalence of Lyme disease is estimated at 14.5% (1.17 billion people) of the world's population (Dong Y, et. al. Global seroprevalence and sociodemographic characteristics of Borrelia burgdorferi sensu lato in human populations: a systematic review and meta-analysis. BMJ Glob Health. 2022 June; 7(6):e007744). Current tests are only 28% accurate (Horn E J, et.al. The Lyme Disease Biobank: Characterization of 550 Patient and Control Samples from the East Coast and Upper Midwest of the United States. J Clin Microbiol. 2020 May 26; 58 (6):e00032-20.) in early Lyme disease, and less than 50% accurate overall (Cook M J, Puri B K. Commercial test kits for detection of Lyme borreliosis: a meta-analysis of test accuracy. Int J Gen Med. 2016 Nov. 18; 9:427-440). Early LD is often characterized by erythema migrans (EM), an erythematous, expanding, skin lesion that develops at the site of the tick bite and that sometimes has a central clearing. Horn E J, Dempsey G, Schotthoefer A M, Prisco U L, McArdle M, Gervasi S S, Golightly M, De Luca C, Evans M, Pritt B S, Theel E S, Iyer R, Liveris D, Wang G, Goldstein D, Schwartz I. The Lyme Disease Biobank: Characterization of 550 Patient and Control Samples from the East Coast and Upper Midwest of the United States. J Clin Microbiol. 2020 May 26; 58 (6):e00032-20. doi: 10.1128/JCM.00032-20. PMID: 32102853; PMCID: PMC7269379. While EM is a common manifestation of early LD, only 70 to 80% of individuals with early LD develop EM (4, 5); in U.S. Centers for Disease Control and Prevention (CDC) surveillance data from 2008 to 2015, 72.2% of individuals presented with EM. Even when present, EM may not have the classic bull's-eye shape, which can confound a clinical diagnosis. Early LD can be accompanied by nonspecific, virus infection-like signs and symptoms, including headache, fever, chills, fatigue, myalgias, and arthralgias. As the Borreliae disseminate, multiple EM lesions may appear, as may 7th cranial nerve palsy, meningitis, or Lyme carditis. Late stages of LD include neuroborreliosis and Lyme arthritis.

The diagnosis of early LD is based on clinical and epidemiological features and is sometimes supported by laboratory test results. For patients with EM lesions of >5 cm and a history compatible with tick exposure in an area of endemicity, a presumptive diagnosis of LD can be made, and treatment can be initiated. Testing is not indicated for these patients, as the commonly used serologic methods would likely be negative due to a lack of detectable antibodies early in disease. For the ~30% of patients presenting without well-defined EM, an accurate diagnosis in the absence of positive laboratory test results is almost impossible.

Testing has traditionally been performed using a standard two-tiered testing algorithm (STTTA), which includes a first-tier enzyme immunoassay (EIA) or enzyme-linked immunosorbent assay (ELISA), and for those samples that are positive or equivocal (borderline), immunoblotting is performed. Using the interpretative algorithm published by the CDC, a positive immunoblotting result consists of at least 2 of 3 positive bands on the IgM immunoblot within 30 days of symptom onset or 5 to 10 bands on the IgG immunoblot at any time. More recently, the CDC endorsed a modified two-tiered testing algorithm (MTTTA). This approach still relies on a first-tier ELISA; however, in place of supplemental immunoblot testing, second-tier confirmatory testing is done using one or two other ELISAs with antigens different from those used in the first-tier ELISA. Several factors influence a positive serologic test result, including the duration of infection prior to sample collection, patient variability in the kinetics of the antibody response to an infectious agent, and the selection of appropriate antigenic targets.

The results of serologic tests may be negative in early LD, as there may not be sufficient time for the antibody response to develop, and results may be impacted based on which B. burgdorferi antigen is used in the first-tier assay. Direct detection methods, such as PCR and culture-based methods, have limitations, because B. burgdorferi is found at very low levels and only transiently in blood. Insufficiencies in current testing methodologies complicate the accurate diagnosis of early LD, contribute to delays in diagnosis and treatment, and may result in additional sequelae. Aside from the recent MTTTA, there have been limited advances in LD diagnostic testing in the past 25 years, despite the growing public health concern. With an estimated 329,000 new cases each year in the United States, improved testing modalities are urgently needed. High treatment costs ($100 billion annually in the US and EU) are driven by undiagnosed or misdiagnosed patients developing Persistent Lyme Disease, which could be avoided with proper and early diagnosis (Johnson, LDo, 2018). Thus, there is a critical gap because early detection and treatment can result in better treatment outcomes.

SUMMARY

In an aspect, a method is provided comprising, consisting of, or consisting essentially of contacting at least two antibodies to a plurality of antigens, the plurality of antigens comprising, consisting of, or consisting essentially of: C6, GlpQ, p35, p66, OspC, DbpA, OppA2, ErpQ, OspE, OspC peptide 2 (OspC2); detecting reactivity between the at least two antibodies and the plurality of antigens; and evaluating the reactivity to diagnose Lyme disease. In some embodiments, the at least two antibodies are IgG and IgM. In some embodiments, the plurality of antigens comprises, consists of, or consists essentially of OspC2, OspC, and C6. In some embodiments, the plurality of antigens comprises, consists of, or consists essentially of OspC2 and OspC. In some embodiments, the plurality of antigens comprises, consists of, or consists essentially of OspC2 and C6. In some embodiments, the plurality of antigens comprises, consists of, or consists essentially of OspC and C6. In some embodiments, the plurality of antigens comprises, consists of, or consists essentially of C6, GlpQ, p35, p66, OspC, DbpA, OppA2, ErpQ, OspE, and OspC2. Any antigens described above will have predictive value, however, adding one or more additional antigens to the analytical panels described herein may increase the panel's predictive value for clinical purposes. A sensitivity and/or specificity of at least about 80% or higher are preferred, more preferably at least about 85% or higher, and most preferably at least about 90% or 95% or higher.

In some embodiments, the method further comprises exposing at least two *Borrelia* antigens to a biological sample. In some embodiments, the at least two *Borrelia* antigens comprise, consist of, or consist essentially of OspC2, OspC, and C6. In some embodiments, the at least two *Borrelia* antigens comprise, consist of, or consist essentially of OspC2 and OspC. In some embodiments, the at least two *Borrelia* antigens comprise, consist of, or consist essentially of OspC2 and C6. In some embodiments, the at least two *Borrelia* antigens comprise, consist of, or consist essentially of OspC and C6. In some embodiments, the at least two *Borrelia* antigens comprise, consist of, or consist essentially of C6, GlpQ, p35, p66, OspC, DbpA, OppA2, ErpQ, OspE, and OspC2. In some embodiments, the method further comprises coupling any of the antigens to a plurality of cytometric beads. In some embodiments, the method further comprises coupling C6, GlpQ, p35, p66, OspC, DbpA, OppA2, ErpQ, OspE, and OspC2 to a plurality of cytometric beads. In some embodiments, exposing the at least two *Borrelia* antigens to the biological sample results in binding of at least two antibodies to the plurality of antigens. In some embodiments, the antibodies which bind to the at least two *Borrelia* antigens are any one or more of IgM and IgG. In some embodiments, the any one or more of IgM and IgG is connected to a fluorophore and wherein detecting reactivity between the at least two antibodies and the plurality of antigens comprises detecting a fluorescent signal from the fluorophore. In some embodiments, the biological sample derives from a subject that is suspected of having Lyme disease.

In some embodiments, reactivity between the at least two antibodies and the plurality of antigens is measured in fluorescence values. In some embodiments, the method further comprises coupling any one or more of C6, GlpQ, p35, p66, OspC, DbpA, OppA2, ErpQ, OspE, and OspC2 antigens to a plurality of cytometric beads. In some embodiments, the method further comprises detecting antibody binding to any one more of C6, GlpQ, p35, p66, OspC, DbpA, OppA2, ErpQ, OspE, and OspC2 antigens coupled to the plurality of beads.

In an aspect, a system to evaluate reactive data is provided, the system comprising, consisting of, or consisting essentially of a processor; and a tangible, non-transitory memory configured to communicate with the processor, the tangible, non-transitory memory having instructions stored thereon that, in response to execution by the processor, cause the processor to perform operations comprising, consisting of, or consisting essentially of: obtaining reactivity data, the reactivity data further comprising, consisting of, or consisting essentially of columns of data each corresponding to unique antibody-antigen interactions; applying a decision tree to the reactivity data using a series of steps, the series of steps comprising, consisting of, or consisting essentially of: evaluating the columns of data; determining uncertainty of each column of data; splitting each column of data into a high and a low uncertainty range; assigning a cutoff reactivity value that separates high and low uncertainty ranges; comparing data to the column of data uncertainty ranges of the column of data with the highest uncertainty; progressing in one or two directions of analysis based off of the comparison; and repeating the previous process steps until one of either a predetermined maximum number of classes or an acceptable tolerance value is reached.

In embodiments, the tangible, non-transitory memory configured to communicate with the processor causes the processor to perform operations further comprising, consisting of, or consisting essentially of determining the effectiveness of the decision tree.

In an aspect, a method is provided comprising, consisting of, or consisting essentially of contacting at least one antibody to a plurality of antigens; detecting reactivity between the at least one antibody and the plurality of antigens; quantifying into values the reactivity between the at least one antibody and plurality of antigens into values; normalizing the values; analyzing the normalized values; and diagnosing the presence of Lyme disease.

In embodiments, the method further comprises differentiating between Post-Treatment Lyme Disease and Acute Lyme disease.

In an aspect, a multiplex immunoassay is provided comprising, consisting of, or consisting essentially of a plurality of substrate locations; and a plurality of antigens immobilized at the plurality of substrate locations, the plurality of antigens comprising, consisting of, or consisting essentially of any two or more of: C6, GlpQ, p35, p66, OspC, DbpA, OppA2, ErpQ, OspE, and OspC2. In embodiments, the plurality of substrate locations comprises a cytometric bead array.

In an aspect, a method is provided, the method comprising, consisting of, or consisting essentially of: contacting at least one antigen to a biological sample; detecting reactivity between the at least one antigen bound to a plurality of antibodies in the sample, wherein the plurality of antigens comprises: C6, GlpQ, p35, p66, OspC, DbpA, OppA2, ErpQ, OspE, and OspC2; and evaluating the reactivity to diagnose Lyme disease.

In embodiments, the at least one antibody comprises IgG. In embodiments, evaluating the reactivity comprises assessing the combined fluorescence value of IgG bound to each of the plurality of antigens in the sample. In embodiments, the combined fluorescence value of IgG bound to each of the plurality of antigens in the sample is greater or equal to 5955, the biological sample is diagnosed as having Lyme disease. In embodiments, if the fluorescence value of C6/IgG has a fluorescence level of greater than or equal to about 298, OspC/IgG has a fluorescence level of greater than or equal to about 436, OspE/IgG has a fluorescence level of greater than or equal to about 305, OppA2/IgG has a fluorescence level of greater than or equal to about 531, OspC2/IgG has a fluorescence level of greater than or equal to about 167.5, Dbpa/IgG has a fluorescence level of greater than or equal to about 346, ErpQ/IgG has a fluorescence level of greater than or equal to about 362, p35/IgG has a fluorescence level of greater than or equal to about 686, p66/IgG has a fluorescence level of greater than or equal to about 689, and/or combinations thereof, the sample is classified as being positive for Lyme disease.

In embodiments, the combined fluorescence value of IgG bound to each of the plurality of antigens in the sample is less than 5955, the biological sample is diagnosed as having Lyme disease. In embodiments, if the fluorescence value of C6/IgG has a fluorescence level of less than about 298, OspC/IgG has a fluorescence level of less than about 436, OspE/IgG has a fluorescence level of less than about 305, OppA2/IgG has a fluorescence level of less than about 531, OspC2/IgG has a fluorescence level of less than about 167.5, Dbpa/IgG has a fluorescence level of less than about 346, ErpQ/IgG has a fluorescence level of less than about 362, p35/IgG has a fluorescence level of less than about 686, p66/IgG has a fluorescence level of less than about 689, and/or combinations thereof, the sample is classified as being negative for Lyme disease.

In embodiments, the at least one antibody comprises IgM. In embodiments, the reactivity comprises assessing the combined fluorescence value of IgM bound to each of the plurality of antigens in the sample. In embodiments, if the fluorescence value of C6/IgM has a fluorescence level of greater than or equal to about 2645, OspC/IgM has a fluorescence level of greater than or equal to about 400, OspE/IgM has a fluorescence level of greater than or equal to about 293.8, OppA2/IgM has a fluorescence level of greater than or equal to about 332.3, OspCV2/IgM has a fluorescence level of greater than or equal to about 342, Dbpa/IgM has a fluorescence level of greater than or equal to about 535, ErpQ/IgM has a fluorescence level of greater than or equal to about 128, p35/IgM has a fluorescence level of greater than or equal to about 235, p66/IgM has a fluorescence level of greater than or equal to about 497, and/or combinations thereof, the sample is classified as being positive for Lyme disease.

In embodiments, if the fluorescence value of C6/IgM has a fluorescence level of less than about 2645, OspC/IgM has a fluorescence level of less than about 400, OspE/IgM has a fluorescence level of less than about 293.8, OppA2/IgM has a fluorescence level of less than about 332.3, OspCV2/IgM has a fluorescence level of less than about 342, Dbpa/IgM has a fluorescence level of less than about 535, ErpQ/IgM has a fluorescence level of less than about 128, p35/IgM has a fluorescence level of less than about 235, p66/IgM has a fluorescence level of less than about 497, and/or combinations thereof, the sample is classified as being negative for Lyme disease.

In embodiments, the plurality of antigens comprises: C6, GlpQ, p35, p66, OspC, DbpA, OppA2, ErpQ, OspE, and OspC2. In embodiments, the plurality of antigens comprises: C6, OspC, and OspC2. In embodiments, the plurality of antigens comprises: C6 and OspC2. In embodiments, the plurality of antigens comprises: C6 and OspC. In embodiments, the plurality of antigens comprises: OspC, and OspC2. In some embodiments, the methods of detecting Lyme disease disclosed herein does not include assessing any one or more of the antigens: OspA; BBJ09; BB-A68 and GlpQ.

In an aspect a method is provided, the method comprising, consisting of, or consisting essentially of: administering one or more antigen to a biological sample from a patient, wherein the biological sample comprises antibodies reactive to antigens of C6, GlpQ, p35, p66, OspC, DbpA, OppA2, ErpQ, OspE, and OspC2, wherein the one or more antibodies binds to one or more of the antigens and produces a fluorescence signal when it is bound to the antigens; and detecting the fluorescence value of the one or more antibodies bound to the one or more antigens.

Technical Problem

It is an object of the disclosure to provide an array of antibody markers of Lyme disease with which Lyme disease can be diagnosed. It is another object of the disclosure to provide a diagnostic composition for detecting Lyme disease with which Lyme disease can be diagnosed (in an early stage-on or before 14-days post-tick bite). It is a further object of the disclosure to provide a kit for diagnosing Lyme disease, comprising, consisting of, or consisting essentially of the composition. It is a still further an object of the disclosure to provide a method for diagnosing Lyme disease or for providing information on a diagnosis result of Lyme disease, using the diagnosis composition or kit. It is an additional object of the disclosure to provide use of the array of antibody markers in diagnosing Lyme disease (in an early stage).

Technical Solution

To accomplish the above objects, the disclosure provides a composition for diagnosing Lyme disease, comprising, consisting of, or consisting essentially of an array of antigens on cytometric beads for measuring antibodies in a patient sample for the diagnosis of Lyme disease, a kit for diagnosing Lyme disease, comprising, consisting of, or consisting essentially of the composition, and a method for determining the presence of Lyme disease in a patient or in a subject suspected of having Lyme disease. The composition or the kit may further comprise an additional ingredient, solution or device suitable for the analysis.

In some embodiments of the disclosure, the diagnosis of Lyme disease is to selectively discriminate Lyme disease from a normal group, to selectively detect Lyme disease among various infections, to diagnose Lyme disease compared to look-alike cases from similar febrile diseases, or to diagnose Lyme disease in a subject suspected of having Lyme disease. In detail, the composition or kit for diagnosing Lyme disease can be used for diagnosing Lyme disease in a patient within the first 14 days post infection.

The composition may comprise cytometric beads comprising, consisting of, or consisting essentially of an antigen or fragment thereof selected from the group comprising, consisting of, or consisting essentially of: C6, GlpQ, p35, p66, OspC, DbpA, OppA2, ErpQ, OspE, and OspC2. The composition may comprise cytometric beads comprising, consisting of, or consisting essentially of an antigen or fragment thereof selected from the group comprising, consisting of, or consisting essentially of: C6, OspC, and OspC2. The composition may comprise cytometric beads comprising, consisting of, or consisting essentially of an antigen or fragment thereof selected from the group comprising, consisting of, or consisting essentially of: C6 and OspC2. The composition may comprise cytometric beads comprising, consisting of, or consisting essentially of an antigen or fragment thereof selected from the group comprising, consisting of, or consisting essentially of: C6 and OspC. The composition may comprise cytometric beads comprising, consisting of, or consisting essentially of an antigen or fragment thereof selected from the group comprising, consisting of, or consisting essentially of: OspC, and OspC2.

In accordance with some embodiments thereof, the disclosure provides a method for diagnosing Lyme disease in a subject or for providing information on a diagnosis result of Lyme disease, comprising, consisting of, or consisting essentially of: acquiring a sample from a subject to be diagnosed for the onset of Lyme disease; measuring antibody reactivity levels in the sample to antigens comprising, consisting of, or consisting essentially of C6, OspC, and OspC2; or C6, and OspC2; or C6 and OspC; or OspC, and OspC2; comparing the expression levels of the Lyme disease antigens with those of corresponding normal controls; and determining if the subject has Lyme disease, based on the comparison result. In the determining step, a subject is said to have Lyme disease if their antibody detection level(s) are higher than a normal control.

Advantageous Effects

As described herein, diagnostic markers (antibodies) of Lyme disease in accordance with the disclosure are useful for predicting or diagnosing Lyme disease in an early stage (within 14 days of infection). In addition, the diagnosis method disclosed herein allows for the convenient detection of Lyme disease in a non-invasive manner in a sample such as blood.

BRIEF DESCRIPTION OF THE DRAWINGS

In FIG. 5A non-lyme (DC) or healthy (HC) patients vs. acute lyme (LD) or chronic lyme (CL). As can be seen in 5A, a "positive" call is not based on reactivity to any one antigen. LD1 is highly positive for C6 whereas CL2 is highly positive for Oppa2. LD2, LD3, :D4 and CL1 do not have strong reactivity to any single antigen. As can be seen in 5A, a "negative" call is not based on reactivity to any one antigen. DC2 has relatively high reactivity to C6 and yet is still a negative call.

As can be seen in 5B, a "positive" call is not based on reactivity to any one antigen. CL1 is not highly positive for any of the antigens but is still a positive call. As can be seen in 5B, a "negative" call is not based on reactivity to any one antigen. DC2 has relatively high reactivity to Dbpa and yet is still a negative call.

FIG. 6 provide an exemplary embodiment of a confusion matrix. FIG. 6 shows a confusion matrix of the 308 patients tested in the validation cohort. 144 true positives, 137 true negatives, 13 false negatives and 14 false positives.

Figure 7:
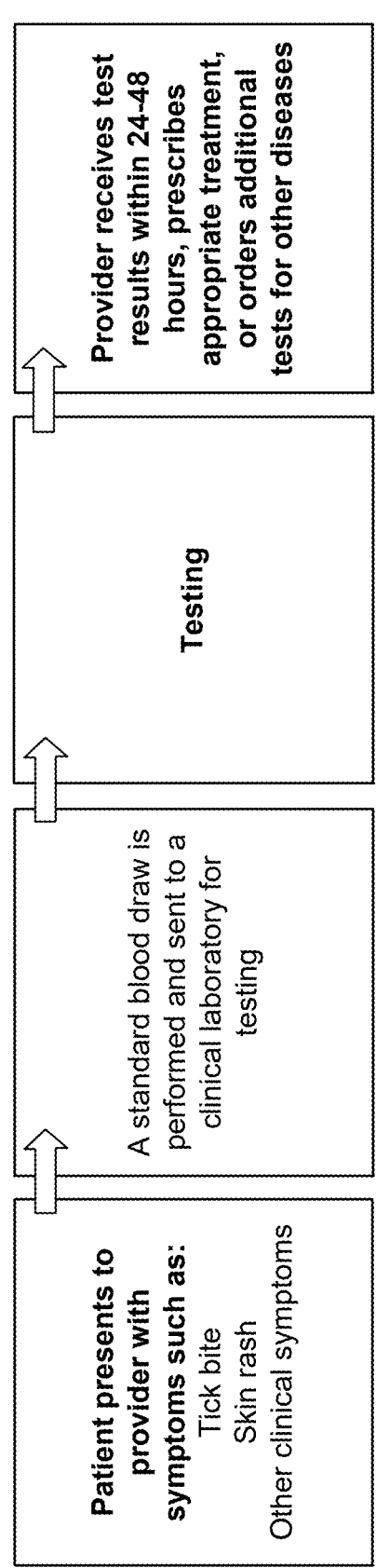

FIG. 7 is a flowchart illustrating the timeline from when a patient presents to a provider with symptoms such as a tick bite to when the provider receives test results and is able to prescribe appropriate treatment.

Figure 8A:
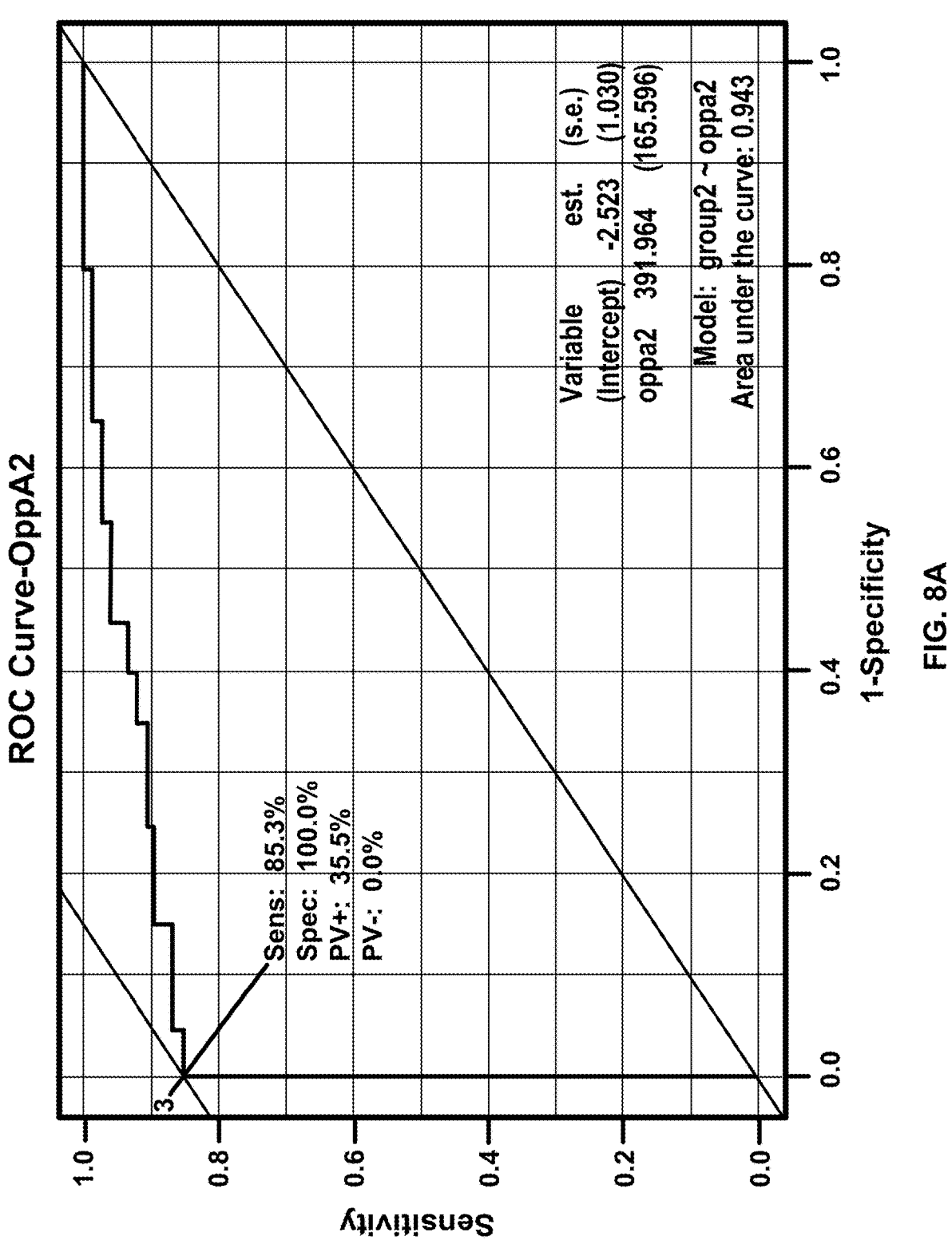
Figure 8B:
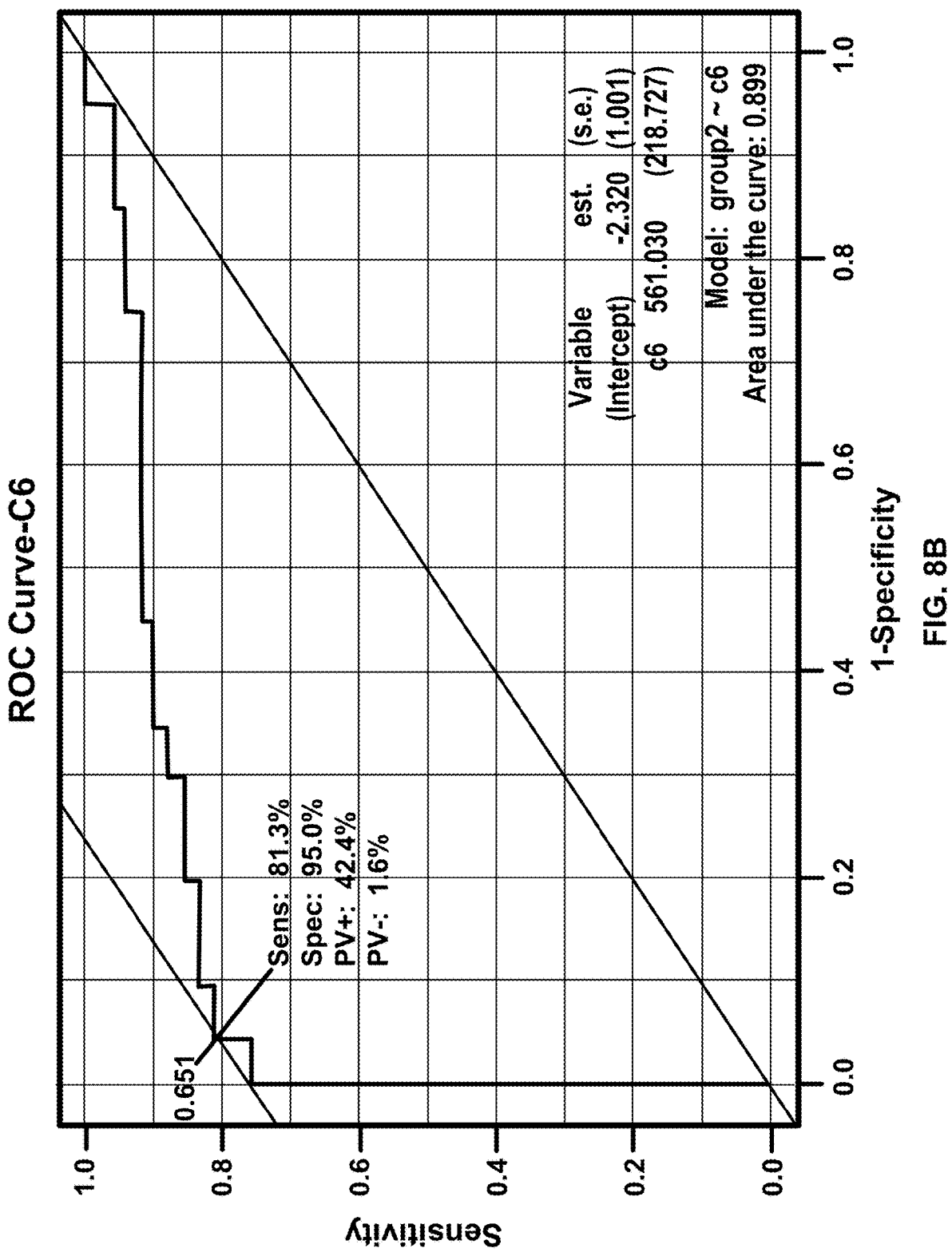

FIGS. 8A and 8B provide data showing the diagnostic performance of using the antigens OppA2 (FIG. 8A) and C6 (FIG. 8B) in Post-Treatment Lyme Disease Patients versus control patients.

FIG. 9 shows that using a 5-plex (antigens OspA, OspC, DbpA, OppA-2 and C6), there is improved performance over two-tier for Post-Treatment Lyme Disease Patients.

Figure 10:
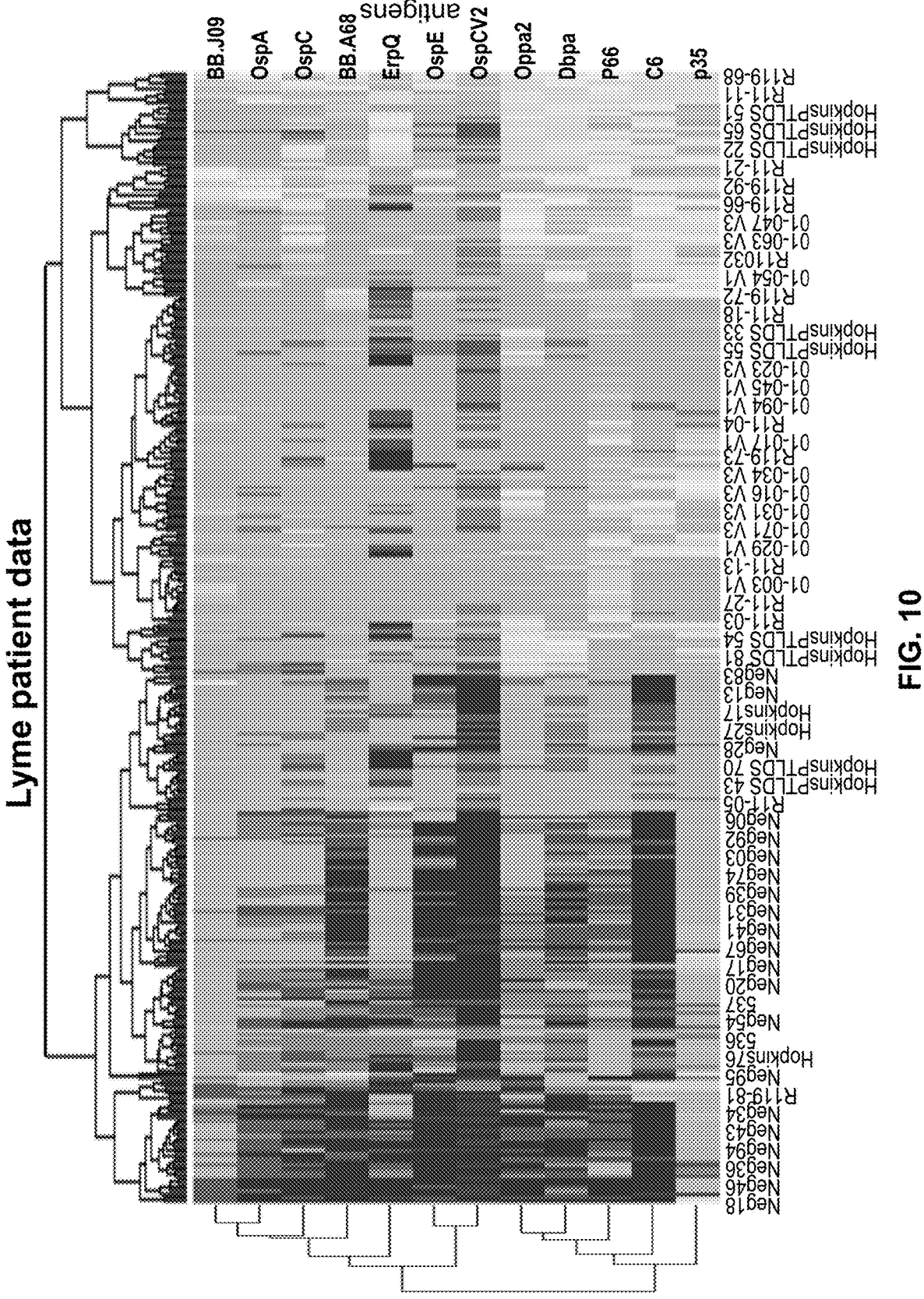
Figure 11:
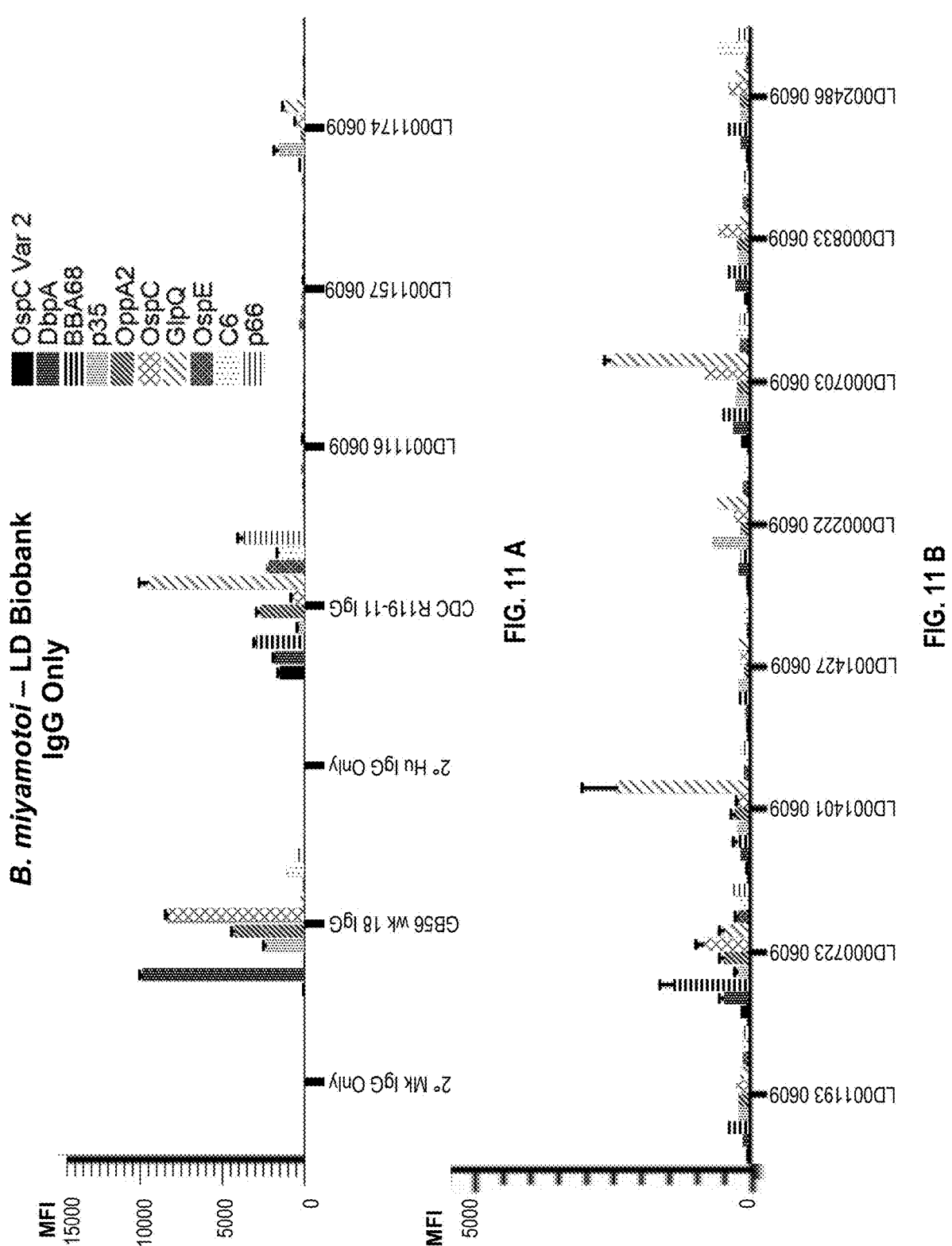
Figures 11C, 11D:
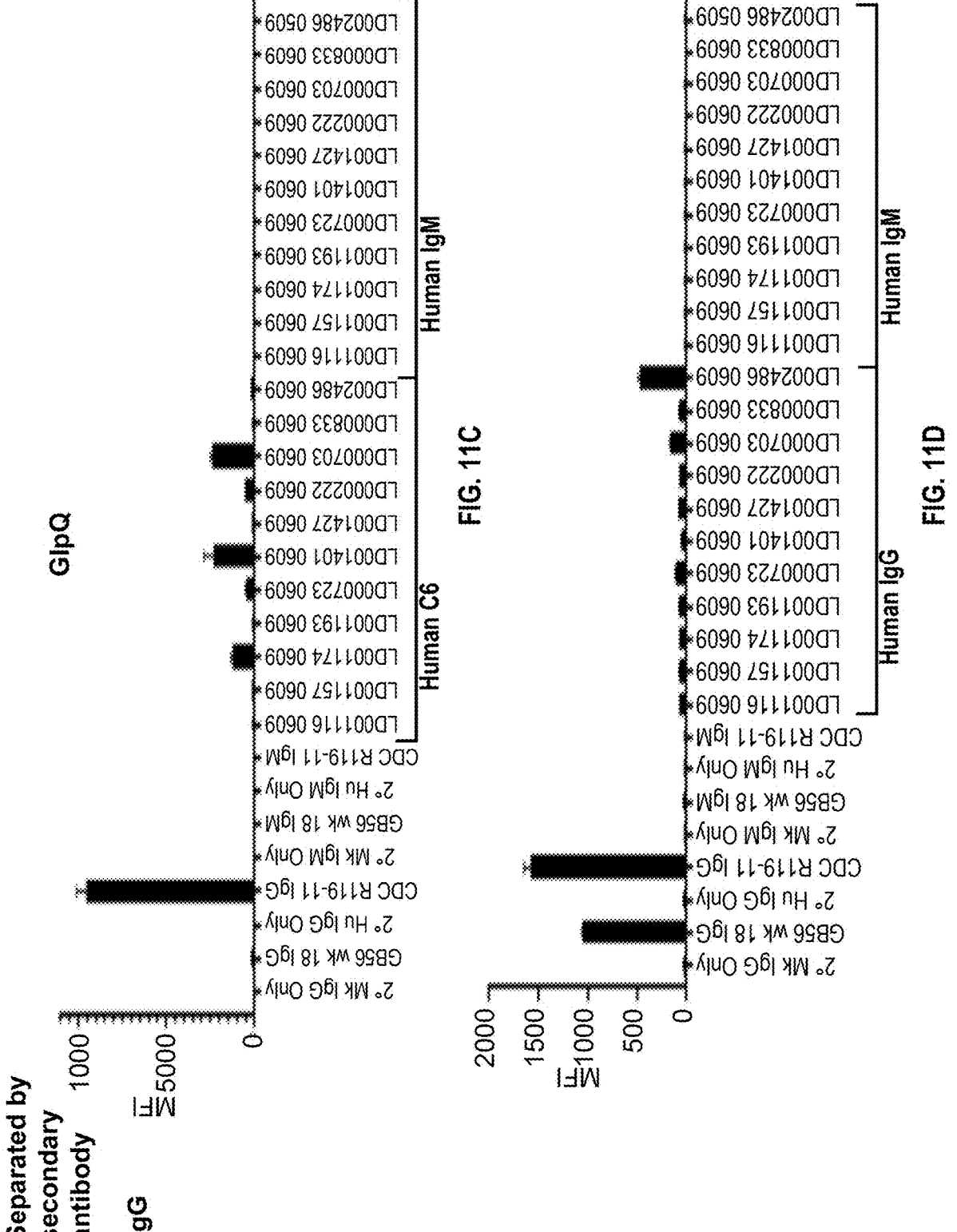

FIG. 10 is a heatmap of patients (x axis) and antigens (y axis) showing the distinction between healthy (left) and disease (right) cohorts. Light gray (right side) represents reactivity and dark gray (left) represents low reactivity. The negative patients (left) tend to show much lower signal than the infected patients on the right.

FIGS. 11A-11D shows data for an additional antigen GlpQ.

Figure 12:
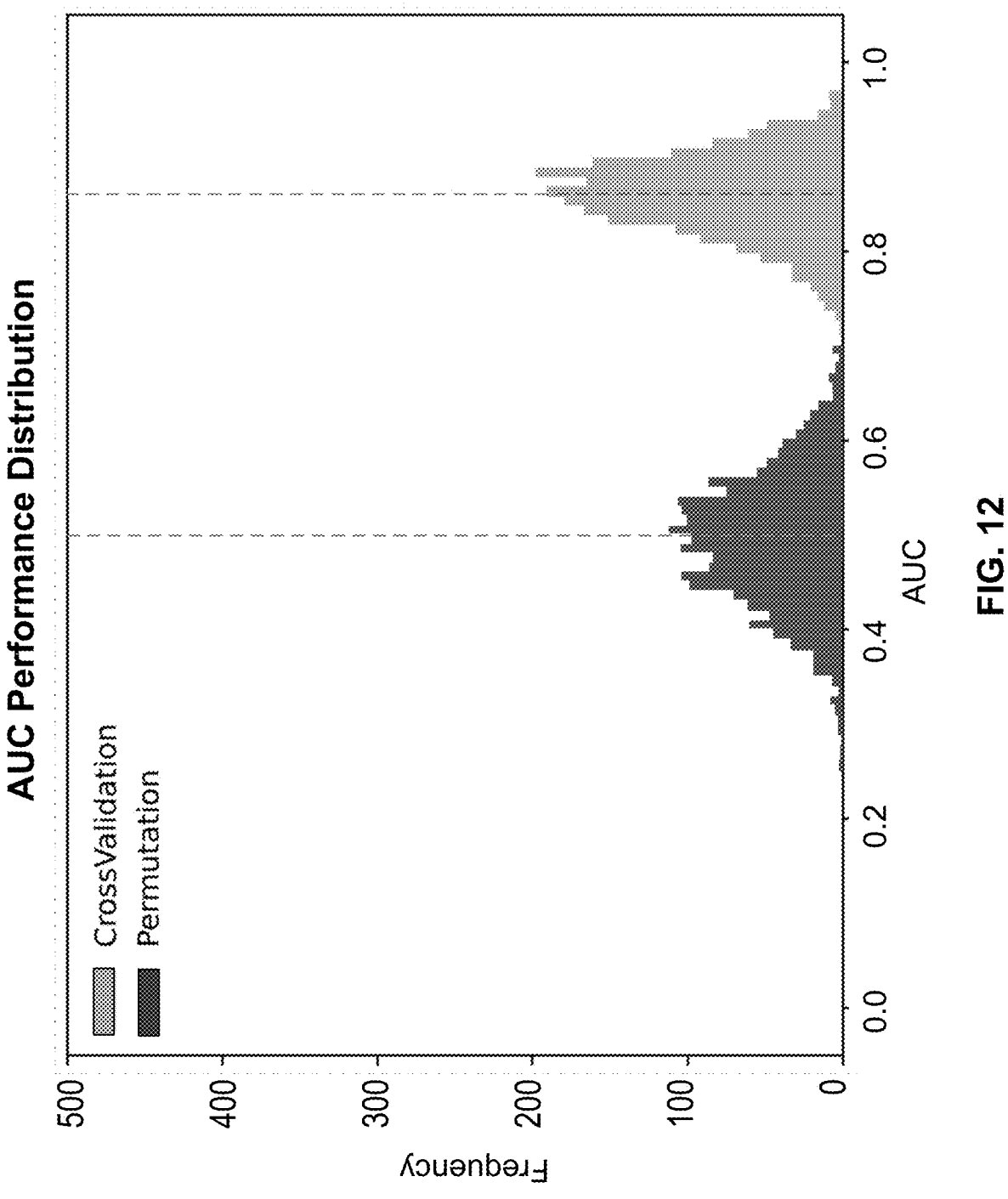

FIG. 12 is a graphical distribution of the AUC (area under the curve) scores for each of 1000 permutations of train/test cohorts. The "permutation" label means the 'Lyme', or 'non-Lyme' labels were randomized, which should result in a 50:50 accuracy of the test set. The "Cross Validation" label means the distribution of performance of the model when a random set of patients were pulled from the full dataset and used to train. The remaining cases were tested, and the AUC (an estimate of the mean between sensitivity and specificity) was recorded. This was done 1000 times; each AUC was recorded with a mean AUC of nearly 90%. In a leave-one-out cross-validation (all patients but one were used to train, the left-out patient was tested), the accuracy, sensitivity and specificity exceeded 91%. The 308 patients in the validation cohort were cross-validated using XGBoost and a 60:40 split between training and testing cases. Here, the "CrossValidation" result shows 1000 different splits of the validation data into test and training groups for XGBoost to use. The AUC (area under the curve) was calculated based on XGBoost predictions against the known disease status of the patients. The "Permutation" group is XGBoost using data where the labels "Lyme" or "Healthy" were randomly resorted, providing the algorithm with randomly assigned disease labels. The accuracy from such a permutation should fall around 50%.

Figure 13A:
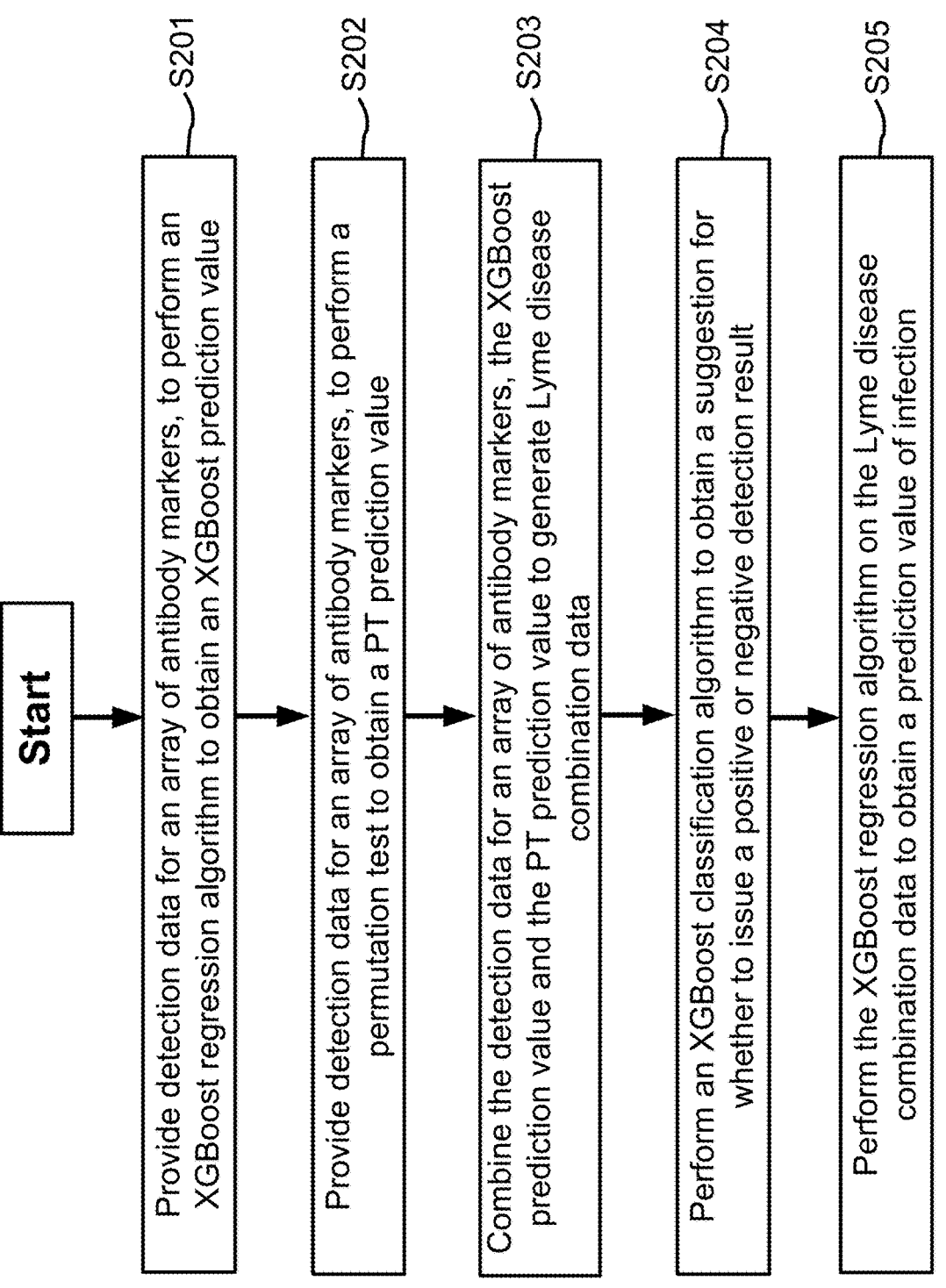

FIG. 13A is a flowchart illustrating a method for predicting Lyme disease in a subject with the aid of machine learning models as described herein.

Figure 13B:
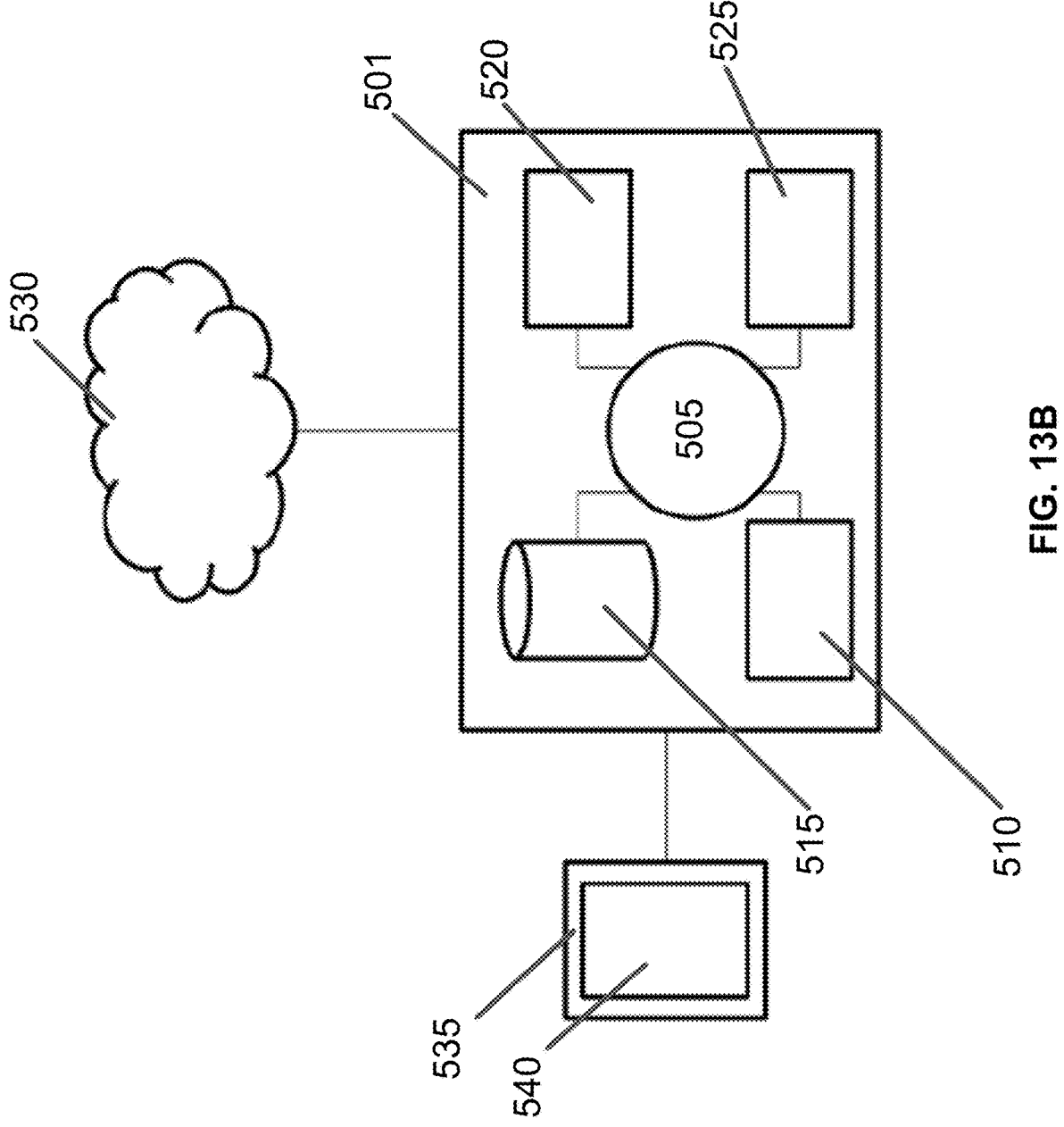

FIG. 13B depicts an example system that may execute techniques presented herein.

Figure 1A:
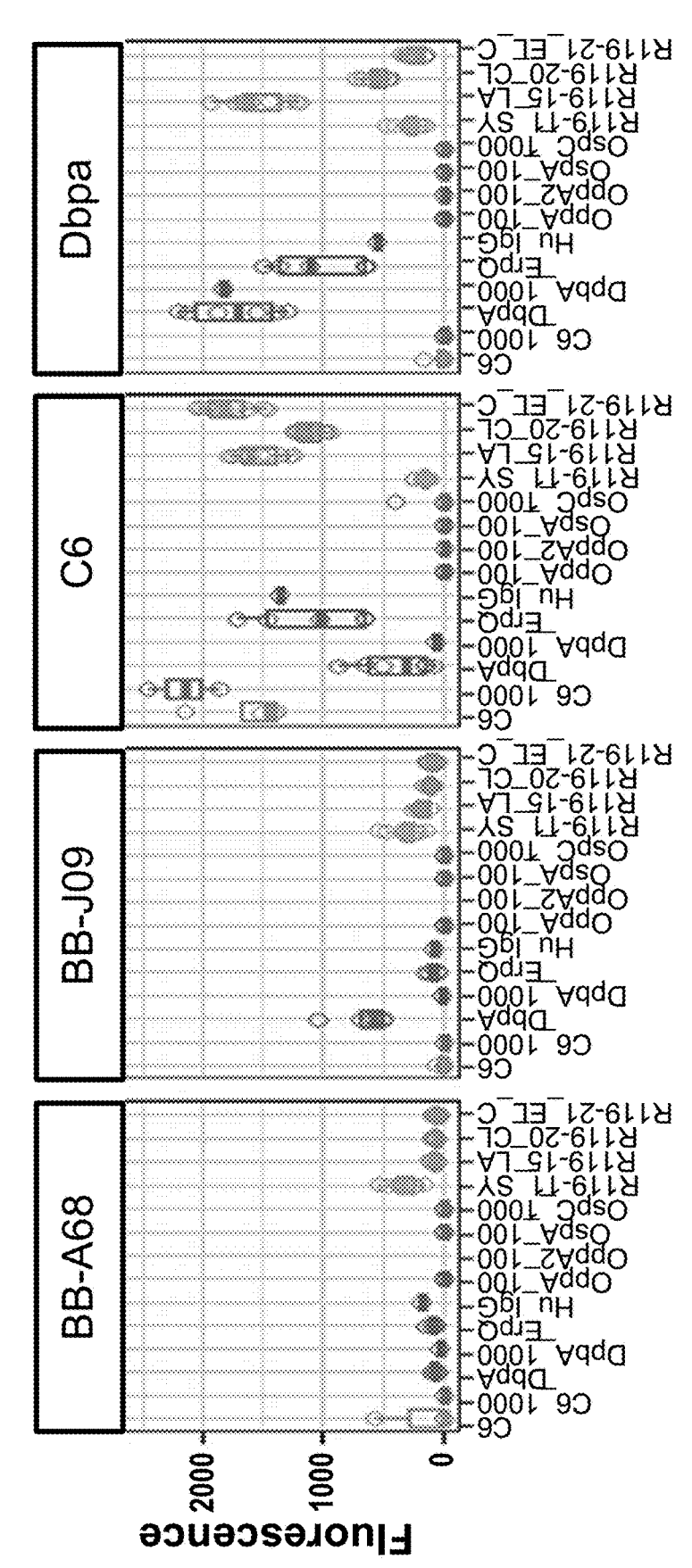
FIGS. 1A and 1B provide data showing fluorescence signals of various antigens against non-normalized controls using IgG plates (FIG. 1A) and IgM plates (FIG. 1B).
Figure 1A:
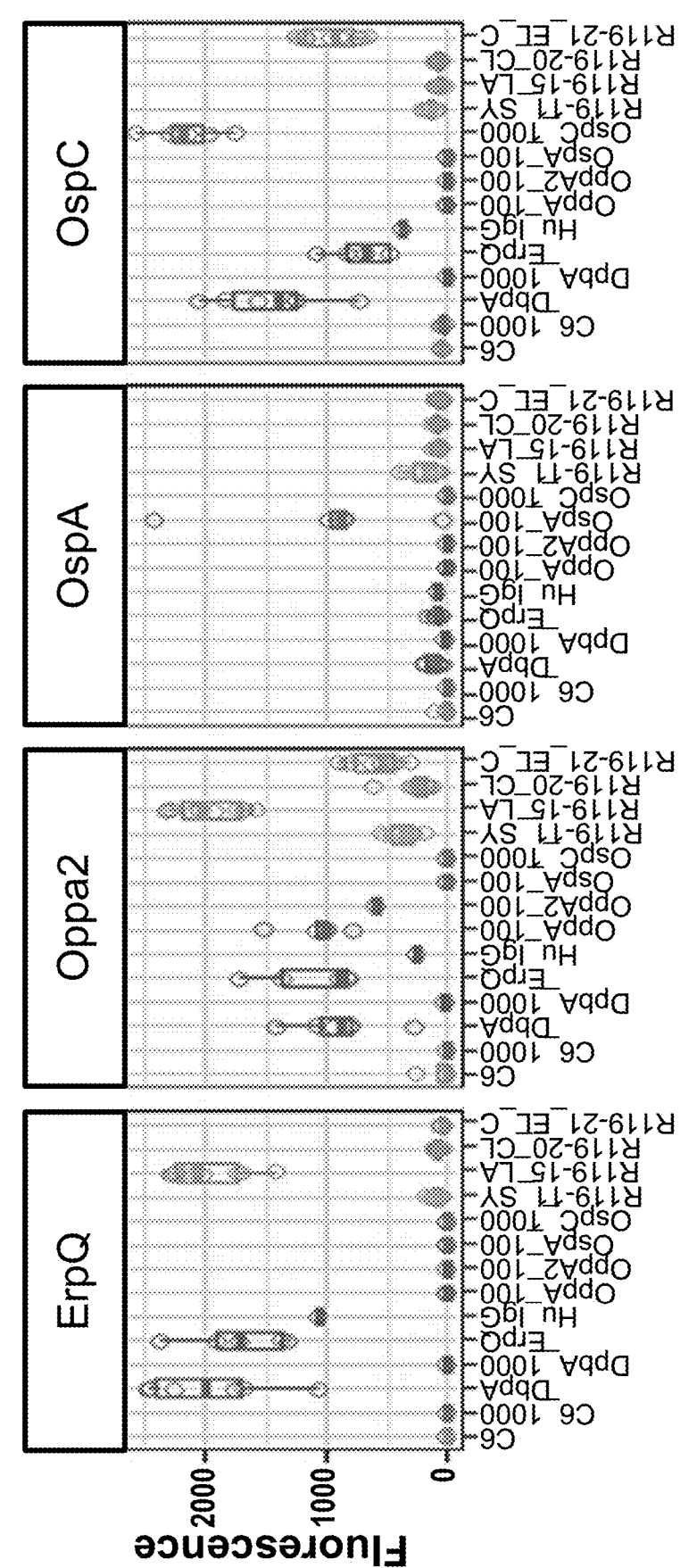
Figure 1A:
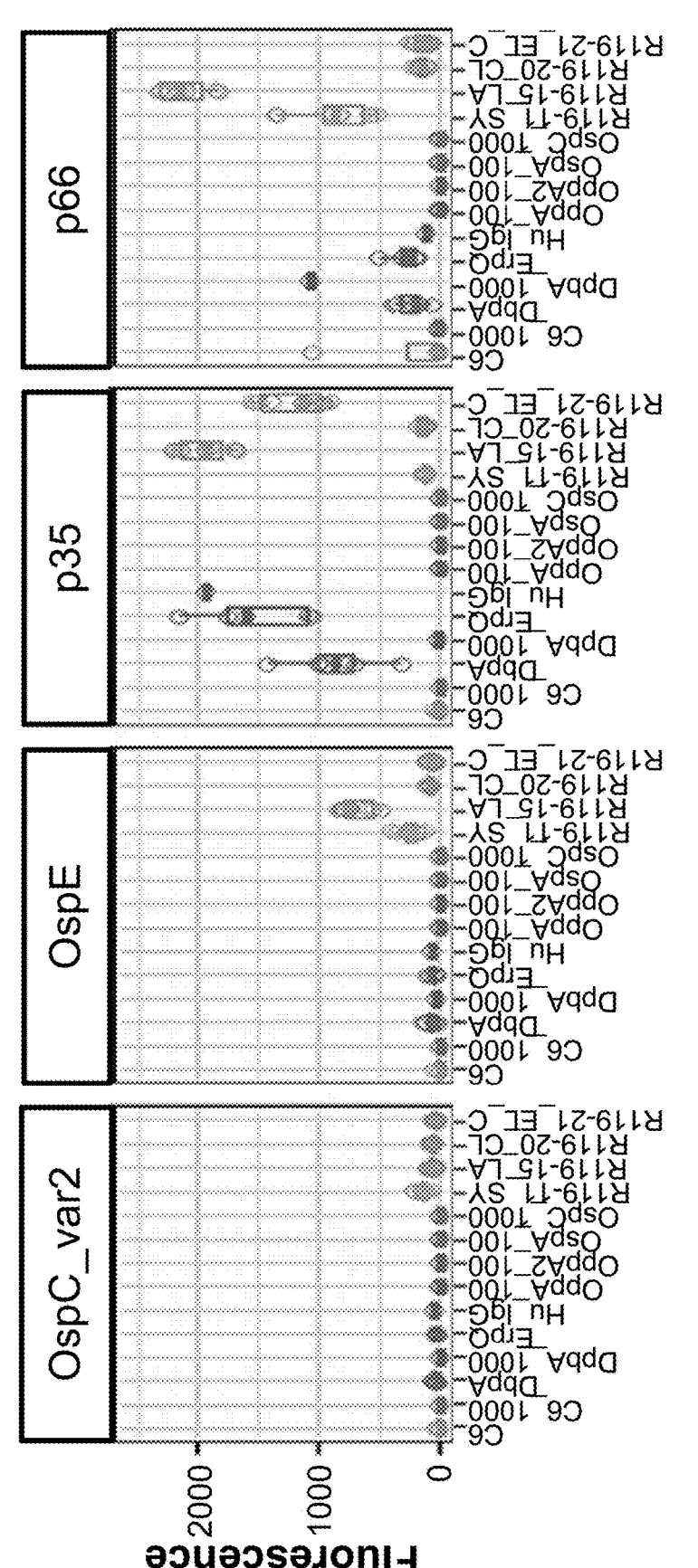
Figure 1B:
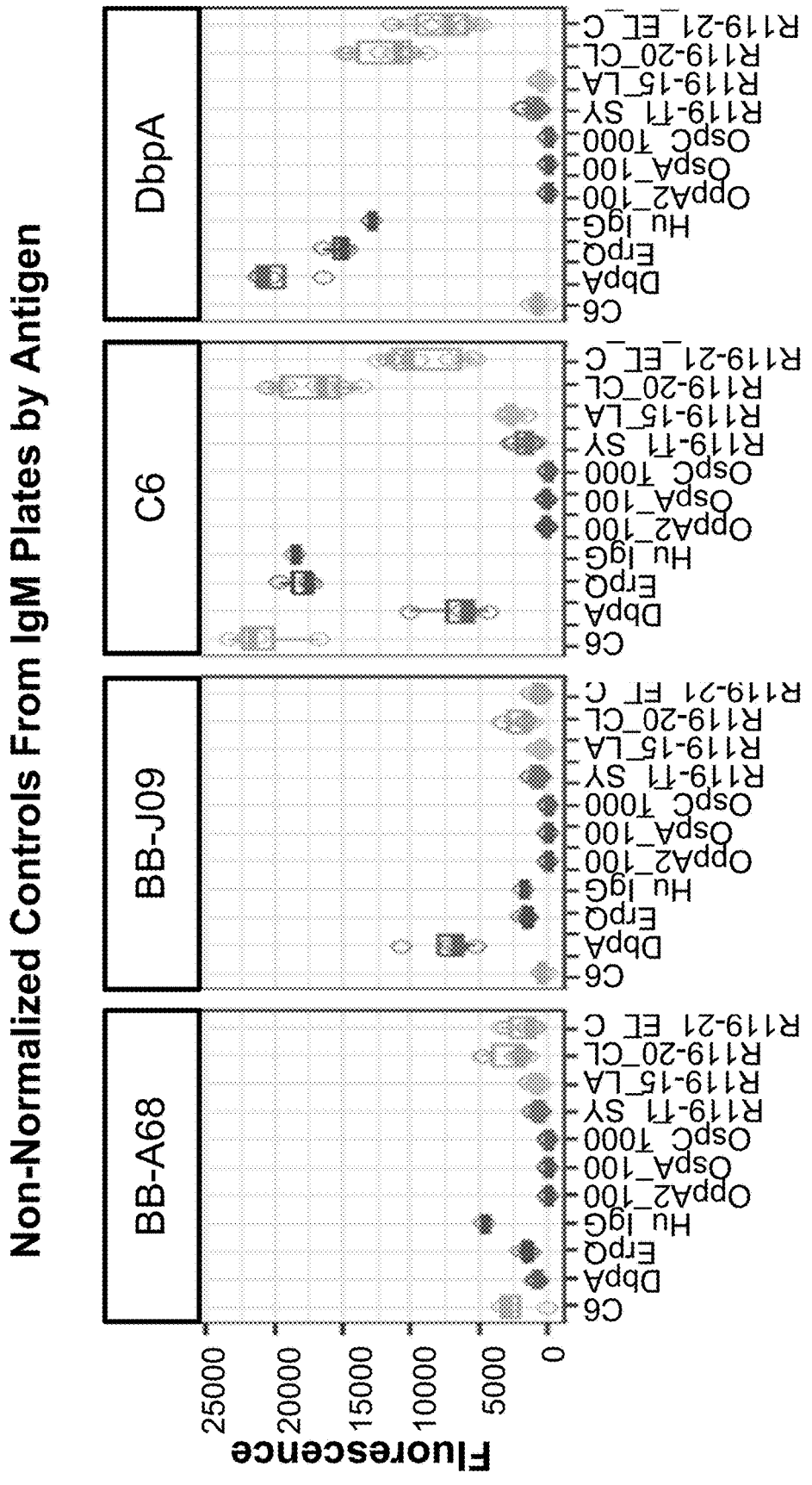
Figure 1B:
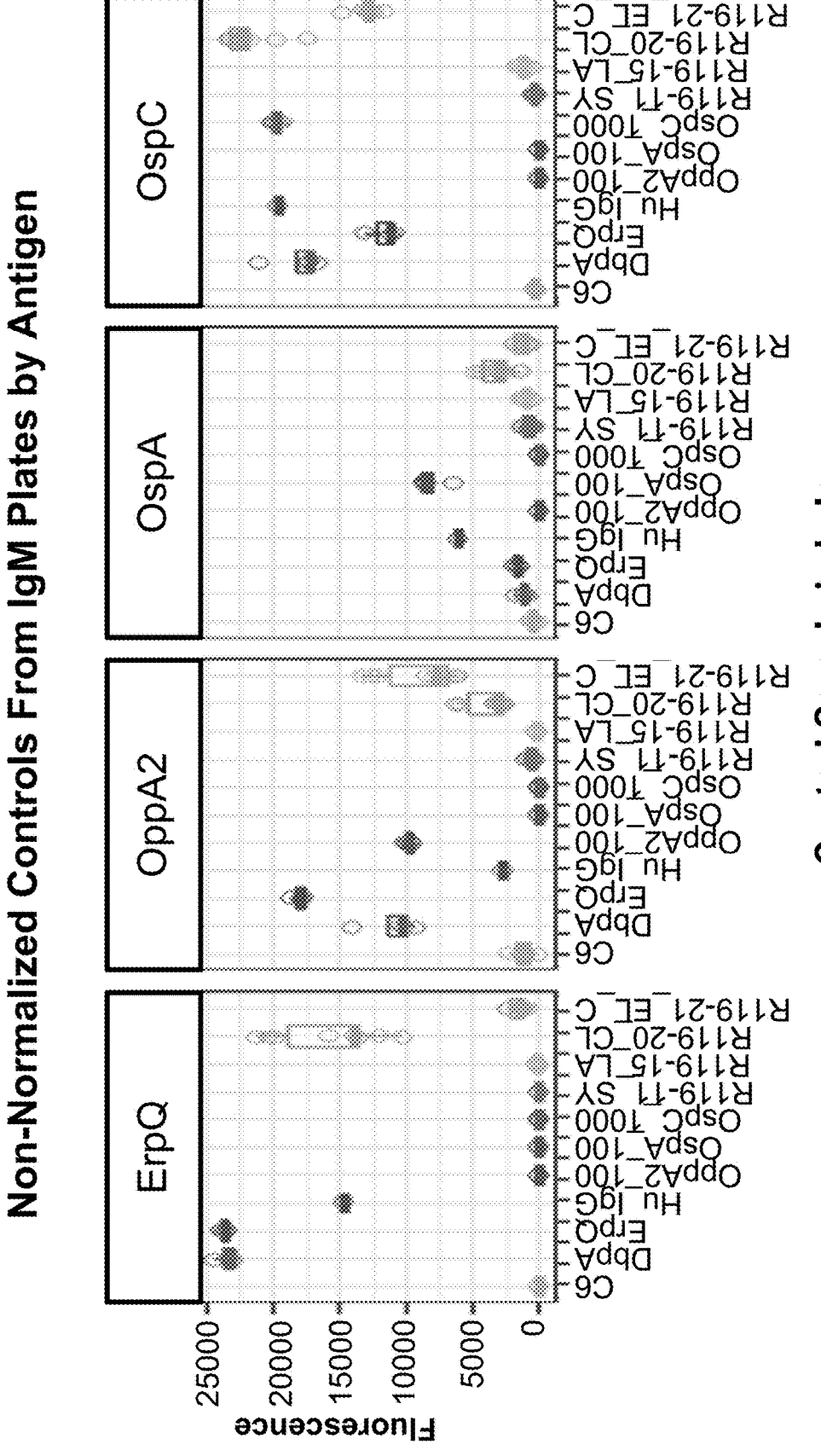
Figure 1B:
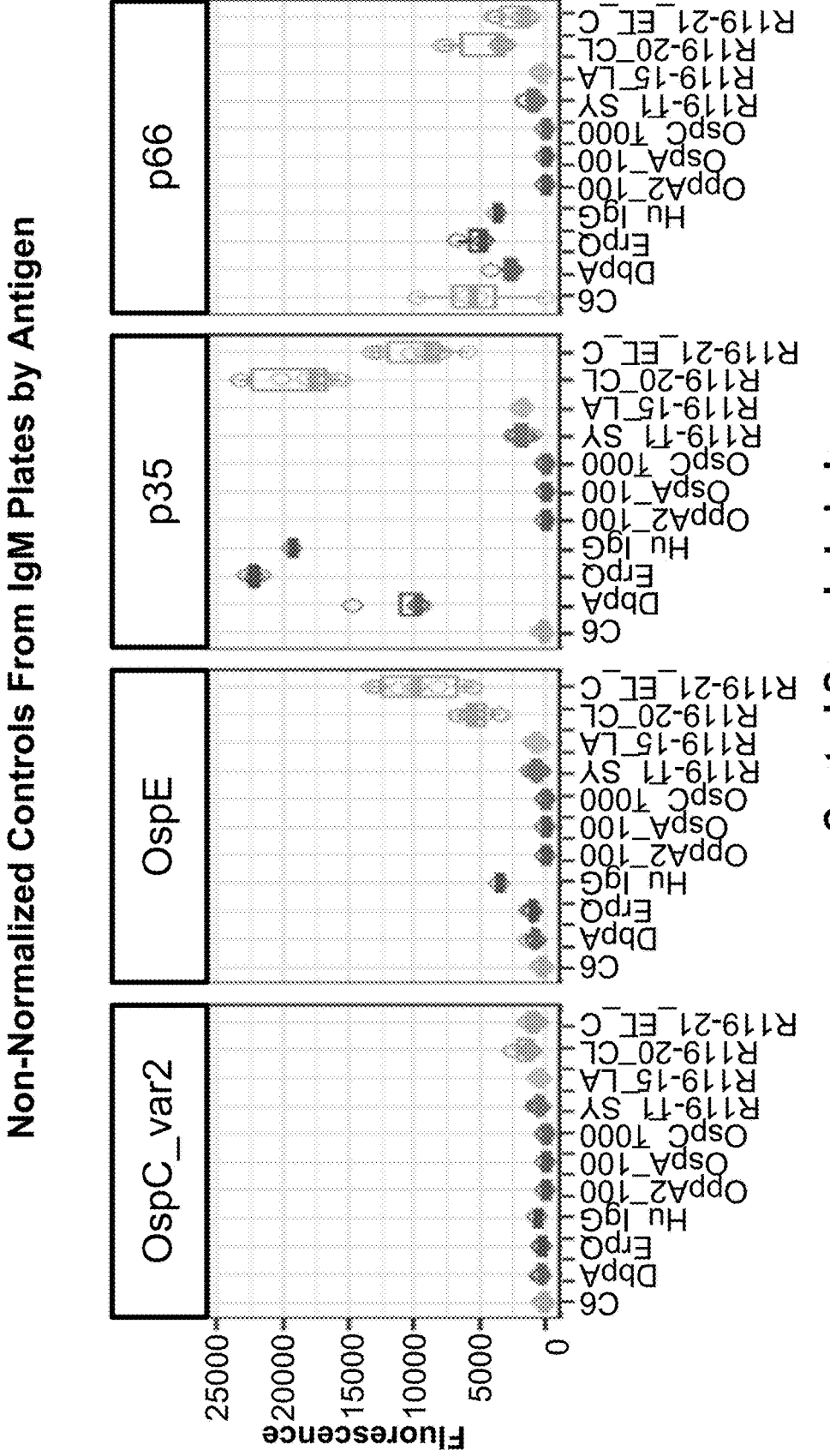
Figure 2A:
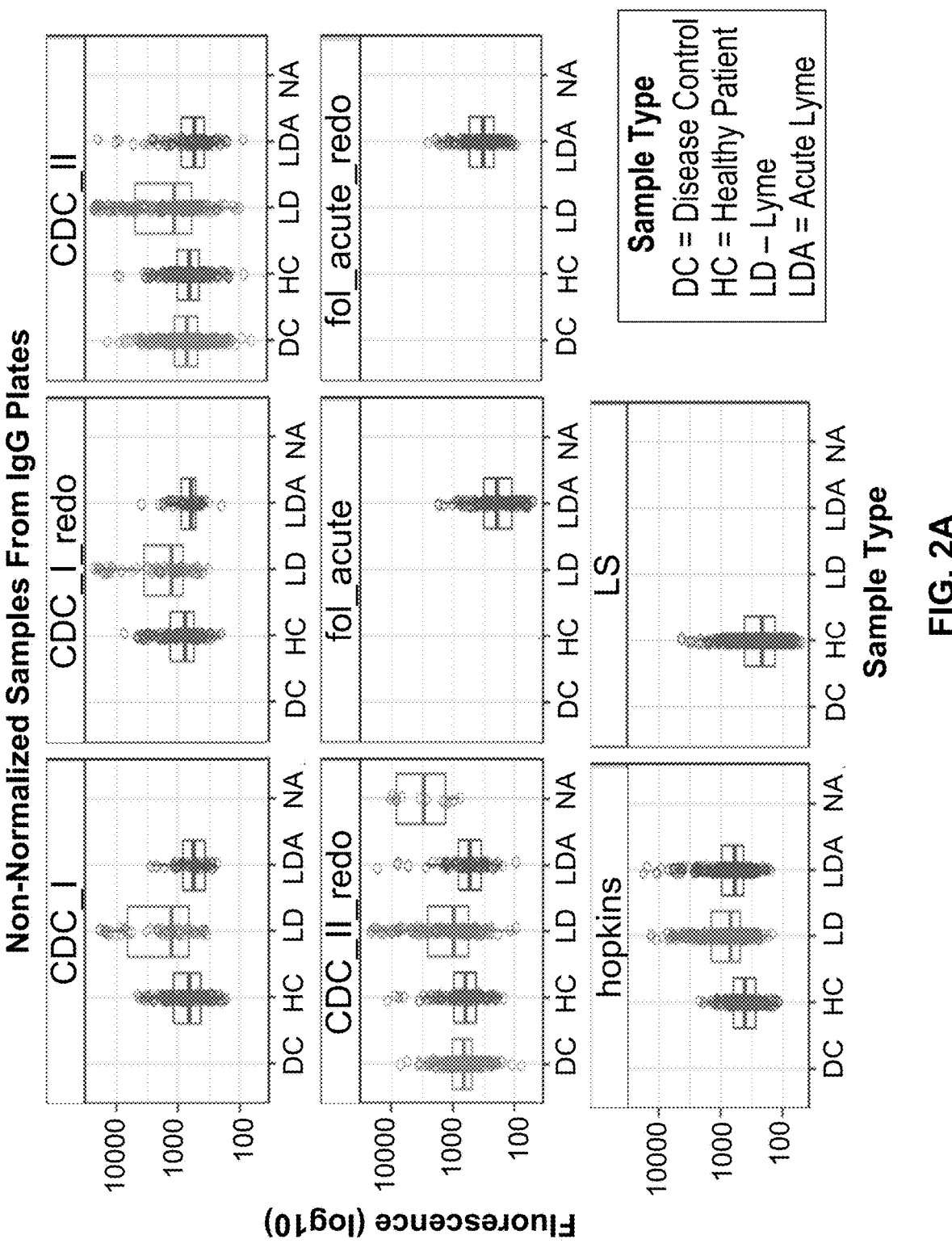
FIGS. 2A and 2B provide data showing fluorescence signals that are non-normalized from various sample types (disease/control patients, healthy patients, Lyme patients, and acute Lyme patients) from IgG plates (FIG. 2A) and IgM plates (FIG. 2B).
Figure 2B:
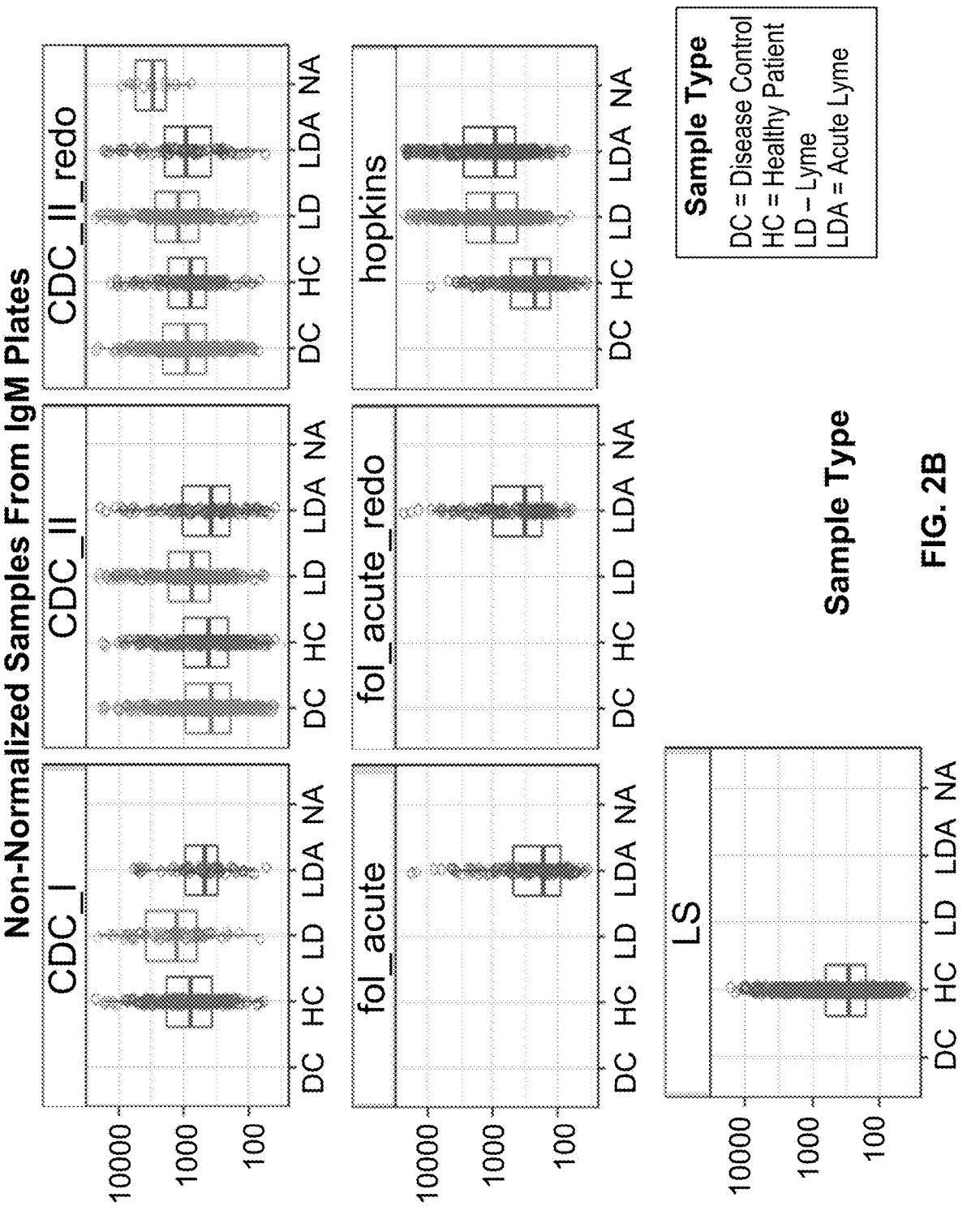
Figure 3A:
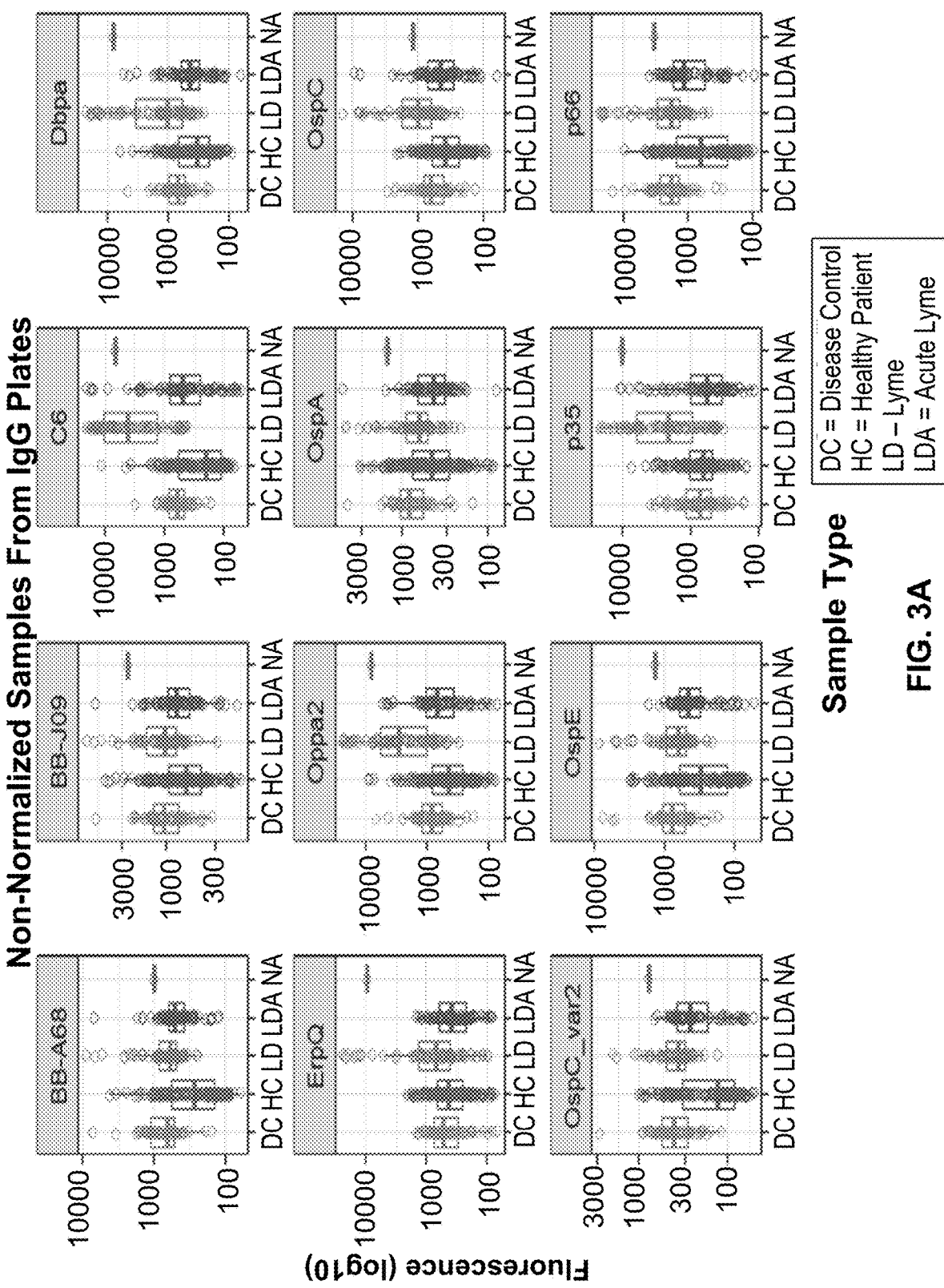
FIGS. 3A and 3B provide data showing fluorescence signals that are non-normalized testing various antigens from various sample types (disease/control patients, healthy patients, Lyme patients, and acute Lyme patients) from IgG plates (FIG. 3A) and IgM plates (FIG. 3B).
Figure 3B:
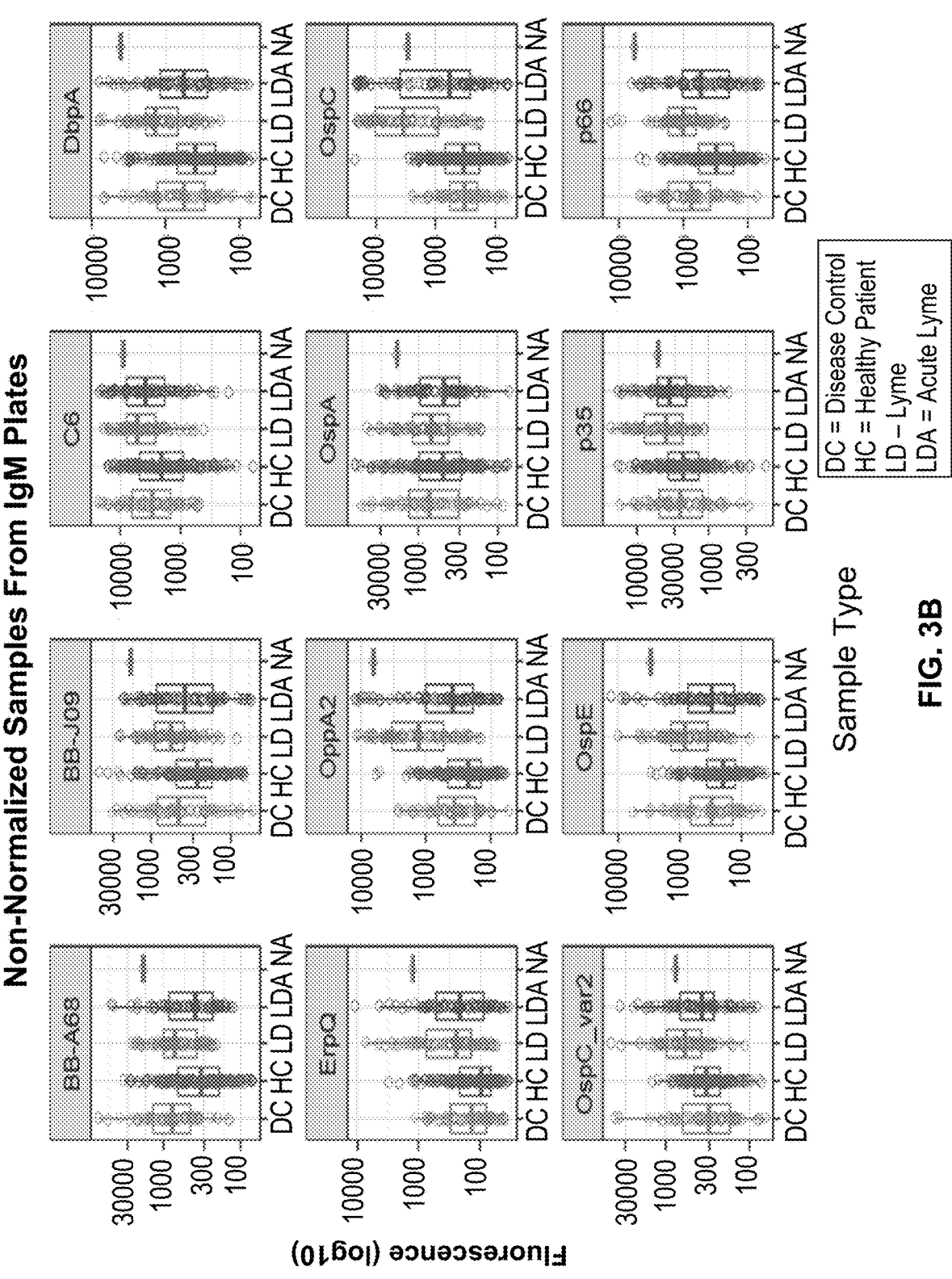
Figure 4A:
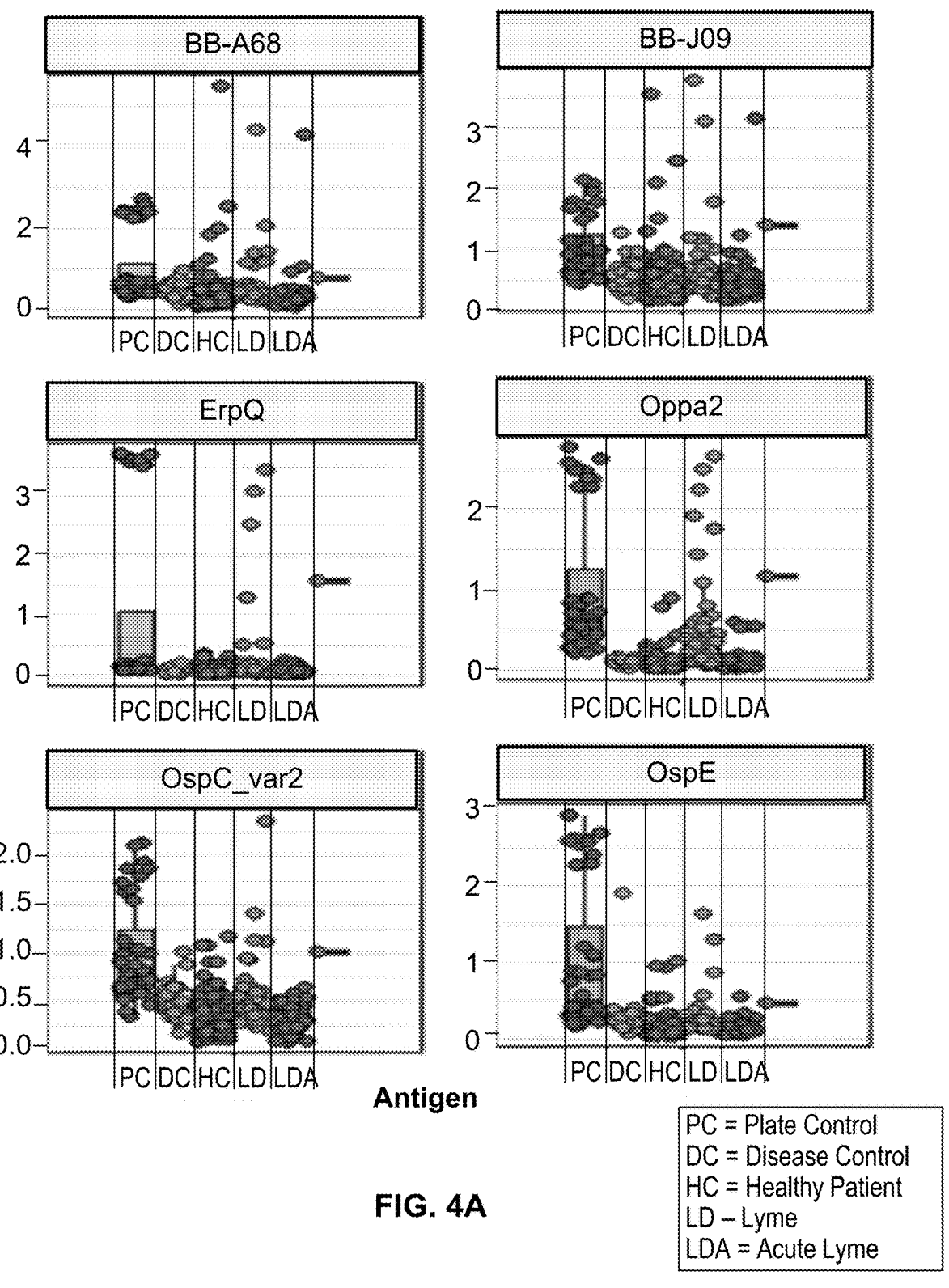
FIGS. 4A and 4B provide data showing fluorescence signals that are normalized testing various antigens from various sample types (disease/control patients, healthy patients, Lyme patients, and acute Lyme patients) from IgG plates (FIG. 4A) and IgM plates (FIG. 4B).
Figure 4A:
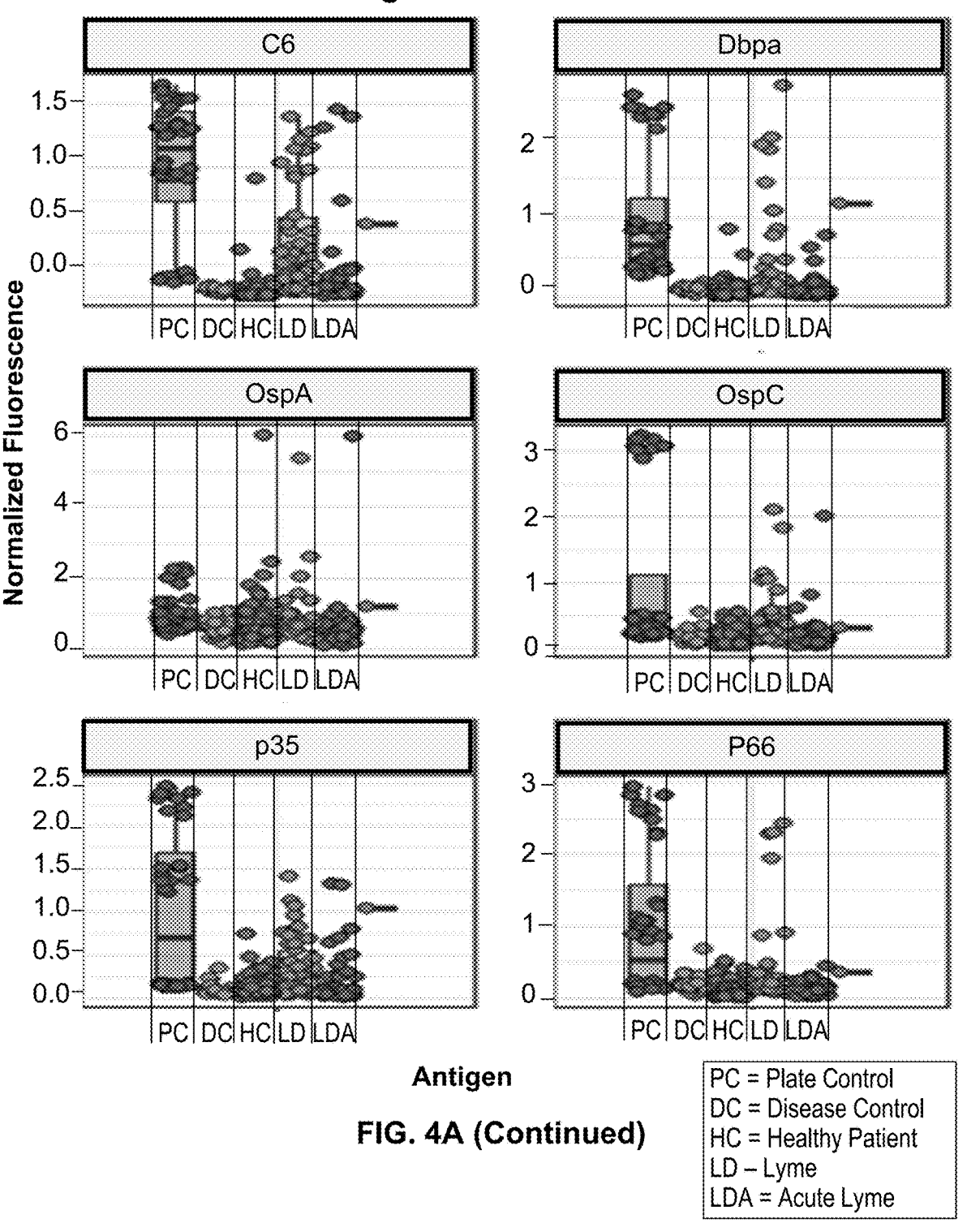
Figure 4B:
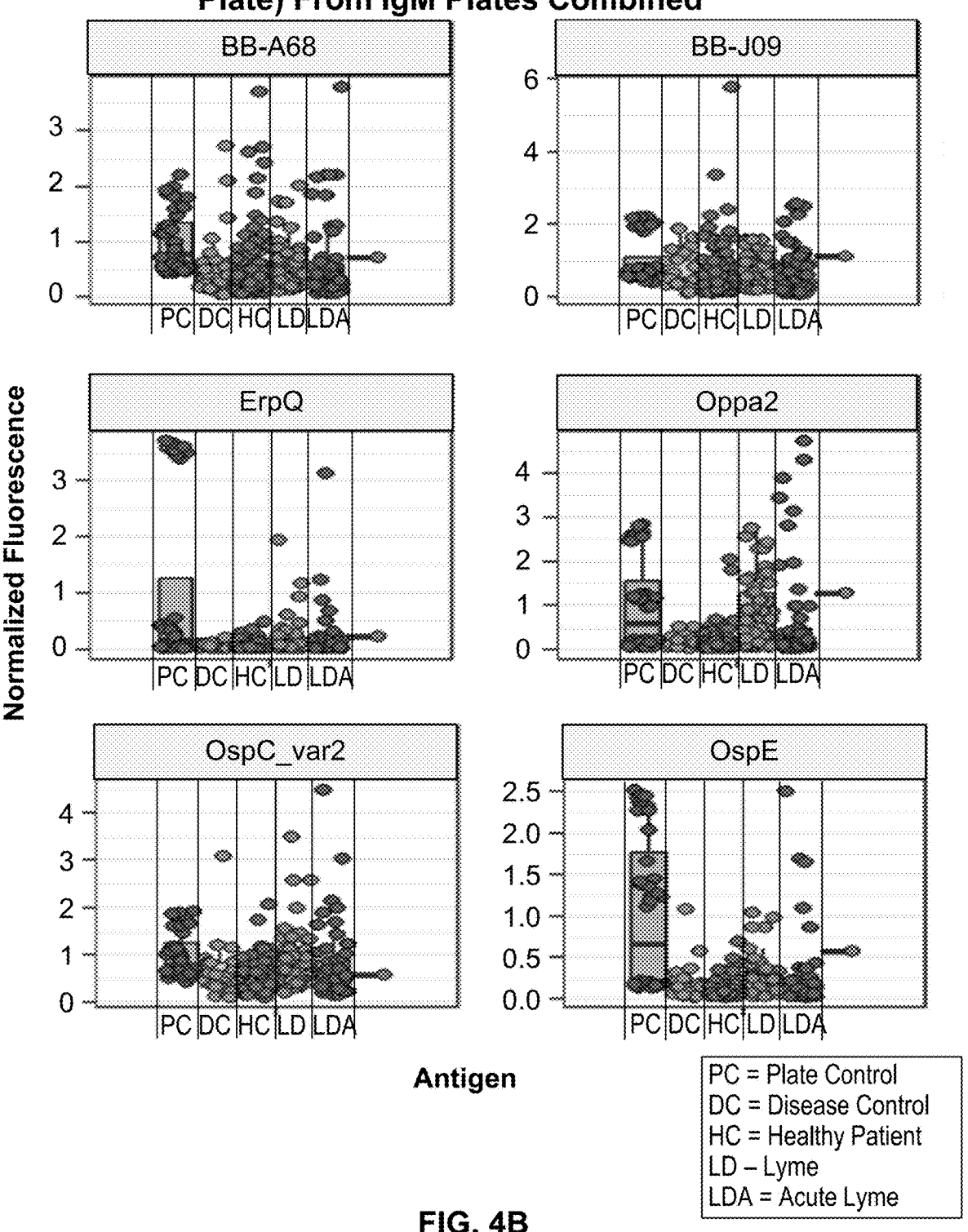
Figure 4B:
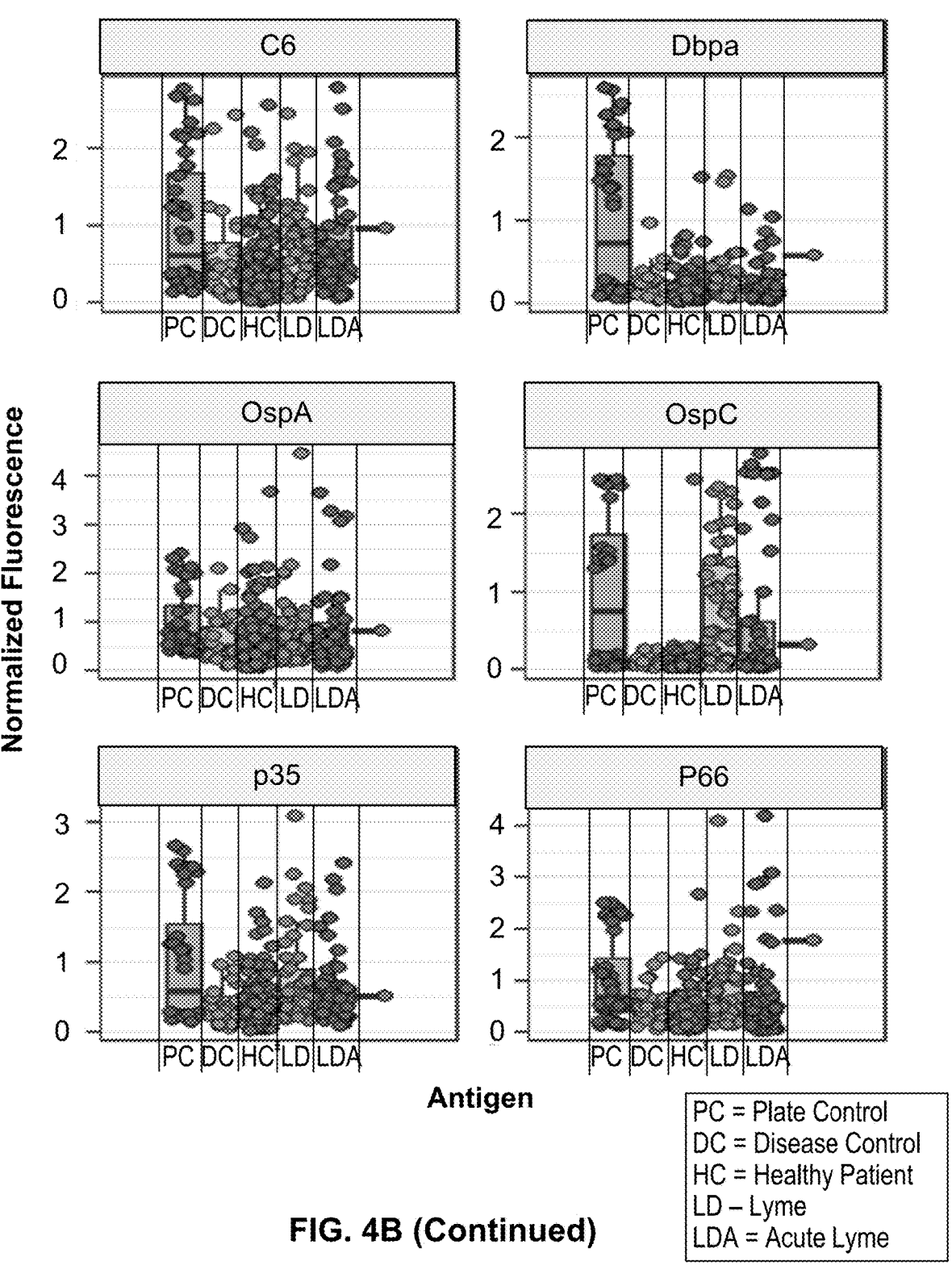
Figure 14A:
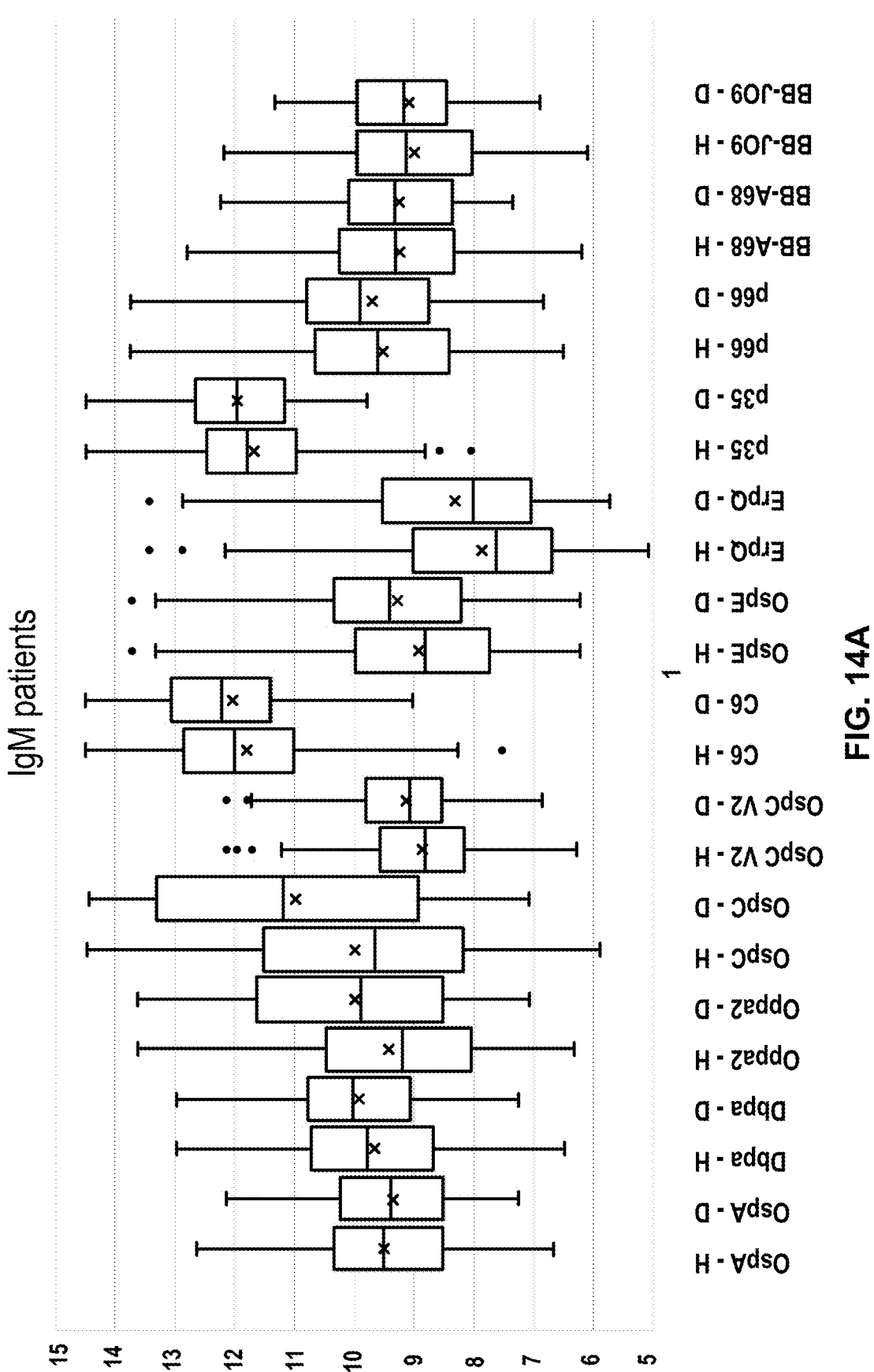
Figure 14B:
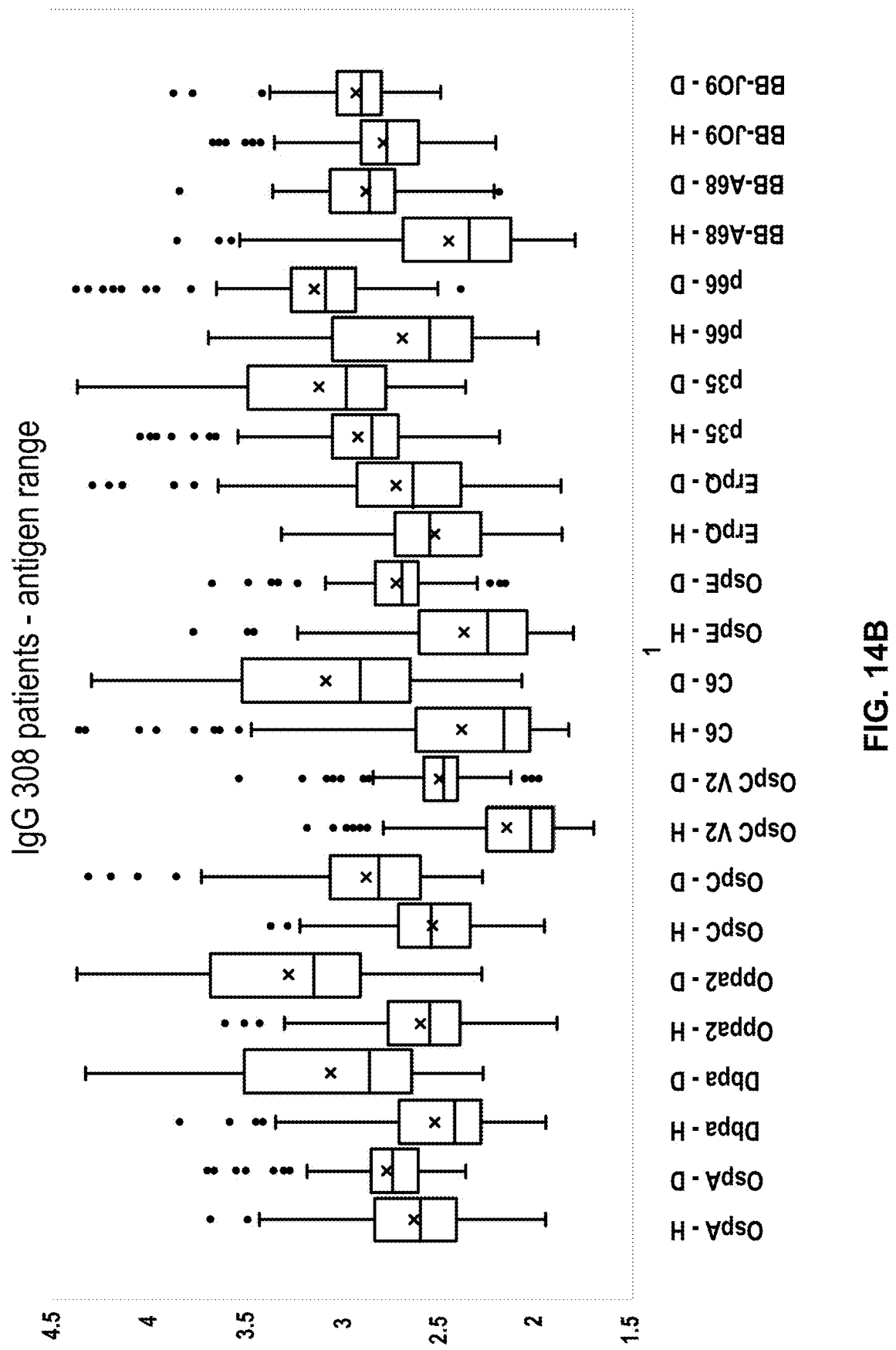

FIG. 14A-14B provide data showing the detected antigen range to make a positive call. FIG. 14A shows IgM data and FIG. 4B shows IgG data. This is the IgM/IgG range of values for each antigen. The distribution of data for healthy/Lyme patients is shown as pairs of boxplots, healthy first, then Lyme.

DETAILED DESCRIPTION

Disclosed herein are methods of detecting Lyme disease. In some embodiments, the methods detect Lyme disease in the early stages of the disease, for example, within two (2) weeks of receiving a tick bite. In some embodiments, the methods detect Lyme disease/Borreliosis across multiple *Borrelia burgdorferi* species. In some embodiments, the methods detect infection at different stages of Lyme disease.

In some embodiments, the methods of detecting Lyme disease disclosed herein include using any one or more of the antigens C6, GlpQ, p35, p66, OspC, DbpA, OppA2, ErpQ, OspE, and OspC2. Current tests are only 28% accurate Horn, J Clin Microbiol. 2020) in early Lyme disease, and less than 50% accurate overall (Cook, Int J Gen Med. 2016). Undiagnosed or misdiagnosed Lyme disease patients are at high risk for developing long term, debilitating illness. High treatment costs ($100 billion annually in the US and EU) are driven by undiagnosed or misdiagnosed patients developing Persistent Lyme Disease, which could be avoided with proper and early diagnosis (Johnson, LDo, 2018).

The global seroprevalence of Lyme disease is estimated at 14.5% (1.17 billion people) of the world's population (Dong, B M J Glob Health. 2022). In the US, Lyme disease is the most common vector borne disease (Kugeler, Emerg Infect Dis. 2021), and the third most common bacterial infection overall (CDC NNDSS). Lyme disease treatments cost healthcare payers $100 B annually in the US and EU (Hook Emer Infect Dis. 2022, Rgalska, Front Pub Health 2021).

The methods and compositions disclosed herein are over 90% accurate across all stages of disease. In some embodiments, the methods described herein are used to diagnose Lyme disease across all stages of disease. In some embodiments, the methods described herein are used to diagnose a patient having acute Lyme disease. In some embodiments, the methods described herein are used to diagnose a patient having post-treatment Lyme disease. In some embodiments, the methods described herein are used to diagnose a patient having early Lyme disease. In some embodiments, the methods described herein are used to diagnose a patient having early disseminated Lyme disease. In some embodiments, the methods described herein are used to diagnose a patient having late disseminated Lyme disease.

TERMS

Unless defined otherwise, all technical and scientific terms used herein have the same meaning as is commonly understood by one of ordinary skill in the art. As used herein, the term "comprising" is intended to mean that the compositions and methods include the recited elements, but not excluding others. "Consisting essentially of" when used to define compositions and methods, shall mean excluding other elements of any essential significance to the composition or method. "Consisting of" shall mean excluding more than trace elements of other ingredients for paragraph ed compositions and substantial method steps. The use of the term "including" as well as other forms, such as "include," "includes," and "included," is not limiting. The use of the term "having" as well as other forms, such as "have," "has," and "had," is not limiting.

The terms "substantially," "approximately," and "about" used throughout this specification are used to describe and account for small fluctuations, such as due to variations in processing. For example, they may refer to less than or equal to ±10%, such as less than or equal to ±5%, such as less than or equal to ±2%, such as less than or equal to ±1%, such as less than or equal to ±0.5%, such as less than or equal to ±0.2%, such as less than or equal to ±0.1%, such as less than or equal to ±0.05%.

As used herein, certain terms may have the following defined meanings. As used in the specification and paragraph s, the singular form "a," "an" and "the" include singular and plural references unless the context clearly dictates otherwise. For example, the term "a cell" includes a single cell as well as a plurality of cells, including mixtures thereof.

Throughout this application, various embodiments may be presented in a range format. It should be understood that the description in range format is merely for convenience and brevity and should not be construed as an inflexible limitation on the scope of the disclosure. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals there between.

All numerical designations, e.g., pH, temperature, time, concentration, and molecular weight, including ranges, are approximations which are varied (+) or (−) by increments of 0.1. It is to be understood, although not always explicitly stated that all numerical designations are preceded by the term "about". The term "about" also includes the exact value "X" in addition to minor increments of "X" such as "X+0.1" or "X−0.1." It also is to be understood, although not always explicitly stated, that the reagents described herein are merely exemplary and that equivalents of such are known in the art.

Unless otherwise defined, all technical and/or scientific terms used herein have the same meaning as commonly understood by one of ordinary skill in the art. Although methods and materials similar or equivalent to those described herein can be used in the practice or testing of embodiments disclosed herein, exemplary methods and/or materials are described below. In case of conflict, the patent specification, including definitions, will control. In addition, the materials, methods, and examples are illustrative only and are not intended to be necessarily limiting.

The terms "administration of" or "administering" should be understood to mean providing an active agent (e.g., an antibiotic) to the subject in need of treatment in a form that can be introduced into that individual's body in a therapeutically useful form and therapeutically effective amount.

As used herein, the term "antibody" refers to an antibody that specifically binds to an antigen or an antigenic fragment thereof.

Figure 5A:
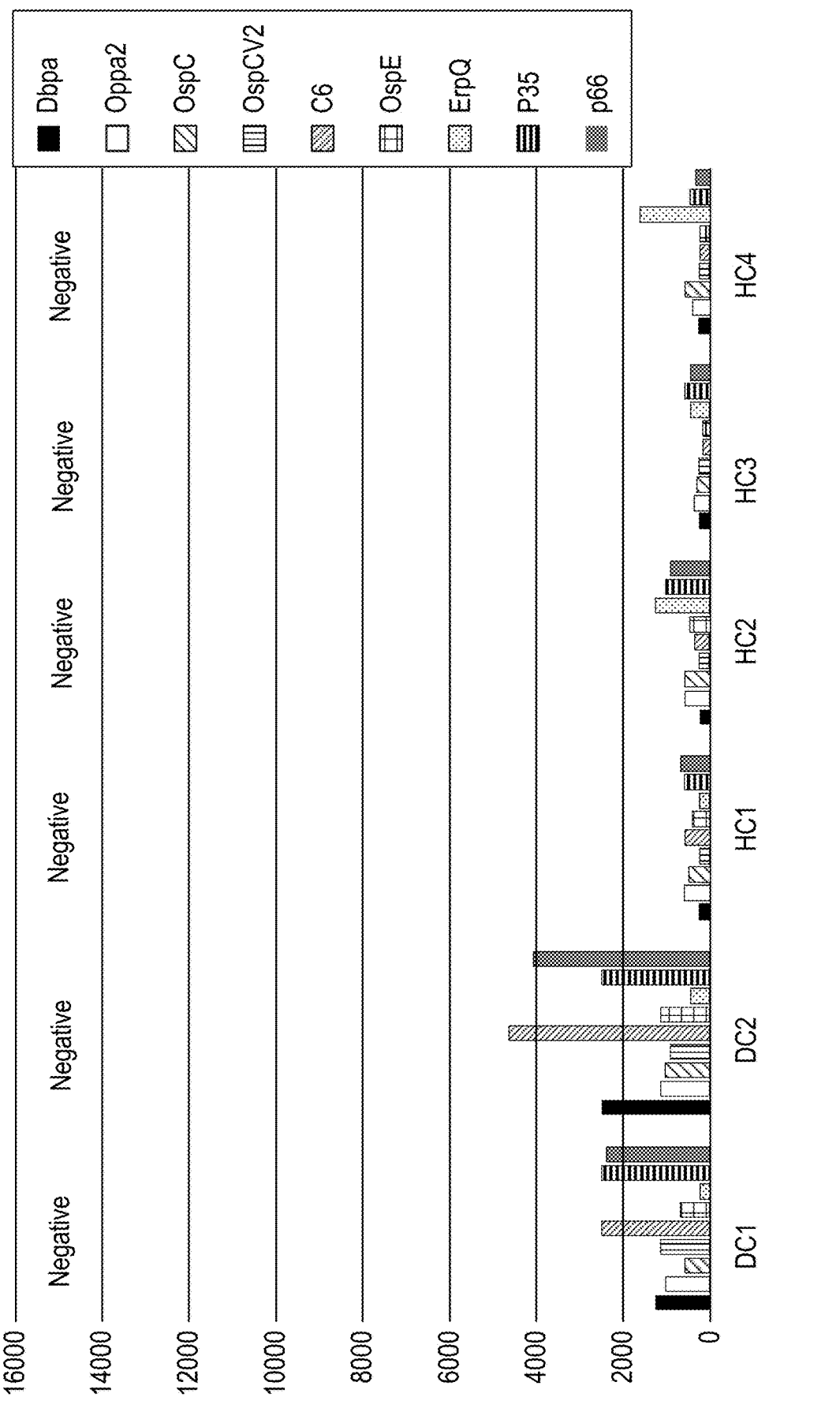
FIGS. 5A an 5B provide data showing fluorescence signals of non-Lyme vs. Lyme disease patients by antigen.
Figure 5A:
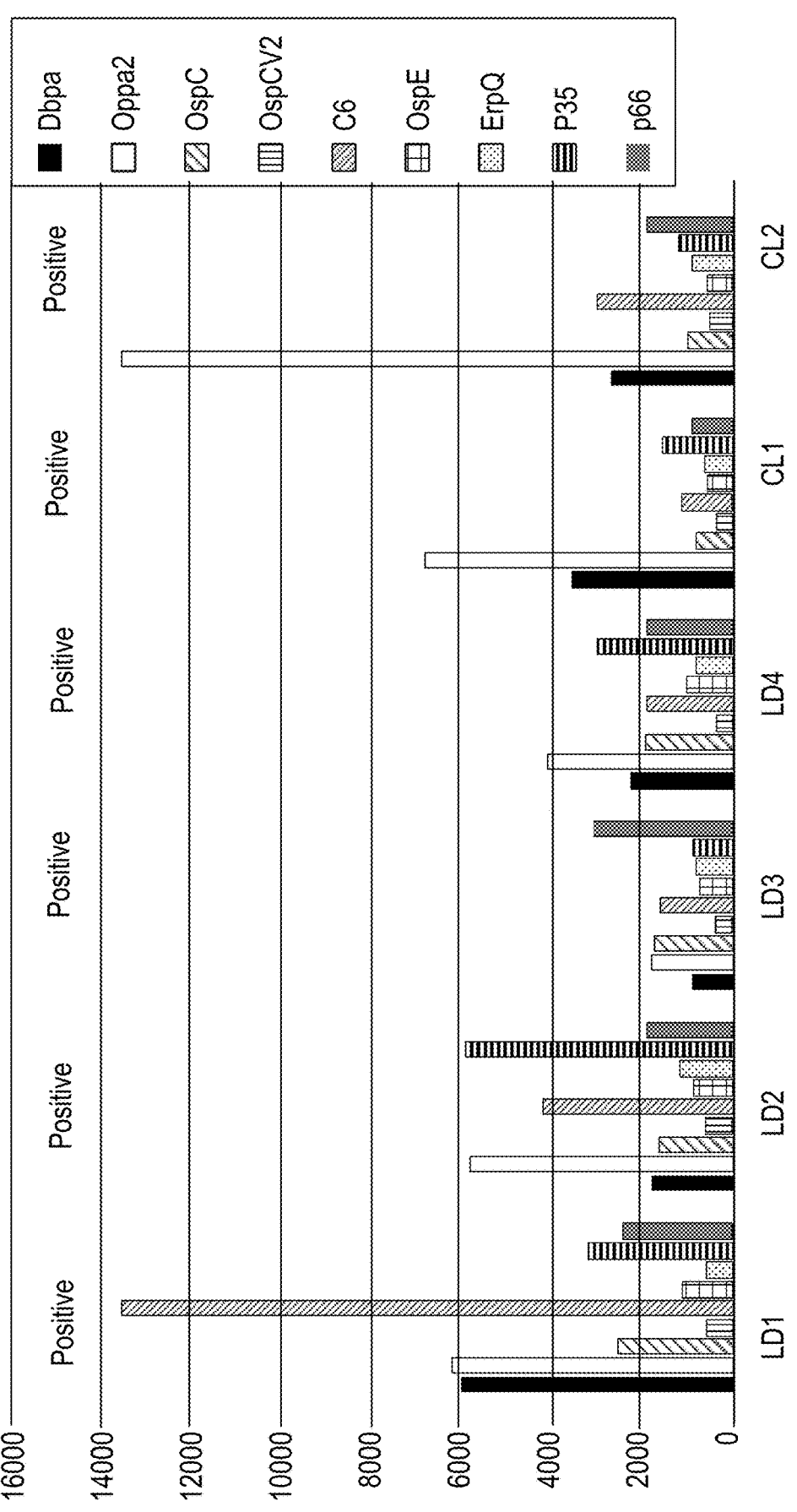
Figure 5B:
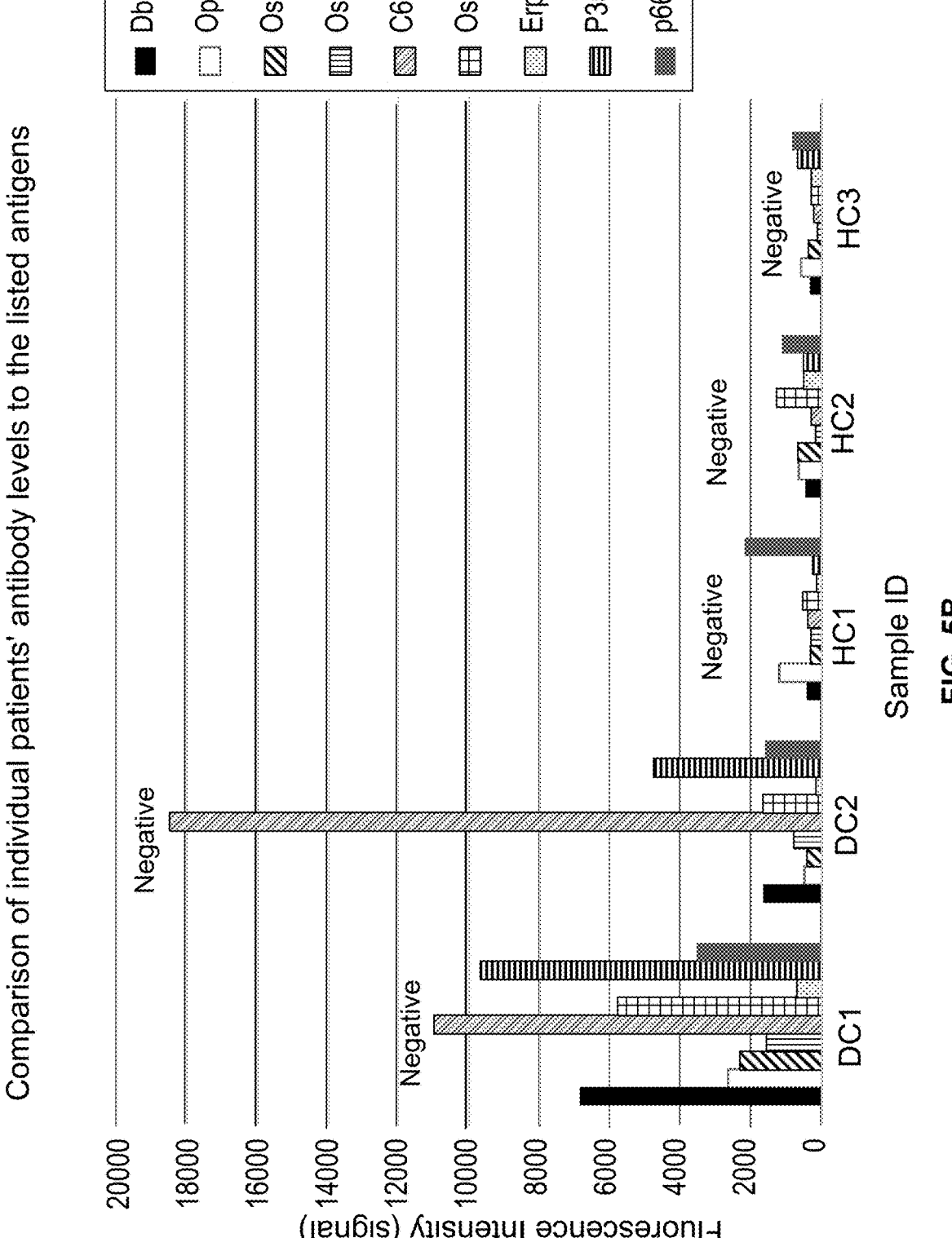
In FIG. 5B, a set of 5 non-disease and 5 disease patients is shown. DC1, DC2 are non-Lyme infected patients who have a similar febrile disease with symptoms similar to Lyme. HC1, HC2, and HC3 are healthy endemic controls. LD1, LD2, LD3 and LD4 are confirmed Lyme disease infected patients from 2 different cohorts, geographically separated. CL1 is a confirmed chronic Lyme patient. In 5A and 5B, the "negative" and "positive" annotations are the call made by the Lyme classifier described herein based on the data for each patient. Positive indicates a call that the patient has a Lyme infection.
Figure 5B:
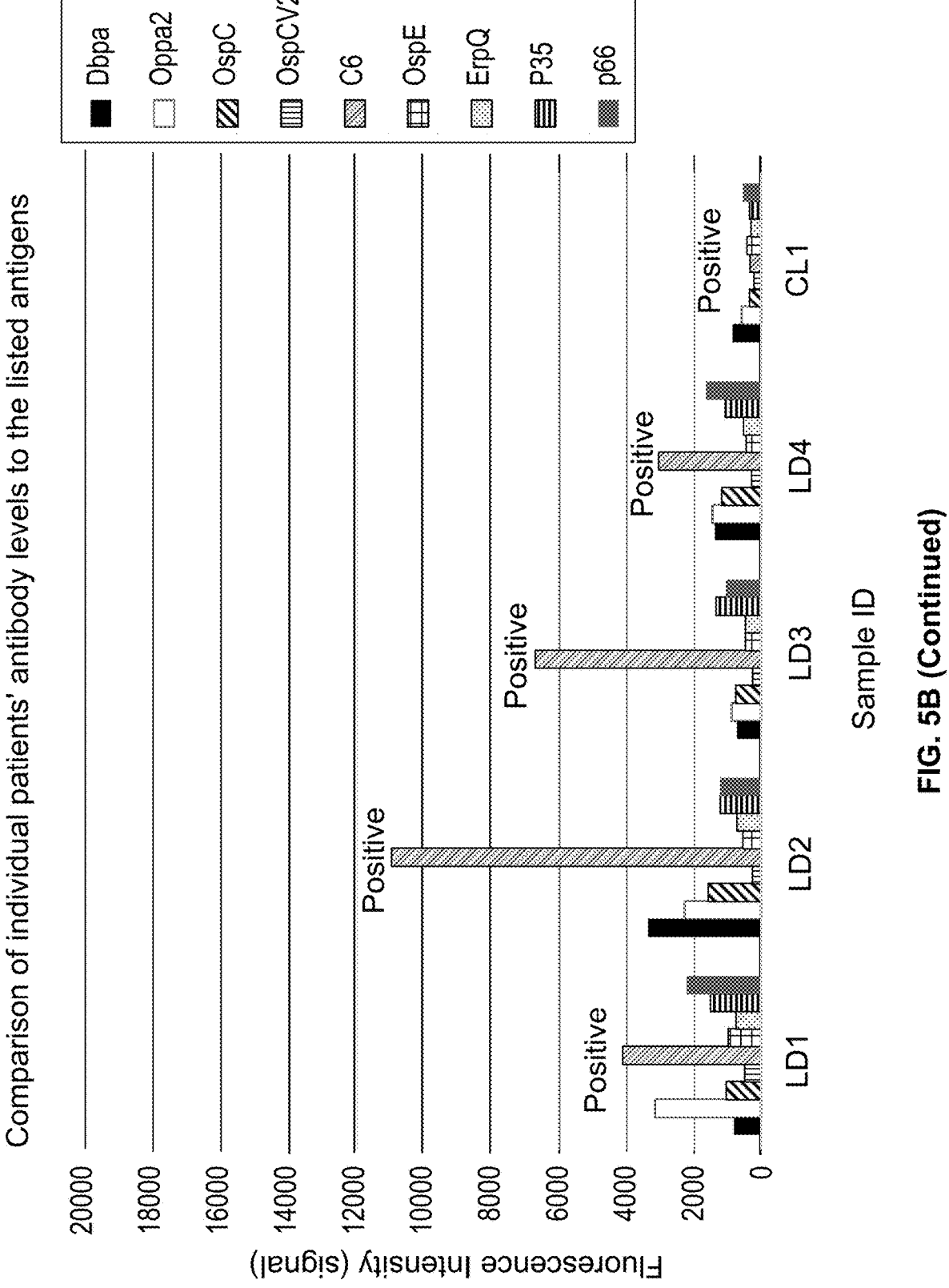

As used herein, the phrase "decision tree" refers to a way of classifying samples using at least one value that relates to the sample. Examples of values that relate to a sample includes expression values or fluorescence values of a protein or antigen, amongst others. Samples can be classified in a decision tree using discrete cutoff values or a range of cutoff values. In some embodiments, a decision tree classifies samples using more than one value. For example, the decision tree may classify samples based on the value of more than one antigen or protein. Examples of calls based on the decision trees are shown in FIGS. 5A and 5B.

As used herein, the phrase "confusion matrix" is a measure of the number of samples that were modeled correctly and incorrectly using a "decision tree." See FIG. 6.

As used herein, the term "biological sample" encompasses a variety of sample types obtained from an organism. The term encompasses bodily fluids such as blood, blood components, saliva, serum, plasma, cerebro-spinal fluid (CSF), urine and other liquid samples of biological origin, solid tissue biopsy, tissue cultures, or supernatant taken from cultured patient cells. In the context of the disclosure herein, the biological sample is typically a bodily fluid with detectable amounts of antibodies, e.g., blood or a blood component (e.g., plasma or serum) or CSF. The biological sample can be processed prior to assay, e.g., to remove cells or cellular debris. The term encompasses samples that have been manipulated after their procurement, such as by treatment with reagents, solubilization, sedimentation, or enrichment for certain components.

As used herein, the term "diagnosis" is intended to encompass determining the susceptibility of a subject to a certain disease or disorder, determining whether a subject is affected with a certain disease or disorder, determining the prognosis of a subject affected with a certain disease or disorder or therametrics (e.g., monitoring the state of a subject to provide information on therapeutic efficacy). Particularly, the diagnosis, as used herein, means the determination of whether the patient has (onset) or the possibility of onset (risk) of Lyme Disease.

The term "individual," "subject," or "patient" typically refers to humans, but also to other animals including, e.g., other primates, rodents, canines, felines, equines, ovines, porcines, and the like.

As used herein, the term "OspA" refers to either the gene that encodes the protein outer surface protein A or the protein outer surface protein A.

As used herein, the term "DbpA" refers to either the gene that encodes the protein decorin-binding protein A or the protein decorin-binding protein A.

As used herein, the term "OppA2" refers to either the gene that encodes the protein periplasmic oligopeptide binding protein or the protein periplasmic oligopeptide binding protein.

As used herein, the term "OspC" refers to either the gene that encodes the protein outer surface protein C or the protein outer surface protein C.

As used herein, the term "C6" refers to either the invariable region 6 of the vlsE gene that encodes the protein VlsE or the 26-amino acid peptide within the VlsE protein.

As used herein, the term "OspE" refers to either the gene that encodes the protein outer surface protein E or the protein outer surface protein E.

As used herein, the term "ErpQ" or "ElpQ" refers to either the gene that encodes the protein exported repeated protein Q or the protein exported repeated protein Q.

As used herein, the term "p35" refers to either the gene that encodes the protein p35 or the protein p35.

As used herein, the term "p66" refers to either the gene that encodes the porin protein p66 or the protein p66.

As used herein, the term "BBA68" refers to either the gene that encodes the protein BBA68 (BbCRASP-1) or the protein BBA68 (BbCRASP-1).

As used herein, the term "BBJ09" refers to either the gene that encodes the protein BBJ09 or the protein BBJ09.

As used herein, the term "IgM" refers to either the gene that encodes the protein immunoglobulin M or the protein immunoglobulin M.

As used herein, the term "IgG" refers to either the gene that encodes the protein immunoglobulin G or the protein immunoglobulin G.

As used herein, the term "Lyme disease" refers to a disease that is caused by a bacterial species, typically, the bacterium *Borrelia burgdorferi*. Typically, Lyme disease is transmitted through a tick bite. As used herein the term Lyme Disease refers to early Lyme disease, early disseminated Lyme disease, and late disseminated Lyme disease, Acute Lyme Disease and/or Post-Treatment Lyme Disease.

As used herein, the term "early Lyme disease" refers to a stage of Lyme Disease in which the bacteria are localized and has not spread throughout the body.

As used herein, the term "early disseminated Lyme disease" refers to a stage of Lyme Disease in which the bacteria have begun to spread throughout the body.

As used herein, the term "late disseminated Lyme disease" refers to a stage of Lyme Disease in which the bacteria have completed their spread throughout the body.

As used herein, the term "Acute Lyme Disease" refers to a stage of Lyme disease after the initial infection that occurs after a tick bite. This initial infection can occur between hours after the tick bite and days after the tick bite. The term Acute Lyme Disease means less than 14 days post-tick bite. During the stage of Acute Lyme Disease, the infection has not spread throughout the body.

As used herein, the term Post-Treatment Lyme Disease" refers to a stage of Lyme Disease characterized by certain symptoms that persist despite being treated for Lyme disease. In some embodiments, these symptoms include, but are not limited to, fatigue, pain, and cognitive impairment.

The term "classifying" includes "to associate" or "to categorize" a sample with a disease state. In certain instances, "classifying" is based on statistical evidence, empirical evidence, or both. In certain embodiments, the methods and systems of classifying use a so-called training set of samples having known disease states. Once established, the training data set serves as a basis, model, or template against which the features of an unknown sample are compared, in order to classify the unknown disease state of the sample. In certain instances, classifying the sample is akin to diagnosing the disease state of the sample. In certain other instances, classifying the sample is akin to differentiating the disease state of the sample from another disease state.

The terms "complex," "immuno-complex," "conjugate," and "immunoconjugate" include, but are not limited to, peptide or antigen bound (e.g., by non-covalent means) to an antibody or an antibody fragment.

The term "monitoring the progression or regression of Lyme disease" includes the use of the methods and systems to determine the disease state (e.g., presence or severity of Lyme disease) of an individual. In some embodiments, the methods and systems disclosed herein can be used to predict the progression of Lyme disease, e.g., by determining a likelihood for Lyme disease to progress either rapidly or slowly in an individual based on an analysis of diagnostic markers and/or the identification or Lyme disease-related symptoms. In other embodiments, the methods and systems disclosed herein can be used to predict the regression of Lyme disease, e.g., by determining a likelihood for Lyme disease to regress either rapidly or slowly in an individual based on an analysis of diagnostic markers and/or the identification or Lyme disease-related symptoms.

The term "antibody marker profile" includes 1, 2, 3, 4, 5, 6, 7, 8, 9, 10, 11, 12, or more marker(s) of an individual, wherein the marker(s) can be an antibody marker, such as, but not limited to, an antibody that recognizes (e.g., specifically bind to, forms a complex) with an antigen, such as C6, GlpQ, p35, p66, OspC, DbpA, OppA2, ErpQ, OspE, and OspC2 and the like. A statistical analysis can transform the level of the antibody marker(s) into an antigen antibody marker profile. In some instances, a statistical analysis is a quartile score and the quartile score for each of the markers can be summed to generate a quartile sum score. In one aspect, a statistical process comprising, consisting of, or consisting essentially of a single learning statistical classifier system is applied to the data set of the antibody marker profile to produce a statistically derived decision classifying a sample as a Lyme disease sample or a non-Lyme disease sample (e.g., healthy control sample) based upon the antibody marker profile, wherein the antibody marker profile indicates the level of at least one antibody marker.

While some embodiments comprise/include the disclosed features and may therefore include additional features not specifically described, other embodiments may be essentially free of or completely free of non-disclosed elements— that is, non-disclosed elements may optionally be essentially omitted or completely omitted.

Before explaining at least one embodiment in detail, it is to be understood that the disclosure is not necessarily limited in its application to the details set forth in the following description or exemplified by the Examples. The disclosure is capable of other embodiments or of being practiced or carried out in various ways.

"Reagent" means a substance or mixture to carry out a laboratory test.

"Binding molecule" includes antibodies, both monoclonal and polyclonal, aptamers and the like. An appropriate binding molecule will bind specifically to an analyte, in other words, it reacts at a detectable level with the analyte but does not react detectably (or reacts with limited cross-reactivity) with other or unrelated analytes.

Methods of Detecting Lyme Disease and Treating Lyme Disease

In an aspect, a method of diagnosing Lyme disease is provided, the method includes detecting reactivity levels of an antibody in a patient sample to any one or more of the following antigens: C6, GlpQ, p35, p66, OspC, DbpA, OppA2, ErpQ, OspE, and OspC2 or variants thereof.

In one aspect, disclosed are methods and assays to aid in the diagnosis of Lyme disease based on the presence or level of certain antibody markers, alone or in combination in a patient sample. In certain embodiments, these methods and assays are related to the detection of the presence and level of various Lyme disease biomarkers in the blood and/or serum of subjects. In some embodiments, the method comprises the detection of at least one antibody against a bacterial antigen (e.g., C6, GlpQ, p35, p66, OspC, DbpA, OppA2, ErpQ, OspE, and OspC2, or combination thereof or variants thereof) in a blood and/or serum sample from a subject.

In some embodiments, the method of diagnosing Lyme disease includes detecting binding between one or more antibodies to any one or more of the following antigens C6, GlpQ, p35, p66, OspC, DbpA, OppA2, ErpQ, OspE, and OspC2 or variants thereof in a biological sample. In some embodiments, the one or more antibodies includes IgM. In some embodiments, the one or more antibodies includes IgG. In some embodiments, the one or more antibodies includes IgM and IgG. According to some embodiments, the reactivity of the antibodies comprises increased IgG, IgM, and IgG and IGM reactivities compared to a control or threshold.

In some embodiments, detecting binding between one or more antibodies to any one of the following antigens: C6, GlpQ, p35, p66, OspC, DbpA, OppA2, ErpQ, OspE, and OspC2 comprises detecting fluorescence of the one or more antibodies bound to the antigens.

In some embodiments, IgM binds to each of the antigens of C6, GlpQ, p35, p66, OspC, DbpA, OppA2, ErpQ, OspE, and OspC2; or C6, OspC, and OspC2; or C6, and OspC2; or C6, and OspC; or OspC, and OspC2. In some embodiments, when the sum of the IgM bound to each of these antigens (C6, GlpQ, p35, p66, OspC, DbpA, OppA2, ErpQ, OspE, and OspC2) is greater than or equal to 850, the sample is diagnosed has having Lyme disease. For example the sample is diagnosed as having Lyme disease when the sum of the fluorescence values of IgM bound to the antigens is at least 850, at least 860, at least 870, at least 880, at least 890, at least 900, at least 910, at least 920, at least 930, at least 940, at least 950, at least 960, at least 970, at least 980, at least 990, or at least 1000. In some embodiments, when the sum of the fluorescence values of IgM bound to the antigens is about 899 or greater, the sample is diagnosed as having Lyme disease. In some embodiments, for example the sample is diagnosed as having Lyme disease when the sum of the fluorescence values of IgM bound to the antigens is 899-1000.

In some embodiments, IgG binds to each of the antigens of C6, GlpQ, p35, p66, OspC, DbpA, OppA2, ErpQ, OspE, and OspC2; or C6, OspC, and OspC2; or C6, and OspC2; or C6, and OspC; or OspC, and OspC2. In some embodiments, when the sum of the IgG bound to each of these antigens (C6, GlpQ, p35, p66, OspC, DbpA, OppA2, ErpQ, OspE, and OspC2) is greater than or equal to 5850, the sample is diagnosed has having Lyme disease. For example the sample is diagnosed as having Lyme disease when the sum of the fluorescence values of IgG bound to the antigens is at least 5850, at least 5860, at least 5870, at least 5880, at least 5890, at least 5900, at least 5910, at least 5920, at least 5930, at least 5940, at least 5950, at least 5960, at least 5970, at least 5980, at least 5990, at least 6000, at least 6010, at least 6020, at least 6030, at least 6040, at least 6050, at least 6060, at least 6070, at least 6080, at least 6090, or at least 7000. In some embodiments, when the sum of fluorescence values of IgG bound to the antigens is about 5955 or greater, the sample is diagnosed as having Lyme disease. In some embodiments, for example the sample is diagnosed as having Lyme disease when the sum of the fluorescence values of IgG bound to the antigens is 5955-7000.

In some embodiments, the method of diagnosing Lyme disease includes detecting binding between one or more antibodies to any one or more of the following antigens C6, GlpQ, p35, p66, OspC, DbpA, OppA2, ErpQ, OspE, and OspC2 or variants thereof in a biological sample. In some embodiments, the one or more antibodies includes IgM. In some embodiments, the one or more antibodies includes IgG. In some embodiments, the one or more antibodies includes IgM and IgG. In some embodiments, the one or more antibodies includes IgM or IgG.

In some embodiments, IgM from a patient sample binds to one or more of the antigens C6, GlpQ, p35, p66, OspC, DbpA, OppA2, ErpQ, OspE, and OspC2. In some embodiments, IgM from a patient sample binds to each of the antigens C6, GlpQ, p35, p66, OspC, DbpA, OppA2, OspE, and OspC2; or C6, OspC, and OspC2; or C6, and OspC2; or C6, and OspC; or OspC, and OspC2. In some embodiments, IgG from a patient sample binds to one or more of the antigens C6, GlpQ, p35, p66, OspC, DbpA, OppA2, ErpQ, OspE, and OspC2. In some embodiments, IgG from a patient sample binds to each of the antigens C6, GlpQ, p35, p66, OspC, DbpA, OppA2, ErpQ, OspE, and OspC2; or C6, OspC, and OspC2; or C6, and OspC2; or C6, and OspC; or OspC, and OspC2.

In some embodiments, the method of diagnosing Lyme disease includes detecting binding between one or more antibodies to any one or more of the following antigens C6, GlpQ, p35, p66, OspC, DbpA, OppA2, ErpQ, OspE, and OspC2; or C6, OspC, and OspC2; or C6, and OspC2; or C6, and OspC; or OspC, and OspC2 or variants thereof in a sample and classifying the sample using a decision tree. In some embodiments, the one or more antibodies comprise, consist of, or consist essentially of IgM to make a diagnostic call. In some embodiments, the one or more antibodies comprise, consist of, or consist essentially of IgG to make a diagnostic call. In some embodiments, the one or more antibodies includes IgM and IgG to make a diagnostic call. In some embodiments, the one or more antibodies includes IgM or IgG to make a diagnostic call. See FIGS. 5A and 5B.

In some embodiments, the method includes exposing *Borrelia* antigens to a biological sample. In some embodiments, the biological sample derives from a subject that has Lyme disease. In some embodiments, the subject has any form of Lyme disease described herein such as, for example, any one or more of early Lyme disease, early disseminated Lyme disease, late disseminated Lyme disease, acute Lyme disease, and post-treatment Lyme disease. In some embodiments, the biological sample derives from a subject that is suspected of having Lyme disease. In some embodiments, the subject is suspected of having any form of the forms of Lyme disease described herein such as, for example, any one or more of early Lyme disease, early disseminated Lyme disease, late disseminated Lyme disease, acute Lyme disease, and post-treatment Lyme disease.

In some examples, exposing *Borrelia* antigens to a biological sample results in binding of antibodies to antigens. In some embodiments, the antibodies do not bind to the antigen OspA. In some embodiments, binding of the antibodies to the antigen ErpQ is not assessed. In some embodiments, binding of the antibodies to the antigen BBJ09 is not assessed. In some embodiments, binding of the antibodies to the antigen BB-A68 is not assessed. In some embodiments, binding of the antibodies to the antigens OspA; ErpQ; BBJ09; and BB-A68 is not assessed. In some embodiments, GlpQ is not assessed.

In some embodiments, antibodies bind to any one or more of the following antigens: C6, GlpQ, p35, p66, OspC, DbpA, OppA2, ErpQ, OspE, and OspC2. In some embodiments, the antibodies bound to any one or more of C6, GlpQ, p35, p66, OspC, DbpA, OppA2, ErpQ, OspE, and OspC2; or C6, OspC, and OspC2 comprises IgM, IgG, or both IgM and IgG.

In some embodiments, antibodies to the following antigens are not assessed: OspA, BB-A68 and BBJ09. In some embodiments, GlpQ is not assessed.

In some embodiments, antibodies bind to any one or more of the following antigens: C6, GlpQ, p35, p66, OspC, DbpA, OppA2, ErpQ, OspE, and OspC2 but the sample is nevertheless diagnosed as not having Lyme disease.

In some embodiments, any one or more of the antibodies of the antibody/antigen interactions are detected and quantified. Detection of the any one or more antibodies can be performed through any technique known in the art for detecting and quantifying antibodies of antibody/antigen interactions. In some embodiments, any one or more of the antibodies of the antibody/antigen interactions are exposed to any one or more of IgM and IgG antibodies. In some embodiments, the any one or more of IgM and IgG antibodies bind to the any one or more of the antibodies of the antibody/antigen interactions. In some embodiments, the IgM and the IgG antibodies are attached to one or more fluorophores. In some embodiments, detecting the one or more fluorophores detects and quantifies the any one or more antibodies of the antibody/antigen interactions.

In some embodiments, detection of any one or more of C6, GlpQ, p35, p66, OspC, DbpA, OppA2, ErpQ, OspE, and OspC2 or variants thereof includes binding of the amino acid sequence or a portion of the amino acid sequence of C6, GlpQ, p35, p66, OspC, DbpA, OppA2, ErpQ, OspE, and OspC2 or variants thereof to a molecule, and detecting the molecule. In some embodiments, the molecule is a protein. In some embodiments, the protein is an antibody.

In some embodiments, binding of antibodies to any one or more of C6, GlpQ, p35, p66, OspC, DbpA, OppA2, ErpQ, OspE, and OspC2 or variants thereof produces a signal. In some embodiments, detection of the signal is used to determine the expression levels of the any one or more of C6, GlpQ, p35, p66, OspC, DbpA, OppA2, ErpQ, OspE, and OspC2 or variants thereof in the sample. In some embodiments, the signal includes a fluorescence signal. In some embodiments, detection of the fluorescence signal is used to determine the expression levels of the any one or more of C6, GlpQ, p35, p66, OspC, DbpA, OppA2, ErpQ, OspE, and OspC2 or variants thereof in the sample.

In an aspect, a method is provided including classifying a sample using at least one signal from any one or more of C6, GlpQ, p35, p66, OspC, DbpA, OppA2, ErpQ, OspE, and OspC2 or variants thereof. In some embodiments, the at least one signal is at least one fluorescence signal. In some examples, the at least one fluorescence signal is produced as a result of binding of the any one or more of C6, GlpQ, p35, p66, OspC, DbpA, OppA2, ErpQ, OspE, and OspC2 or variants thereof to at least one antibody.

In some embodiments, the at least one signal from any one or more of C6, GlpQ, p35, p66, OspC, DbpA, OppA2, ErpQ, OspE, and OspC2 or variants thereof is used to classify the sample using at least one decision tree.

Any of the methods of detecting Lyme disease described herein can be used to classify/diagnose any one or more of early Lyme disease, early disseminated Lyme disease, late disseminated Lyme disease, acute Lyme disease, and post-treatment Lyme disease.

Methods for Aiding in the Diagnosis of Lyme Disease

In one aspect, disclosed are methods for aiding in the diagnosis of Lyme Disease in a subject. In one instance, the method comprises: measuring the level of an array of antibody markers in a biological sample taken from the subject; applying a statistical analysis to the measured level of the array of antibody markers to generate an antigen antibody profile; and comparing the antigen antibody profile to a diagnostic model to determine whether the individual has an increased likelihood of having Lyme disease compared to being a healthy control.

In some embodiments, the array of antibody markers is detected by forming a complex with antigens selected form from the group consisting of: C6, GlpQ, p35, p66, OspC, DbpA, OppA2, ErpQ, OspE, and OspC2 and combinations thereof.

In some embodiments, the step of measuring the level of an array of antibody markers comprises: contacting the sample with at least one antigen or antigen fragment thereof to transform the antibody present in the sample into a complex comprising, consisting of, or consisting essentially of at least one antibody or antibody fragment thereof and the antigen or antigen fragment thereof, and detecting the complex which correlates to the level of at least one antigen antibody marker.

In some embodiments, the statistical analysis transforms the level of the array of antibody markers into an antigen antibody marker profile.

In some embodiments, the antibody marker profile includes an empirically derived profile that is based upon an analysis of a plurality of antibody markers. In one aspect, the concentration of markers or their measured concentration values are transformed into an index by an algorithm resident on a computer. In certain aspects, the profile is a synthetic or human derived output, score, or cut off value(s), which expresses the biological data in numerical terms. The profile can be used to determine or make or aid in making a clinical decision. An antibody marker profile can be measured multiple times over the course of time. In one aspect, the algorithm can be trained with known samples and thereafter validated with samples of known identity.

In some embodiments, the method comprises measuring the level of an array of antibody markers in a biological sample taken from the subject. In some embodiments, the level of at least one antibody marker is increased in an individual with Lyme disease compared to a healthy control. In other embodiments, the level of at least one antibody marker is decreased in an individual with Lyme disease compared to a healthy control. In some embodiments, the level of an array of antigen antibody markers is dysregulated in a sample taken from an individual with Lyme disease compared to one from a healthy control.

In some embodiments, the diagnostic model is established using a retrospective cohort with known Lyme disease and healthy controls.

In some embodiments, the antigen antibody model is derived by applying logistic regression analysis to the level of one or more antigen antibody marker determined in the retrospective cohort.

In one aspect, disclosed are methods for aiding in the diagnosis of Lyme disease in a subject. In some instances, the method comprises: (a) contacting a biological sample from the subject with an antigen antibody-binding moiety (e.g., an antigen or antigenic fragment thereof) under conditions suitable to transform the antibody present in the sample into a complex comprising, consisting of, or consisting essentially of the antibody and the antigen antibody-binding moiety and determining the level of the complex, thereby determining the level of the antibody present in the sample.

In some embodiments, the method further comprises comparing the level of the antibody present in the sample and/or antigen antibody complex generated from contacting the sample to the antigen antibody-binding moiety to a control level of antibody, wherein the level of antibody is indicative of an increased likelihood of the subject having Lyme disease.

In some embodiments, the control level of the antibody is the level of the antibody in a sample from a healthy control subject.

In some embodiments, the method for aiding in the diagnosis of Lyme disease in a subject comprise determining the level of at least one antibody marker that forms an antibody/antigen complex with C6, GlpQ, p35, p66, OspC, DbpA, OppA2, ErpQ, OspE, or OspC2 or combinations thereof.

In some embodiments, the method for aiding in the diagnosis of Lyme disease in a subject comprise determining the level of at least two antibody markers, wherein the first antibody marker is selected from the group consisting of antibodies capable of binding C6, GlpQ, p35, p66, OspC, DbpA, OppA2, ErpQ, OspE, or OspC2 and combinations thereof and wherein the second antibody marker is selected from the group consisting of antibodies capable of binding C6, GlpQ, p35, p66, OspC, DbpA, OppA2, ErpQ, OspE, or OspC2 and combinations thereof and wherein the first antibody marker and second antibody marker are different.

In some embodiments, the method comprises:

a) contacting a biological sample from the subject with an antigen antibody-binding moiety (e.g., an antigen on a multiwell plate or bead) under conditions suitable to transform the antibody present in the sample into a complex comprising, consisting of, or consisting essentially of the antibody and the antigen antibody-binding moiety; and b) determining the level of the complex, thereby determining the level of the antibody present in the sample.

In some embodiments, the method further comprises c) comparing the level of the antibody present in the sample to a control level of the antibody, wherein the level of the antibody present in the sample is indicative of an increased likelihood of the subject having Lyme disease.

In some embodiments, the control level of the antibody is the level of the antibody in a sample from a healthy control subject or an average level of the antibody present in a sample from a cohort of healthy control subjects.

In some embodiments, a similar level of antibody in a sample from a subject, relative to control level, is indicative of an increased likelihood of the subject not having Lyme disease. In some embodiments, a difference in the level of antibody in a sample from a subject, relative to control level, is indicative of an increased likelihood of the subject having Lyme disease.

The disclosure provides kits and assay methods for the precise detection of the pathogen that causes Lyme borreliosis. Disclosed are assay reagents provided in the form of a test kit, optionally together with written instructions for performing an evaluation of biomarkers to predict the likelihood of Lyme disease in a subject. The kit optimally comprises, consists of or consists essentially of a control-binding molecule that binds to a control molecule. More specifically, disclosed is an immunoassay leading to the rapid and simultaneous detection of antibodies to a wide range of proteins and peptide antigens in biological fluids of patients with Lyme borreliosis. This immunoassay involves the covalent coupling of full-length proteins or peptides (the antigens) from the pathogen on an identifiable solid support (e.g., fluorescent microspheres). The thus obtained antigen-coupled microspheres capture and bind specific antibodies present in the biological fluid (e.g., serum). Biotinylated detection antibodies specific to the analytes of interest (either anti-human IgG for one channel, and anti-human IgM/J-chain or Fc region for the second channel) are added and form an antibody-antigen sandwich. Phycoerythrin (PE)-conjugated streptavidin is added, which binds to the biotinylated detection antibodies. Beads are read on a dual-laser flow-based detection instrument. One laser classifies the bead and determines the analyte that is being detected. The second laser determines the magnitude of the PE-derived signal, which is in direct proportion to the amount of analyte bound. Signals are processed for QC, dynamic range, background and other features of the fluorescence bead-based assay to insure confidence in the signal. Only signals which lie above the pre-established QC thresholds are further processed. A decision-tree based machine-learning algorithm, XGBoost, is used to interpret the signals from the individual biomarker concentrations and determines the final diagnostic result—either positive or negative. This result will be reported according to a particular laboratory's procedure for reporting results, typically directly into the laboratory information system (LIS).

Diagnosing Different Classes of Lyme Disease

The methods and compositions disclosed herein can be used to diagnose Lyme disease over all stages of infection including: early Lyme disease, early disseminated Lyme disease, late disseminated Lyme disease, acute Lyme disease, and post-treatment Lyme disease.

Also disclosed a methods to assess the therapeutic efficacy of existing and candidate therapeutic agents and other types of Lyme disease treatments. As will be appreciated by persons skilled in the art, the relative expression levels of the biomarker panels—or biomarker profiles—are determined as described above, in specimens taken from a subject prior to and again after treatment or, optionally, at progressive stages during treatment. A change in the relative expression of these biomarkers to a non-infection profile of expression levels or to a stable, non-changing profile of relative biomarker expression levels is interpreted as therapeutic efficacy.

Methods of Treating Biological Samples

In an aspect, a method is provided, the method comprising, consisting of, or consisting essentially of: exposing one or more antigens to a biological sample from a patient, wherein the biological sample comprises the antibodies capable of binding: C6, GlpQ, p35, p66, OspC, DbpA, OppA2, ErpQ, OspE, or OspC2 and combinations thereof, wherein the one or more antibodies binds to each of (or one or more of) the antigens and produces fluorescence signal when it is bound to the antigens; and detecting the combined fluorescence value of the one or more antibodies bound to each of (or one or more of) the antigens.

In some embodiments, the biological sample comprises antibodies capable of binding the antigens of: C6, GlpQ, p35, p66, OspC, DbpA, OppA2, ErpQ, OspE, or OspC2 and combinations thereof and the one or more antibodies binds to each of (or one or more of) these antigens and produces a fluorescent signal when it is bound to the antigens.

Methods of Treating Lyme Disease

In an aspect, methods of treating Lyme disease are provided. In some embodiments, methods of treating Lyme disease include treatment using one or more antibiotics. In some embodiments, the one or more antibiotics comprises any one or more of doxycycline, amoxicillin, azithromycin cefuroxime, cefotaxime, penicillin G and ceftriaxone.

In an aspect, any of the methods of diagnosing Lyme disease described herein can be paired with treating Lyme disease. In some embodiments, treating Lyme disease includes treatment with one or more antibiotics. In some embodiments, the one or more antibiotics comprises any one or more of doxycycline, amoxicillin, azithromycin, cefuroxime, cefotaxime, penicillin G and ceftriaxone.

FIG. 7 is a flowchart illustrating the timeline for patient treatment beginning with when a patient presents to a provider with symptoms such as a tick bite skin rash or other clinical symptoms. A standard blood draw is performed and sent to a clinical laboratory for testing. Sample processing is performed on diagnostic analyzers commonly in place in clinical laboratories or in a central lab or in a doctor's office. Using the methods and compositions disclosed herein, a provider receives test results within 24-48 hours, and is able to prescribe appropriate treatment, or order additional tests for other diseases.

Utilizing Decision Trees for Lyme Disease Diagnosis Development of a Decision Tree According to certain embodiments, diagnosing Lyme disease is achieved by using a classification algorithm. In some embodiments, the classification algorithm is selected from the group comprising a decision tree classifier, logistic regression (LR) classifier, nearest neighbor classifier, neural network classifier, Gaussian mixture model (GMM), Support Vector Machine (SVM) classifier, nearest centroid classifier, linear regression classifier, linear discriminant analysis (LDA) classifier, quadratic discriminant analysis (QDA) classifier and random forest classifier. A standard decision tree works such that each feature is tested to see if the antibody response is above or below a threshold. A boosted gradient tree learns how to evaluate all supporting evidence for best performance, and trims or boosts branches to create the final tree. There is not typically a 1:1 correlation between antigen detection and diagnostic result. See FIGS. 5A and 5B and 14A and 14B.

The disclosure can be understood by the following numbered paragraphs:

Paragraph 1. A method for diagnosing a human as having Lyme disease, the method comprising: obtaining a human sample, detecting the reactivity of IgG and IgM antibodies in a sample from said human to an array of antigens, the array of antigens comprising, consisting of or consisting essentially of C6, GlpQ, p35, p66, OspC, DbpA, OppA2, ErpQ, OspE, and OspC2, generating an antibody profile based on the reactivity of the IgG and IgM antibodies in the sample to said array of antigens, classifying the sample as indicative of Lyme disease or not Lyme disease based on the classification and diagnosing said human as having Lyme disease based on the classification.

Paragraph 2. The method of paragraph 1 wherein classifying said human comprises classifying the sample by detecting at least one signal from OspC2.

Paragraph 3. The method of paragraph 2, wherein the at least one signal results from the binding of an IgM antibody to OspC2.

Paragraph 4. The method of paragraph 2, wherein the at least one signal from OspC2 includes at least one fluorescent signal produced as a result of the OspC2 binding to an IgM antibody.

Paragraph 5. The method of paragraph 4 wherein, the at least one OspC2/IgG fluorescent signal is analyzed against a cutoff value relative to a normalized control, wherein the cutoff value is at or greater than 167.5.

Paragraph 6. The method of paragraph 5 wherein, the cutoff value is between 167.5 and 1500 relative to a normalized control value, for example, about 168, about 169, about 170, about 171, about 172, about 173, or about 174.

Paragraph 7. The method of paragraphs 5-6 wherein, if the at least one OspC2/IgG fluorescent signal is greater than or equal to about 167.5 or between about 167.5 and 1500, the sample is classified as being derived from a patient with Lyme disease.

Paragraph 7.1. The method of paragraphs 5-6 wherein, if the at least one OspC2/IgG fluorescent signal is greater than or equal to about 167.5 or between about 167.5 and 1500, the sample is classified using an additional decision including detecting at least one signal from C6, GlpQ, p35, p66, OspC, DbpA, OppA2, ErpQ, OspE, OspC, or variants thereof.

Paragraph 8. The method of paragraphs 5-7 wherein, if the at least one OspC2/IgG fluorescent signal is less than or equal to 166 or between about 1 and 166, the sample is classified using an additional decision including detecting at least one signal from C6, GlpQ, p35, p66, OspC, DbpA, OppA2, ErpQ, OspE, OspC, or combinations thereof.

Paragraph 9. The method of any preceding paragraph wherein, the at least one signal results from the binding of OspC2 to an IgG antibody.

Paragraph 10. The method of any preceding paragraph wherein, the at least one fluorescent signal is analyzed against a cutoff value relative to a normalized control Paragraph 11. The method of paragraph 10, wherein the OspC2/IgM cutoff value is 342 or between 342 and 1500.

Paragraph 12. The method of paragraph 10, wherein the OspC2/IgM cutoff value is between 342 and 1500 relative to a normalized control value, for example about 345, about 346, about 347, about 348, about 349, or about 350.

Paragraph 13. The method of paragraphs 10-12, wherein if the at least one OspC2/IgM fluorescent signal is greater than or equal to 342 or between 342 and 1500, the sample is classified as being derived from a patient with Lyme disease.

Paragraph 13.1. The method of paragraphs 10-12, wherein if the at least one fluorescent signal is greater than or equal to 342 or between 342 and 1500, the sample is classified using an additional decision including detecting at least one signal from C6, GlpQ, p35, p66, OspC, DbpA, OppA2, ErpQ, OspE, OspC, or variants thereof.

Paragraph 14. The method of paragraphs 10-12, if the at least one OspC2/IgM fluorescent signal is greater than or equal to 342 or between 342 and 1500, the sample is classified using a separate decision including detecting at least one signal from C6, GlpQ, p35, p66, OspC, DbpA, OppA2, ErpQ, OspE, OspC, or variants thereof.

Paragraph 15. The method of any preceding paragraph, wherein after detection at least one fluorescent signal The reactivity of each of the antigens (C6, GlpQ, p35, p66, OspC, DbpA, OppA2, ErpQ, OspE, and OspC) is evaluated as discussed above for OspC2. In some embodiments, the classification and diagnostic result is based on the reactivity of 18 assays: IgG and IgM reactivity to each of C6, GlpQ, p35, p66, OspC, DbpA, OppA2, ErpQ, OspE, OspC and OspC2.

In some embodiments, the classification and diagnostic result is based on the reactivity of less than all 18 assays: IgG and IgM reactivity to each of C6, GlpQ, p35, p66, OspC, DbpA, OppA2, ErpQ, OspE, OspC and OspC2.

In one exemplary embodiment, classifying a sample using at least one decision includes detecting at least one signal from C6. In some embodiments, the at least one signal results from the binding of an IgG antibody to C6. In some embodiments, the at least one signal results from the binding of an IgM antibody to C6. In some embodiments, the at least one signal results from the binding of an IgG and an IgM antibody to C6.

In some embodiments, the at least one fluorescent signal is analyzed against a cutoff value relative to a normalized control, wherein the C6/IgG cutoff value is greater than or equal to 298. In some embodiments, the C6/IgG cutoff value is greater than or equal to 298-1500.

In some embodiments, if the at least one C6/IgG fluorescent signal is greater than or equal to 298 or between about 298-1500, the sample is classified as being derived from a patient with Lyme disease. In some embodiments, if the at least one C6/IgG fluorescent signal is greater than or equal to 298 or between about 298-1500, the sample is classified using a separate decision including detecting at least one signal from p35, p66, OspC, DbpA, OppA2, ErpQ, OspE, and OspC2. In some embodiments, the positive result (greater than or equal to 298 or between about 298-1500) for C6/IgG is not enough to classify the sample.

In some embodiments, if the at least one C6/IgG fluorescent signal is less than or equal to 297 or between about 1-297, the sample is classified as being not derived from a patient with Lyme disease. In some embodiments, if the at least one C6/IgG fluorescent signal is less than or equal to 297 or between about 1-297, the sample is classified using a separate decision including detecting at least one signal from p35, p66, OspC, DbpA, OppA2, ErpQ, OspE, and OspC2. In some embodiments, the negative result (less than or equal to 297 or between about 1-297) for C6/IgG is not enough to classify the sample.

In some embodiments, the at least one fluorescent signal is analyzed against a cutoff value relative to a normalized control, wherein the C6/IgG cutoff value is greater than or equal to 298. In some embodiments, the C6/IgG cutoff value is greater than or equal to 298-1500.

In some embodiments, if the at least one C6/IgM fluorescent signal is greater than or equal to 2645 or between about 2645-1500, the sample is classified as being derived from a patient with Lyme disease. In some embodiments, if the at least one C6/IgM fluorescent signal is greater than or equal to 2645 or between about 2645-1500, the sample is classified using a separate decision including detecting at least one signal from p35, p66, OspC, DbpA, OppA2, ErpQ, OspE, and OspC2. In some embodiments, the positive result (greater than or equal to 2645 or between about 2645-1500) for C6/IgM is not enough to classify the sample.

In some embodiments, if the at least one C6/IgM fluorescent signal is less than or equal to 2644 or between about 1-2644, the sample is classified as being not derived from a patient with Lyme disease. In some embodiments, if the at least one C6/IgM fluorescent signal is less than or equal to 2644 or between about 1-2644, the sample is classified using a separate decision including detecting at least one signal from p35, p66, OspC, DbpA, OppA2, ErpQ, OspE, and OspC2. In some embodiments, the negative result (less than or equal to 2644 or between about 1-2644) for C6/IgM is not enough to classify the sample.

In one exemplary embodiment, classifying a sample using at least one decision includes detecting at least one signal from OspC. In some embodiments, the at least one signal results from the binding of an IgG antibody to OspC. In some embodiments, the at least one signal results from the binding of an IgM antibody to OspC. In some embodiments, the at least one signal results from the binding of an IgG and an IgM antibody to OspC.

In some embodiments, the at least one fluorescent signal is analyzed against a cutoff value relative to a normalized control, wherein the OspC/IgG cutoff value is greater than or equal to 436. In some embodiments, the OspC/IgG cutoff value is greater than or equal to 436-1500.

In some embodiments, if the at least one OspC/IgG fluorescent signal is greater than or equal to 436 or between about 436-1500, the sample is classified as being derived from a patient with Lyme disease. In some embodiments, if the at least one OspC/IgG fluorescent signal is greater than or equal to 436 or between about 436-1500, the sample is classified using a separate decision including detecting at least one signal from p35, p66, C6, DbpA, OppA2, ErpQ, OspE, and OspC2. In some embodiments, the positive result (greater than or equal to 436 or between about 436-1500) for OspC/IgG is not enough to classify the sample.

In some embodiments, if the at least one OspC/IgG fluorescent signal is less than or equal to 435 or between about 1-435, the sample is classified as being not derived from a patient with Lyme disease. In some embodiments, if the at least one OspC/IgG fluorescent signal is less than or equal to 435 or between about 1-435, the sample is classified using a separate decision including detecting at least one signal from p35, p66, C6, DbpA, OppA2, ErpQ, OspE, and OspC2. In some embodiments, the negative result (less than or equal to 435 or between about 1-435) for OspC/IgG is not enough to classify the sample.

In some embodiments, the at least one fluorescent signal is analyzed against a cutoff value relative to a normalized control, wherein the OspC/IgM cutoff value is greater than or equal to 400. In some embodiments, the OspC/IgM cutoff value is greater than or equal to 400-1500.

In some embodiments, if the at least one OspC/IgM fluorescent signal is greater than or equal to 400 or between about 400-1500, the sample is classified as being derived from a patient with Lyme disease. In some embodiments, if the at least one OspC/IgM fluorescent signal is greater than or equal to 400 or between about 400-1500, the sample is classified using a separate decision including detecting at least one signal from p35, p66, C6, DbpA, OppA2, ErpQ, OspE, and OspC2. In some embodiments, the positive result (greater than or equal to 400 or between about 400-1500) for OspC/IgM is not enough to classify the sample.

In some embodiments, if the at least one OspC/IgM fluorescent signal is less than or equal to 399 or between about 1-399, the sample is classified as being not derived from a patient with Lyme disease. In some embodiments, if the at least one OspC/IgM fluorescent signal is less than or equal to 399 or between about 1-399, the sample is classified using a separate decision including detecting at least one signal from p35, p66, C6, DbpA, OppA2, ErpQ, OspE, and OspC2. In some embodiments, the negative result (less than or equal to 399 or between about 1-399) for OspC/IgM is not enough to classify the sample.

In one exemplary embodiment, classifying a sample using at least one decision includes detecting at least one signal from OspE. In some embodiments, the at least one signal results from the binding of an IgG antibody to OspE. In some embodiments, the at least one signal results from the binding of an IgM antibody to OspE. In some embodiments, the at least one signal results from the binding of an IgG and an IgM antibody to OspE.

In some embodiments, the at least one fluorescent signal is analyzed against a cutoff value relative to a normalized control, wherein the OspE/IgG cutoff value is greater than or equal to 305. In some embodiments, the OspE/IgG cutoff value is greater than or equal to 305-1500.

In some embodiments, if the at least one OspE/IgG fluorescent signal is greater than or equal to 305 or between about 305-1500, the sample is classified as being derived from a patient with Lyme disease. In some embodiments, if the at least one OspE/IgG fluorescent signal is greater than or equal to 305 or between about 305-1500, the sample is classified using a separate decision including detecting at least one signal from p35, p66, OspC, DbpA, OppA2, ErpQ, C6 and OspC2. In some embodiments, the positive result (greater than or equal to 305 or between about 305-1500) for OspE/IgG is not enough to classify the sample.

In some embodiments, if the at least one OspE/IgG fluorescent signal is less than or equal to 304 or between about 1-304, the sample is classified as being not derived from a patient with Lyme disease. In some embodiments, if the at least one OspE/IgG fluorescent signal is less than or equal to 304 or between about 1-304, the sample is classified using a separate decision including detecting at least one signal from p35, p66, OspE, DbpA, OppA2, ErpQ, C6 and OspC2. In some embodiments, the negative result (less than or equal to 304 or between about 1-304) for OspE/IgG is not enough to classify the sample.

In some embodiments, the at least one fluorescent signal is analyzed against a cutoff value relative to a normalized control, wherein the OspE/IgM cutoff value is greater than or equal to 293.8. In some embodiments, the OspE/IgM cutoff value is greater than or equal to 293.8-1500.

In some embodiments, if the at least one OspE/IgM fluorescent signal is greater than or equal to 293.8 or between about 293.8-1500, the sample is classified as being derived from a patient with Lyme disease. In some embodiments, if the at least one OspE/IgM fluorescent signal is greater than or equal to 293.8 or between about 293.8-1500, the sample is classified using a separate decision including detecting at least one signal from p35, p66, OspC, DbpA, OppA2, ErpQ, C6 and OspC2. In some embodiments, the positive result (greater than or equal to 293.8 or between about 293.8-1500) for OspE/IgM is not enough to classify the sample.

In some embodiments, if the at least one OspE/IgM fluorescent signal is less than or equal to 292 or between about 1-292, the sample is classified as being not derived from a patient with Lyme disease. In some embodiments, if the at least one OspE/IgM fluorescent signal is less than or equal to 292 or between about 1-292, the sample is classified using a separate decision including detecting at least one signal from p35, p66, OspC, DbpA, OppA2, ErpQ, OspC, C6, and OspC2. In some embodiments, the negative result (less than or equal to 292 or between about 1-292) for OspE/IgM is not enough to classify the sample.

In one exemplary embodiment, classifying a sample using at least one decision includes detecting at least one signal from OppA2. In some embodiments, the at least one signal results from the binding of an IgG antibody to OppA2. In some embodiments, the at least one signal results from the binding of an IgM antibody to OppA2. In some embodiments, the at least one signal results from the binding of an IgG and an IgM antibody to OppA2.

In some embodiments, the at least one fluorescent signal is analyzed against a cutoff value relative to a normalized control, wherein the OppA2/IgG cutoff value is greater than or equal to 531. In some embodiments, the OppA2/IgG cutoff value is greater than or equal to 531-1500.

In some embodiments, if the at least one OppA2/IgG fluorescent signal is greater than or equal to 531 or between about 531-1500, the sample is classified as being derived from a patient with Lyme disease. In some embodiments, if the at least one OppA2/IgG fluorescent signal is greater than or equal to 531 or between about 531-1500, the sample is classified using a separate decision including detecting at least one signal from p35, p66, OspC, DbpA, C6, ErpQ, DbpA, and OspC2. In some embodiments, the positive result (greater than or equal to 531 or between about 531-1500) for OppA2/IgG is not enough to classify the sample.

In some embodiments, if the at least one OppA2/IgG fluorescent signal is less than or equal to 530 or between about 1-530, the sample is classified as being not derived from a patient with Lyme disease. In some embodiments, if the at least one OppA2/IgG fluorescent signal is less than or equal to 530 or between about 1-530, the sample is classified using a separate decision including detecting at least one signal from p35, p66, OspC, DbpA, C6, ErpQ, DbpA, and OspC2. In some embodiments, the negative result (less than or equal to 530 or between about 1-530) for OppA2/IgG is not enough to classify the sample.

In some embodiments, the at least one fluorescent signal is analyzed against a cutoff value relative to a normalized control, wherein the OppA2/IgM cutoff value is greater than or equal to 332.3. In some embodiments, the OppA2/IgM cutoff value is greater than or equal to 332.3-1500.

In some embodiments, if the at least one OppA2/IgM fluorescent signal is greater than or equal to 332.3 or between about 332.3-1500, the sample is classified as being derived from a patient with Lyme disease. In some embodiments, if the at least one OppA2/IgM fluorescent signal is greater than or equal to 332.3 or between about 332.3-1500, the sample is classified using a separate decision including detecting at least one signal from p35, p66, OspC, DbpA, C6, ErpQ, DbpA, and OspC2. In some embodiments, the positive result (greater than or equal to 332.3 or between about 332.3-1500) for OppA2/IgM is not enough to classify the sample.

In some embodiments, if the at least one OppA2/IgM fluorescent signal is less than or equal to 331 or between about 1-331, the sample is classified as being not derived from a patient with Lyme disease. In some embodiments, if the at least one OppA2/IgM fluorescent signal is less than or equal to 331 or between about 1-331, the sample is classified using a separate decision including detecting at least one signal from p35, p66, OspC, DbpA, C6, ErpQ, DbpA, and OspC2. In some embodiments, the negative result (less than or equal to 331 or between about 1-331) for OppA2/IgM is not enough to classify the sample.

In one exemplary embodiment, classifying a sample using at least one decision includes detecting at least one signal from DbpA. In some embodiments, the at least one signal results from the binding of an IgG antibody to DbpA. In some embodiments, the at least one signal results from the binding of an IgM antibody to DbpA. In some embodiments, the at least one signal results from the binding of an IgG and an IgM antibody to DbpA.

In some embodiments, the at least one fluorescent signal is analyzed against a cutoff value relative to a normalized control, wherein the DbpA/IgG cutoff value is greater than or equal to 346. In some embodiments, the DbpA/IgG cutoff value is greater than or equal to 346-1500.

In some embodiments, if the at least one DbpA/IgG fluorescent signal is greater than or equal to 346 or between about 346-1500, the sample is classified as being derived from a patient with Lyme disease. In some embodiments, if the at least one DbpA/IgG fluorescent signal is greater than or equal to 346 or between about 346-1500, the sample is classified using a separate decision including detecting at least one signal from p35, p66, OspC, OppA2, C6, ErpQ, OspE, and OspC2. In some embodiments, the positive result (greater than or equal to 346 or between about 346-1500) for DbpA/IgG is not enough to classify the sample.

In some embodiments, if the at least one DbpA/IgG fluorescent signal is less than or equal to 345 or between about 1-345, the sample is classified as being not derived from a patient with Lyme disease. In some embodiments, if the at least one DbpA/IgG fluorescent signal is less than or equal to 345 or between about 1-345, the sample is classified using a separate decision including detecting at least one signal from p35, p66, OspC, OppA2, C6, ErpQ, OspE, and OspC2. In some embodiments, the negative result (less than or equal to 345 or between about 1-345) for DbpA/IgG is not enough to classify the sample.

In some embodiments, the at least one fluorescent signal is analyzed against a cutoff value relative to a normalized control, wherein the DbpA/IgM cutoff value is greater than or equal to 535. In some embodiments, the DbpA/IgM cutoff value is greater than or equal to 535-1500.

In some embodiments, if the at least one DbpA/IgM fluorescent signal is greater than or equal to 535 or between about 535-1500, the sample is classified as being derived from a patient with Lyme disease. In some embodiments, if the at least one DbpA/IgM fluorescent signal is greater than or equal to 535 or between about 535-1500, the sample is classified using a separate decision including detecting at least one signal from p35, p66, OspC, OppA2, C6, ErpQ, OspE, and OspC2. In some embodiments, the positive result (greater than or equal to 535 or between about 535-1500) for DbpA/IgM is not enough to classify the sample.

In some embodiments, if the at least one DbpA/IgM fluorescent signal is less than or equal to 534 or between about 1-534, the sample is classified as being not derived from a patient with Lyme disease. In some embodiments, if the at least one DbpA/IgM fluorescent signal is less than or equal to 534 or between about 1-534, the sample is classified using a separate decision including detecting at least one signal from p35, p66, OspC, OppA2, C6, ErpQ, OspE, and OspC2. In some embodiments, the negative result (less than or equal to 534 or between about 1-534) for DbpA/IgM is not enough to classify the sample.

In one exemplary embodiment, classifying a sample using at least one decision includes detecting at least one signal from ErpQ. In some embodiments, the at least one signal results from the binding of an IgG antibody to ErpQ. In some embodiments, the at least one signal results from the binding of an IgM antibody to ErpQ. In some embodiments, the at least one signal results from the binding of an IgG and an IgM antibody to ErpQ.

In some embodiments, the at least one fluorescent signal is analyzed against a cutoff value relative to a normalized control, wherein the ErpQ/IgG cutoff value is greater than or equal to 362. In some embodiments, the ErpQ/IgG cutoff value is greater than or equal to 362-1500.

In some embodiments, if the at least one ErpQ/IgG fluorescent signal is greater than or equal to 362 or between about 362-1500, the sample is classified as being derived from a patient with Lyme disease. In some embodiments, if the at least one ErpQ/IgG fluorescent signal is greater than or equal to 362 or between about 362-1500, the sample is classified using a separate decision including detecting at least one signal from p35, p66, OspC, OppA2, C6, DbpA, OspE, and OspC2. In some embodiments, the positive result (greater than or equal to 362 or between about 362-1500) for ErpQ/IgG is not enough to classify the sample.

In some embodiments, if the at least one ErpQ/IgG fluorescent signal is less than or equal to 361 or between about 1-361, the sample is classified as being not derived from a patient with Lyme disease. In some embodiments, if the at least one ErpQ/IgG fluorescent signal is less than or equal to 361 or between about 1-361, the sample is classified using a separate decision including detecting at least one signal from p35, p66, OspC, OppA2, C6, DbpA, OspE, and OspC2. In some embodiments, the negative result (less than or equal to 361 or between about 1-361) for ErpQ/IgG is not enough to classify the sample.

In some embodiments, the at least one fluorescent signal is analyzed against a cutoff value relative to a normalized control, wherein the ErpQ/IgM cutoff value is greater than or equal to 128. In some embodiments, the ErpQ/IgM cutoff value is greater than or equal to 128-1500.

In some embodiments, if the at least one ErpQ/IgM fluorescent signal is greater than or equal to 128 or between about 128-1500, the sample is classified as being derived from a patient with Lyme disease. In some embodiments, if the at least one ErpQ/IgM fluorescent signal is greater than or equal to 128 or between about 128-1500, the sample is classified using a separate decision including detecting at least one signal from p35, p66, OspC, OppA2, C6, DbpA, OspE, and OspC2. In some embodiments, the positive result (greater than or equal to 128 or between about 128-1500) for ErpQ/IgM is not enough to classify the sample.

In some embodiments, if the at least one ErpQ/IgM fluorescent signal is less than or equal to 127 or between about 1-127, the sample is classified as being not derived from a patient with Lyme disease. In some embodiments, if the at least one ErpQ/IgM fluorescent signal is less than or equal to 127 or between about 1-127, the sample is classified using a separate decision including detecting at least one signal from p35, p66, OspC, OppA2, C6, DbpA, OspE, and OspC2. In some embodiments, the negative result (less than or equal to 127 or between about 1-127) for ErpQ/IgM is not enough to classify the sample.

In one exemplary embodiment, classifying a sample using at least one decision includes detecting at least one signal from p35. In some embodiments, the at least one signal results from the binding of an IgG antibody to p35. In some embodiments, the at least one signal results from the binding of an IgM antibody to p35. In some embodiments, the at least one signal results from the binding of an IgG and an IgM antibody to p35.

In some embodiments, the at least one fluorescent signal is analyzed against a cutoff value relative to a normalized control, wherein the p35/IgG cutoff value is greater than or equal to 686. In some embodiments, the p35/IgG cutoff value is greater than or equal to 686-1500.

In some embodiments, if the at least one p35/IgG fluorescent signal is greater than or equal to 686 or between about 686-1500, the sample is classified as being derived from a patient with Lyme disease. In some embodiments, if the at least one p35/IgG fluorescent signal is greater than or equal to 686 or between about 686-1500, the sample is classified using a separate decision including detecting at least one signal from ErpQ, p66, OspC, OppA2, C6, DbpA, OspE, and OspC2. In some embodiments, the positive result (greater than or equal to 686 or between about 686-1500) for p35/IgG is not enough to classify the sample.

In some embodiments, if the at least one p35/IgG fluorescent signal is less than or equal to 685 or between about 1-685, the sample is classified as being not derived from a patient with Lyme disease. In some embodiments, if the at least one p35/IgG fluorescent signal is less than or equal to 685 or between about 1-685, the sample is classified using a separate decision including detecting at least one signal from ErpQ, p66, OspC, OppA2, C6, DbpA, OspE, and OspC2. In some embodiments, the negative result (less than or equal to 685 or between about 1-685) for p35/IgG is not enough to classify the sample.

In some embodiments, the at least one fluorescent signal is analyzed against a cutoff value relative to a normalized control, wherein the p35/IgM cutoff value is greater than or equal to 2350. In some embodiments, the p35/IgM cutoff value is greater than or equal to 2350-1500.

In some embodiments, if the at least one p35/IgM fluorescent signal is greater than or equal to 2350 or between about 2350-1500, the sample is classified as being derived from a patient with Lyme disease. In some embodiments, if the at least one p35/IgM fluorescent signal is greater than or equal to 2350 or between about 2350-1500, the sample is classified using a separate decision including detecting at least one signal from ErpQ, p66, OspC, OppA2, C6, DbpA, OspE, and OspC2. In some embodiments, the positive result (greater than or equal to 2350 or between about 2350-1500) for p35/IgM is not enough to classify the sample.

In some embodiments, if the at least one p35/IgM fluorescent signal is less than or equal to 2349 or between about 1-2349, the sample is classified as being not derived from a patient with Lyme disease. In some embodiments, if the at least one p35/IgM fluorescent signal is less than or equal to 2349 or between about 1-2349, the sample is classified using a separate decision including detecting at least one signal from ErpQ, p66, OspC, OppA2, C6, DbpA, OspE, and OspC2. In some embodiments, the negative result (less than or equal to 2349 or between about 1-2349) for p35/IgM is not enough to classify the sample.

In one exemplary embodiment, classifying a sample using at least one decision includes detecting at least one signal from p66. In some embodiments, the at least one signal results from the binding of an IgG antibody to p66. In some embodiments, the at least one signal results from the binding of an IgM antibody to p66. In some embodiments, the at least one signal results from the binding of an IgG and an IgM antibody to p66.

In some embodiments, the at least one fluorescent signal is analyzed against a cutoff value relative to a normalized control, wherein the p66/IgG cutoff value is greater than or equal to 689. In some embodiments, the p66/IgG cutoff value is greater than or equal to 689-1500.

In some embodiments, if the at least one p66/IgG fluorescent signal is greater than or equal to 689 or between about 689-1500, the sample is classified as being derived from a patient with Lyme disease. In some embodiments, if the at least one p66/IgG fluorescent signal is greater than or equal to 689 or between about 689-1500, the sample is classified using a separate decision including detecting at least one signal from ErpQ, p35, OspC, OppA2, C6, DbpA, OspE, and OspC2. In some embodiments, the positive result (greater than or equal to 689 or between about 689-1500) for p66/IgG is not enough to classify the sample.

In some embodiments, if the at least one p66/IgG fluorescent signal is less than or equal to 688 or between about 1-688, the sample is classified as being not derived from a patient with Lyme disease. In some embodiments, if the at least one p66/IgG fluorescent signal is less than or equal to 688 or between about 1-688, the sample is classified using a separate decision including detecting at least one signal from ErpQ, p35, OspC, OppA2, C6, DbpA, OspE, and OspC2. In some embodiments, the negative result (less than or equal to 688 or between about 1-688) for p66/IgG is not enough to classify the sample.

In some embodiments, the at least one fluorescent signal is analyzed against a cutoff value relative to a normalized control, wherein the p66/IgM cutoff value is greater than or equal to 497. In some embodiments, the p66/IgM cutoff value is greater than or equal to 497-1500.

In some embodiments, if the at least one p66/IgM fluorescent signal is greater than or equal to 497 or between about 497-1500, the sample is classified as being derived from a patient with Lyme disease. In some embodiments, if the at least one p66/IgM fluorescent signal is greater than or equal to 497 or between about 497-1500, the sample is classified using a separate decision including detecting at least one signal from ErpQ, p35, OspC, OppA2, C6, DbpA, OspE, and OspC2. In some embodiments, the positive result (greater than or equal to 497 or between about 497-1500) for p66/IgM is not enough to classify the sample.

In some embodiments, if the at least one p66/IgM fluorescent signal is less than or equal to 498 or between about 1-498, the sample is classified as being not derived from a patient with Lyme disease. In some embodiments, if the at least one p66/IgM fluorescent signal is less than or equal to 498 or between about 1-498, the sample is classified using a separate decision including detecting at least one signal from ErpQ, p35, OspC, OppA2, C6, DbpA, OspE, and OspC2. In some embodiments, the negative result (less than or equal to 498 or between about 1-498) for p66/IgM is not enough to classify the sample.

In one exemplary embodiment, classifying a sample using at least one decision includes detecting at least one signal from OspC2. In some embodiments, the at least one signal results from the binding of an IgG antibody to OspC2. In some embodiments, the at least one signal results from the binding of an IgM antibody to OspC2. In some embodiments, the at least one signal results from the binding of an IgG and an IgM antibody to OspC2.

In some embodiments, the at least one fluorescent signal is analyzed against a cutoff value relative to a normalized control, wherein the OspC2/IgG cutoff value is greater than or equal to 167.5. In some embodiments, the OspC2/IgG cutoff value is greater than or equal to 167.5-1500.

In some embodiments, if the at least one OspC2/IgG fluorescent signal is greater than or equal to 167.5 or between about 167.5-1500, the sample is classified as being derived from a patient with Lyme disease. In some embodiments, if the at least one OspC2/IgG fluorescent signal is greater than or equal to 167.5 or between about 167.5-1500, the sample is classified using a separate decision including detecting at least one signal from ErpQ, p35, OspC, OppA2, C6, DbpA, OspE, and p66. In some embodiments, the positive result (greater than or equal to 167.5 or between about 167.5-1500) for OspC2/IgG is not enough to classify the sample.

In some embodiments, if the at least one OspC2/IgG fluorescent signal is less than or equal to 166 or between about 1-166, the sample is classified as being not derived from a patient with Lyme disease. In some embodiments, if the at least one OspC2/IgG fluorescent signal is less than or equal to 166 or between about 1-166, the sample is classified using a separate decision including detecting at least one signal from ErpQ, p35, OspC, OppA2, C6, DbpA, OspE, and p66. In some embodiments, the negative result (less than or equal to 166 or between about 1-166) for OspC2/IgG is not enough to classify the sample.

In some embodiments, the at least one fluorescent signal is analyzed against a cutoff value relative to a normalized control, wherein the OspC2/IgM cutoff value is greater than or equal to 342. In some embodiments, the OspC2/IgM cutoff value is greater than or equal to 342-1500.

In some embodiments, if the at least one OspC2/IgM fluorescent signal is greater than or equal to 342 or between about 342-1500, the sample is classified as being derived from a patient with Lyme disease. In some embodiments, if the at least one OspC2/IgM fluorescent signal is greater than or equal to 342 or between about 342-1500, the sample is classified using a separate decision including detecting at least one signal from ErpQ, p35, OspC, OppA2, C6, DbpA, OspE, and p66. In some embodiments, the positive result (greater than or equal to 342 or between about 342-1500) for OspC2/IgM is not enough to classify the sample.

In some embodiments, if the at least one OspC2/IgM fluorescent signal is less than or equal to 341 or between about 1-341, the sample is classified as being not derived from a patient with Lyme disease. In some embodiments, if the at least one OspC2/IgM fluorescent signal is less than or equal to 341 or between about 1-341, the sample is classified using a separate decision including detecting at least one signal from ErpQ, p35, OspC, OppA2, C6, DbpA, OspE, and p66. In some embodiments, the negative result (less than or equal to 341 or between about 1-341) for OspC2/IgM is not enough to classify the sample.

For avoidance of doubt, In some embodiments, the detection of a particular antigen or lack of detection of a particular antigen is not enough to classify the sample. The classification model looks at data from all 18 antigens (IgG and IgM from C6, GlpQ, p35, p66, OspC, DbpA, OppA2, ErpQ, OspE, and OspC2) are needed to classify the sample.

In one exemplary embodiment, classifying a sample using at least one decision includes detecting at least one signal from GlpQ. In some embodiments, the at least one signal results from the binding of an IgG antibody to GlpQ. In some embodiments, the at least one signal results from the binding of an IgM antibody to GlpQ. In some embodiments, the at least one signal results from the binding of an IgG and an IgM antibody to GlpQ.

In some embodiments, the at least one fluorescent signal is analyzed against a cutoff value relative to a normalized control, wherein the GlpQ/IgG cutoff value is greater than or equal to 500. In some embodiments, the GlpQ/IgG cutoff value is greater than or equal to 500-1500.

In some embodiments, if the at least one GlpQ/IgG fluorescent signal is greater than or equal to 500 or between about 500-1500, the sample is classified as being derived from a patient with Lyme disease. In some embodiments, if the at least one GlpQ/IgG fluorescent signal is greater than or equal to 500 or between about 500-1500, the sample is classified using a separate decision including detecting at least one signal from p35, p66, OspC, DbpA, OppA2, ErpQ, OspE, and OspC2. In some embodiments, the positive result (greater than or equal to 500 or between about 500-1500) for GlpQ/IgG is not enough to classify the sample.

In some embodiments, if the at least one GlpQ/IgG fluorescent signal is less than or equal to 499 or between about 1-499, the sample is classified as being not derived from a patient with Lyme disease. In some embodiments, if the at least one GlpQ/IgG fluorescent signal is less than or equal to 499 or between about 1-499, the sample is classified using a separate decision including detecting at least one signal from p35, p66, OspC, DbpA, OppA2, ErpQ, OspE, and OspC2. In some embodiments, the negative result (less than or equal to 499 or between about 1-499) for GlpQ/IgG is not enough to classify the sample.

In some embodiments, the at least one fluorescent signal is analyzed against a cutoff value relative to a normalized control, wherein the GlpQ/IgG cutoff value is greater than or equal to 500. In some embodiments, the GlpQ/IgG cutoff value is greater than or equal to 500-1500.

Diagnostic Analyzer

Disclosed is an analyzer capable of performing a multiplexed immunoassay. Disclosed is an analyzer capable of performing a multiplexed immunoassay and producing signals interpreted by a machine learning algorithm. Disclosed is an analyzer capable of performing a multiplexed immunoassay and producing signals interpreted by a machine learning algorithm to determine a final diagnostic result—either positive or negative.

Clinical Use of a Decision Tree

In an aspect, a method is provided that includes using a decision tree in a clinical setting to diagnose Lyme disease. In some embodiments, the method includes entering the results from biomarkers that have been detected in a sample into the decision tree. In some embodiments, the biomarkers that have been detected are any one or more of C6, GlpQ, p35, p66, OspC, DbpA, OppA2, ErpQ, OspE, and OspC2 or variants thereof. In some embodiments, any one or more of the biomarkers are bound to an antibody and the bound antibody is detected. In some embodiments, the bound antibody is bound to IgM, IgG or IgM and IgG is connected to a fluorophore, which is detected. In some embodiments, any one or more of the biomarkers is bound to an antibody and the biomarker bound to the antibody is detected. In some embodiments, the biomarker bound to the antibody is also bound to a secondary antibody that is attached to a fluorophore, which is detected.

Diagnostic Model

In some embodiments disclosed is a diagnostic model established using a retrospective cohort with known outcomes of a clinical subtype of Lyme disease and healthy controls. In some instances, the diagnostic profile comprises an antibody marker model. The diagnostic model is generated by applying the retrospective data on individuals with Lyme disease and healthy controls to statistical algorithms. In some embodiments, the antibody model is derived by applying logistic regression analysis to the level of one or more antibody markers determined in a retrospective cohort.

In some embodiments, the expression level of one or more sets of antibodies capable of binding an antigen in a sample is determined. Each set of antibodies comprises a group or set of first antibodies capable of binding first or core set of antigen(s), also referred to herein as "core antibodies." In some embodiments, a set of core antibodies comprises IgG or IgM antibodies capable of binding C6, GlpQ, p35, p66, OspC, DbpA, OppA2, ErpQ, OspE, and/or OspC2. In some embodiments, a set of core antibodies comprises IgG antibodies capable of binding C6, GlpQ, p35, p66, OspC, DbpA, OppA2, ErpQ, OspE, and OspC2. In some embodiments, a set of core antibodies comprises IgG antibodies capable of binding C6, OspC, and OspC2; or C6, and OspC2; or C6 and OspC; or OspC, and OspC2.

Each set of antibodies can further comprise a second set of antibodies (non-core antibodies) capable of binding a second set of non-core antigens in addition to the core antibodies. For a defined level of accuracy, the core antibodies in each set of antibodies must be detected in combination with one or more non-core antibodies. Detection of a core antibody is not enough to make a diagnostic decision. In some embodiments, a set of non-core antibodies comprises IgG or IgM antibodies capable of binding C6, GlpQ, p35, p66, OspC, DbpA, OppA2, ErpQ, OspE, and/or OspC2. In some embodiments, a set of non-core antibodies comprises IgM antibodies capable of binding C6, OspC, and OspC2; or C6, and OspC2; or C6 and OspC; or OspC, and OspC2. In some embodiments, a set of non-core antibodies comprises IgG antibodies capable of binding p35, p66, DbpA, OppA2, ErpQ; and OspE.

For example, if C6 is detected but no other non-core antibodies are detected, the diagnostic call is negative. If C6 is detected and one or more non-core antibodies are detected, the diagnostic call is positive. For example, if OspC2 is detected but no other non-core antibodies are detected, the diagnostic call is negative. If OspC2 is detected and one or more non-core antibodies are detected, the diagnostic call is positive. For example, if OspC is detected but no other non-core antibodies are detected, the diagnostic call is negative. If OspC is detected and one or more non-core antibodies are detected, the diagnostic call is positive.

The diagnostic Lyme disease classifier is based on a hierarchy of decisions. The diagnostic classifier is a composite of a core classifier and non-core classifier. The composite classifiers are used in a decision tree. The first decision is whether a core antibody (capable of binding a core antigen) is absent or present. If a core antibody (capable of binding a core antigen) is absent, then the sample is classified as Normal (No Lyme Disease). If a core antibody (capable of binding a core antigen) is present, then the next decision is about the absence or presence of a non-core antibody (capable of binding a non-core antigen). If a non-core antibody (capable of binding a non-core antigen) is absent, then the sample is classified as Normal (No Lyme Disease) or Other (non-healthy non-Lyme). If a non-core antibody (capable of binding a non-core antigen) is present, then the sample is classified as Lyme disease ("LD"). If a core antibody (capable of binding a core antigen) is present without a non-core antibody, a positive call is not made.

For each step of the decision tree, a group or set of core antibodies was identified in each classifier whose expression patterns are diagnostic for a given step in the decision tree. For example, in some embodiments, a 1, 2 or more biomarkers are provided that are diagnostic for the first step in the decision tree, namely the presence or absence of disease. In some embodiments, each of the core antibodies has the same level of accuracy for a given step of the diagnostic decision tree, i.e., detection of any core antibody is all that is needed to move to step 2 (such as C6, OspC, and OspC2). In some embodiments, each of the core antibodies has a different level of accuracy for a given step of the diagnostic decision tree, i.e., detection of a minor core antibody (such as p35, p66, DbpA, OppA2, ErpQ; and OspE) is not enough to move to step 2 and detection of two or more minor core antibodies is needed to move to step 2.

In some embodiments, each of the classifiers contains the same set of antibodies. In some embodiments, the core classifier contains only core antibodies which are different from non-core antibodies. In some embodiments, the core classifier contains a combination of core antibodies which overlap with non-core antibodies and if they overlap, may overlap partially or completely. In either case, the core and non-core antibodies are antibodies capable of binding C6, GlpQ, p35, p66, OspC, DbpA, OppA2, ErpQ, OspE, and/or OspC2 or fragments thereof.

In some embodiments, the non-core classifier contains only non-core antibodies which are different from core antibodies. In some embodiments, the non-core classifier contains a combination of non-core antibodies which overlap with core antibodies and if they overlap, may overlap partially or completely.

The first decision made by the core classifier is whether a core antibody is absent or present in the sample. If a core antibody is absent, then the sample is classified as Normal (N). If a core antibody is present, then the sample drops to the next level. The second decision is about the detection of a second non-core antibody. The sample is classified as Normal (N), Other (non-healthy non-Lyme) or Lyme disease (LD) by the non-core classifier.

Thus, in some embodiments, Lyme disease can be diagnosed by using disease classifiers described herein to first determine whether a core antibody is absent or present and second to determine if a non-core antibody is absent or present:

|  | Core present | Core not absent |
|---|---|---|
| Non-Core present | Diagnose: Lyme disease | Diagnose: not Lyme disease |
| Non-Core absent | Diagnose: not Lyme disease | Diagnose: not Lyme disease |

In one aspect, the disclosure provides a set of disease classifiers that are diagnostic for Lyme disease, wherein each classifier of the set comprises the same set of antibodies. In one aspect, the disclosure provides a set of disease classifiers that are diagnostic for Lyme disease, wherein each classifier of the set comprises a different set of antibodies. In one aspect, the disclosure provides a set of disease classifiers that are diagnostic for Lyme disease, wherein each classifier of the set comprises an overlap (partially) set of antibodies. In one aspect, the disclosure provides a set of disease classifiers that are diagnostic for Lyme disease, wherein each classifier of the set comprises an overlap (completely) set of antibodies.

In some embodiments, the disclosure provides for a set of reagents substance or mixture of substances capable of measuring the levels of biomarkers in a sample, wherein the biomarkers are an antibody capable of binding an antigen. In some embodiments, the reagents comprise, consist of or consist essentially of a reagent for sample preparation and/or analysis. In some embodiments, the reagents comprise, consist of or consist essentially of a capture reagents (such as antibodies), hybridization reagent, a purification reagent, an immobilization reagent, an imaging agent (detectable label described herein), blocking agents (e.g., proteins that block nonspecific binding), a buffer, processing reagent(s), anticoagulants (e.g., heparin, citrate, oxalate, EDTA, etc.), pH buffering components, salts, and preservatives (e.g., fluoride, iodoacetate, etc.) and any combinations thereof. The preprocessing reagents can serve to lyse cells, degrade unwanted molecules present in the sample and/or dilute sample for further processing. These processing reagents include, but are not limited to, surfactants and detergents, salts, cell lysing reagents, anticoagulants, degradative enzymes (e.g., proteases, lipases, nucleases, lipase, collagenase, cellulases, amylases and the like), and solvents, such as buffer solutions. Amount of the processing reagent to be added can depend on the particular sample to be analyzed, the time required for the sample analysis, identity of the bacterial infection to be detected or the amount of bacteria present in the sample to be analyzed.

In one embodiment, the disclosure provides a set of reagents (or array of reagents) to measure the expression levels of a panel or set of biomarkers in a fluid sample drawn from a patient, such as blood, serum, plasma, lymph, cerebrospinal fluid, ascites or urine. The reagents in a further embodiment are a multianalyte panel assay comprising reagents to evaluate the expression levels of these biomarker panels.

Development of Reference Standards. For each antigen utilized in the assays described herein, an antibody used as a reference standard will be included. The antibodies will comprise, consist of or consist essentially of monoclonal antibodies selected by specific binding to the antigen of interest. Each monoclonal will be humanized by grafting the rodent (mouse) complementarity determining region (CDR) onto a human antibody framework, including both IgM and IgG isotypes. These antibodies will be used in specific concentrations in the assay kit described herein to validate the function of each biomarker in the assay kit (i.e. as a reference standard). These antibodies may also be used in different concentrations to develop a standard curve, allowing for the quantification of antibody level from a human patient using the assay kit described herein.

Statistical Analysis

In certain instances, the statistical algorithm or statistical analysis is a learning statistical classifier system. As used herein, the term "learning statistical classifier system" includes a machine learning algorithmic technique capable of adapting to complex data sets (e.g., panel of markers of interest and/or list of Lyme disease-related symptoms) and making decisions based upon such data sets. The learning statistical classifier system can be selected from the group consisting of a random forest (RF), classification and regression tree (C&RT boosted tree, neural network (NN), support vector machine (SVM), general chi-squared automatic interaction detector model, interactive tree, multiadaptive regression spline, machine learning classifier, and combinations thereof. Preferably, the learning statistical classifier system is a tree-based statistical algorithm (e.g., RF, C&RT, etc.) and/or a NN (e.g., artificial NN, etc.). In certain embodiments, the methods comprise classifying a sample from the subject as a Lyme disease sample or non-Lyme disease sample (e.g., sample from a healthy control).

In certain instances, the statistical algorithm is a single learning statistical classifier system. Preferably, the single learning statistical classifier system comprises a tree-based statistical algorithm such as a RF or C&RT. As a non-limiting example, a single learning statistical classifier system can be used to classify the sample as an Lyme disease sample or non-Lyme disease sample (e.g., healthy control) based upon a prediction or probability value and the presence or level of at least one diagnostic marker (i.e., diagnostic marker profile comprising, consisting of, or consisting essentially of an antibody marker profile), alone or in combination with the presence or severity of at least one symptom (i.e., symptom profile such as Patient presents to provider with symptoms such as: tick bite, skin rash, or other clinical symptoms including headache, fever, chills, fatigue, myalgias, and arthralgias). The use of a single learning statistical classifier system typically classifies the sample as an Lyme disease sample with a sensitivity, specificity, positive predictive value, negative predictive value, and/or overall accuracy of at least about 60%, 65%, 70%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%. As such, the classification of a sample as a Lyme disease sample or non-Lyme disease sample is useful for aiding in the diagnosis of Lyme disease in a subject.

In certain other instances, the statistical algorithm is a combination of at least two learning statistical classifier systems. Preferably, the combination of learning statistical classifier systems comprises a RF and a NN, e.g., used in tandem or parallel. As a non-limiting example, a RF can first be used to generate a prediction or probability value based upon the diagnostic marker profile, alone or in combination with a symptom profile, and a NN can then be used to classify the sample as a Lyme disease sample or non-Lyme disease sample based upon the prediction or probability value and the same or different diagnostic marker profile or combination of profiles. Advantageously, the hybrid RF/NN learning statistical classifier system disclosed herein classifies the sample as an Lyme disease sample with a sensitivity, specificity, positive predictive value, negative predictive value, and/or overall accuracy of at least about 60%, 65%, 70%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%. In a particularly preferred embodiment, the statistical algorithm is a random forest classifier or a combination of a random forest classifier and a neural network classifier.

In some embodiments, the methods disclosed herein are 60%, 65%, 70%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% accurate across all stages of Lyme disease. In some embodiments, the methods disclosed herein are 90% accurate across all stages of Lyme disease: early Lyme disease, early disseminated Lyme disease, late disseminated Lyme disease, acute Lyme disease, and post-treatment Lyme disease.

In some embodiments, the methods disclosed herein have a sensitivity of 92% and specificity of 91% across all stages of Lyme disease: early Lyme disease, early disseminated Lyme disease, late disseminated Lyme disease, acute Lyme disease, and post-treatment Lyme disease. In some embodiments, the methods disclosed herein are more than 9 out of 10 patients will get the correct diagnosis of Lyme disease. In some embodiments, the methods disclosed herein are capable of diagnosing early Lyme disease, early disseminated Lyme disease, late disseminated Lyme disease, acute Lyme disease, and/or post-treatment Lyme disease.

In some instances, the data obtained from using the learning statistical classifier system or systems can be processed using a processing algorithm. Such a processing algorithm can be selected, for example, from the group consisting of a multilayer perceptron, backpropagation network, and Levenberg-Marquardt algorithm. In other instances, a combination of such processing algorithms can be used, such as in a parallel or serial fashion.

The various statistical methods and models described herein can be trained and tested using a cohort of samples from healthy individuals and Lyme disease patients. For example, samples from patients diagnosed by a physician as having Lyme disease or a clinical subtype thereof are suitable for use in training and testing the statistical methods and models disclosed herein. Samples from healthy individuals can include those that were not identified as Lyme disease samples. One skilled in the art will know of additional techniques and diagnostic criteria for obtaining a cohort of patient samples that can be used in training and testing the statistical methods and models disclosed herein.

In some embodiments, the diagnostic model includes evaluating the patient for the presence or severity of at least one symptom such as the patient presents to provider with symptoms such as: tick bite, skin rash, or other clinical symptoms including headache, fever, chills, fatigue, myalgias, and arthralgias.

In some embodiments, the patient sample is obtained by a standard blood draw which is performed and sent to a clinical laboratory for testing.

In some embodiments, the provider (doctor, clinician, healthcare worker) receives test results within 24-48 hours, prescribes appropriate treatment or orders additional tests for other diseases.

In some embodiments, the methods disclosed here are able to diagnose Lyme disease within the first 14 days of infection. In some embodiments, the methods disclosed here are able to diagnose Lyme disease within the first 14 days of infection with 92% accuracy.

Methods for Predicting Lyme Disease with Aid of Machine Learning Models.

A method for predicting Lyme disease with the aid of machine learning models includes: (A) providing antibody data to perform an eXtreme Gradient Boosting (XGBoost) regression algorithm for obtaining a XGBoost prediction value; (B) providing the antibody data to perform a Permutation test (PT) algorithm for obtaining an PT prediction value; (C) combining the antibody data, the XGBoost prediction value and the PT prediction value to generate Lyme disease combination data; (D) performing an XGBoost classification algorithm to obtain a suggestion for whether to issue a positive or negative detection result; and (E) performing the XGBoost regression algorithm on the Lyme disease combination data to obtain a Lyme disease prediction value.

The main objective of the disclosure is to provide a method for predicting Lyme disease with the aid of machine learning models, by combining antibody data, an XGBoost regression algorithm, a PT algorithm, and an XGBoost classification algorithm, in order to obtain reliable and correct prediction results.

In order to achieve the aforementioned objective, the disclosure provides a method for predicting Lyme disease in a subject with the aid of machine learning models. The method comprises: (A) providing antibody data for performing an eXtreme Gradient Boosting (XGBoost) regression algorithm in order to obtain a XGBoost prediction value; (B) providing the antibody data for performing a permutation test (PT) algorithm in order to obtain a PT prediction value; (C) combining the antibody data, the XGBoost prediction value and the PT prediction value to generate Lyme disease combination data; (D) performing an XGBoost classification algorithm to obtain a suggestion for whether to issue a positive or negative detection result; and (E) performing the XGBoost regression algorithm on the Lyme disease combination data to obtain a prediction value Lyme disease.

The antibody data in step (A) may comprise parameters such as detecting one or more antigens/antibody complexes formed when the sample (comprising, consisting of, or consisting essentially of antibody) is exposed to an antigen such as C6, GlpQ, p35, p66, OspC, DbpA, OppA2, ErpQ, OspE, and OspC2 and combinations thereof.

The Lyme disease combination data in step (C) may be generated by combining the antibody data, the XGBoost prediction value and the PT prediction value in the forms of vectors. As the antibody data, the XGBoost prediction value and the PT prediction value are all in the form of vectors, linking these vectors together may obtain characteristic vectors for second time machine learning.

The suggestion for whether to issue a positive or negative detection result in step (D) may comprise a positive or negative detection result value. When the antibody detection value (as determined by fluorescence value of the antibody/antigen complex or combination of fluorescence values from 2 or more different antibody/antigen complexes) exceeds a predetermined value, a result is sent indicating that the subject has Lyme disease. When the antibody detection value is lower than a predetermined value (as determined by fluorescence value of the antibody/antigen complex or combination of fluorescence values from 2 or more different antibody/antigen complexes), a result is sent indicating that the subject does not have Lyme disease.

Referring to FIG. 13A. The Method Comprises the Following Steps:

Step S201: Provide detection data for an array of antibody markers to perform an XGBoost regression algorithm to obtain an XGBoost prediction value.

Step S202: Provide detection data for an array of antibody markers, provide detection data for an array of antibody markers, to perform a permutation test to obtain a PT prediction value.

Step S203: Combine the detection data for an array of antibody markers, the XGBoost prediction value and the PT prediction value to generate Lyme disease combination data.

Step S204: Perform an XGBoost classification algorithm to obtain a suggestion for whether to issue a positive or negative detection result.

Step S205: Perform the XGBoost regression algorithm on the Lyme disease combination data to obtain a prediction value of infection.

FIG. 13B shows an example computer system that can implement methods provided herein. For example, the present disclosure provides computer systems that are programmed to implement methods of the disclosure in FIG. 13A. FIG. 13B shows a computer system 501 that is programmed or otherwise configured to analyze a sample. The computer system 501 can regulate various aspects of components of the system of the present disclosure. The computer system 501 can be an electronic device of a user or a computer system that is remotely located with respect to the electronic device. The electronic device can be a mobile electronic device.

The computer system 501 includes a central processing unit (CPU, also "processor" and "computer processor" herein) 505, which can be a single core or multi core processor, or a plurality of processors for parallel processing. The computer system 501 also includes memory or memory location 510 (e.g., random-access memory, read-only memory, flash memory), electronic storage unit 515 (e.g., hard disk), communication interface 520 (e.g., network adapter) for communicating with one or more other systems, and peripheral devices 525, such as cache, other memory, data storage and/or electronic display adapters. The memory 510, storage unit 515, interface 520 and peripheral devices 525 are in communication with the CPU 505 through a communication bus (solid lines), such as a motherboard. The storage unit 515 can be a data storage unit (or data repository) for storing data. The computer system 501 can be operatively coupled to a computer network ("network") 530 with the aid of the communication interface 520. The network 530 can be the Internet, an internet and/or extranet, or an intranet and/or extranet that is in communication with the Internet. The network 530 in some cases is a telecommunication and/or data network. The network 530 can include one or more computer servers, which can enable distributed computing, such as cloud computing. The network 530, in some cases with the aid of the computer system 501, can implement a peer-to-peer network, which may enable devices coupled to the computer system 501 to behave as a client or a server.

The CPU 505 can execute a sequence of machine-readable instructions, which can be embodied in a program or software. The instructions may be stored in a memory location, such as the memory 510. The instructions can be directed to the CPU 505, which can subsequently program or otherwise configure the CPU 505 to implement methods of the present disclosure. Examples of operations performed by the CPU 505 can include fetch, decode, execute, and writeback.

The CPU 505 can be part of a circuit, such as an integrated circuit. One or more other components of the system 501 can be included in the circuit. In some cases, the circuit is an application specific integrated circuit (ASIC).

The storage unit 515 can store files, such as drivers, libraries and saved programs. The storage unit 515 can store user data, e.g., user preferences and user programs. The computer system 501 in some cases can include one or more additional data storage units that are external to the computer system 501, such as located on a remote server that is in communication with the computer system 501 through an intranet or the Internet.

The computer system 501 can communicate with one or more remote computer systems through the network 530. For instance, the computer system 501 can communicate with a remote computer system of a user. Examples of remote computer systems include personal computers (e.g., portable PC), slates, or tablets (e.g., Apple® iPad, Samsung® Galaxy Tab), telephones, Smart phones (e.g., Apple® iPhone, Android-enabled device, Blackberry®), or personal digital assistants. The user can access the computer system 501 via the network 530.

"Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media (e.g., computer-readable media) include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 501 can include or be in communication with an electronic display 535 that comprises a user interface (UI) 540 for sample analysis. Examples of UIs include, without limitation, a graphical user interface (GUI) and web-based user interface. Methods and systems of the present disclosure can be implemented by way of one or more algorithms. An algorithm can be implemented by way of software upon execution by the central processing unit 505.

Methods as described herein can be implemented by way of machine (e.g., computer processor) executable code stored on an electronic storage location of the computer system 501, such as, for example, on the memory 510 or electronic storage unit 515. The machine executable or machine readable code can be provided in the form of software. During use, the code can be executed by the processor 505. In some cases, the code can be retrieved from the storage unit 515 and stored on the memory 510 for ready access by the processor 505. In some situations, the electronic storage unit 515 can be precluded, and machine-executable instructions are stored on memory 510.

The code can be pre-compiled and configured for use with a machine having a processor adapted to execute the code, or can be compiled during runtime. The code can be supplied in a programming language that can be selected to enable the code to execute in a pre compiled or as-compiled fashion.

Examples of the systems and methods provided herein, such as the computer system 501, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such as memory (e.g., read-only memory, random-access memory, flash memory) or a hard disk.

As another example, the computer storage media may be implemented using magnetic or optical technology. In such implementations, the program modules may transform the physical state of magnetic or optical media, when the software is encoded therein. These transformations may include altering the magnetic characteristics of particular locations within given magnetic media. These transformations may also include altering the physical features or characteristics of particular locations within given optical media, to change the optical characteristics of those locations. Other transformations of physical media are possible without departing from the scope of the present description, with the foregoing examples provided only to facilitate this discussion.

According to certain embodiments, the above-described data feeds may be stored in databases such as database servers that store master data as well as logging and trace information. The databases may also provide an API and/or API access (e.g., for open source) to the web server for data interchange based on JSON specifications. According to certain embodiments, the database servers may be optimally designed for storing large amounts of data, responding quickly to incoming requests, having a high availability and historizing master data.

Certain embodiments of the present disclosure are described above with reference to block and flow diagrams of systems and methods and/or computer program products according to example embodiments of the present disclosure. It will be understood that one or more blocks of the block diagrams and flow diagrams, and combinations of blocks in the block diagrams and flow diagrams, respectively, may be implemented by computer-executable program instructions. Likewise, some blocks of the block diagrams and flow diagrams may not necessarily need to be performed in the order presented, or may not necessarily need to be performed at all, according to some embodiments of the present disclosure.

These computer-executable program instructions may be loaded onto a general-purpose computer, a special-purpose computer, a processor (e.g., a processor chip, single/multi-processor architectures, sequential (Von Neumann)/parallel architectures, and specialized circuits, etc.), or other programmable data processing apparatus to produce a particular machine, such that the instructions that execute on the computer, processor, or other programmable data processing apparatus create means for implementing one or more functions specified in the flow diagram block or blocks. These computer program instructions may also be stored in a computer-readable memory that may direct a computer or other programmable data processing apparatus to function in a particular manner, such that the instructions stored in the computer-readable memory produce an article of manufacture including instruction means that implement one or more functions specified in the flow diagram block or blocks.

As an example, embodiments of the present disclosure may provide for a computer program product, including a computer-usable medium having a computer-readable program code or program instructions embodied therein, said computer-readable program code adapted to be executed to implement one or more functions specified in the flow diagram block or blocks. The computer program instructions may also be loaded onto a computer or other programmable data processing apparatus to cause a series of operational elements or steps to be performed on the computer or other programmable apparatus to produce a computer-implemented process such that the instructions that execute on the computer or other programmable apparatus provide elements or steps for implementing the functions specified in the flow diagram block or blocks.

Accordingly, blocks of the block diagrams and flow diagrams support combinations of means for performing the specified functions, combinations of elements or steps for performing the specified functions and program instruction means for performing the specified functions. It will also be understood that each block of the block diagrams and flow diagrams, and combinations of blocks in the block diagrams and flow diagrams, may be implemented by special-purpose, hardware-based computer systems that perform the specified functions, elements or steps, or combinations of special-purpose hardware and computer instructions.

Various aspects described herein may be implemented using standard programming and/or engineering techniques to produce software, firmware, hardware, and/or any combination thereof to control a computing device to implement the disclosed subject matter. A computer-readable medium may include, for example: a magnetic storage device such as a hard disk, a floppy disk or a magnetic strip; an optical storage device such as a compact disk (CD) or digital versatile disk (DVD); a smart card; and a flash memory device such as a card, stick or key drive, or embedded component. Additionally, it should be appreciated that a carrier wave may be employed to carry computer-readable electronic data including those used in transmitting and receiving electronic data such as streaming video or in accessing a computer network such as the Internet or a local area network (LAN). Of course, a person of ordinary skill in the art will recognize many modifications may be made to this configuration without departing from the scope or spirit of the claimed subject matter.

The disclosure can be further understood by the following numbered paragraphs:

Paragraph 1. A computer-implemented method for analyzing a sample, comprising:

providing detection data for an array of antibody markers;

performing a classification algorithm using at least a machine learning model trained to categorize samples based on the of the signal signatures for a plurality of antibodies bound to a plurality of antigens; and obtaining, using the machine learning model, a suggestion for whether to issue a positive or negative detection result.

Paragraph 2. A non-transitory computer-readable medium storing instructions that, when executed by a processor, perform a method for analyzing a sample, the method comprising:

detecting detection data for an array of antibody markers;

Performing a classification algorithm using at least a machine learning model trained to categorizing samples based on the of the signal signatures for a plurality of antibodies bound to a plurality of antigens;

obtaining, using the machine learning model, a suggestion for whether to issue a positive or negative detection result Paragraph 3. A system for analyzing a sample, the system comprising:

(a) a memory storing instructions;

(b) a processor configured to execute the instructions to:

detect detection data for an array of antibody markers;

Perform a classification algorithm using at least a machine learning model trained to categorizing samples based on the of the signal signatures for a plurality of antibodies bound to a plurality of antigens;

obtain, using the machine learning model, a suggestion for whether to issue a positive or negative detection result Paragraph 4. A computer-implemented method for analyzing a sample, comprising:

computationally classifying, using at least a machine learning model trained to categorize sample based on detection data for an array of antibodies; and assigning, using at least the machine learning model, a label to measured detection data corresponding to the disease state of the sample.

Biomarker Panels

The biomarker panels and associated methods and products were identified through the analysis of analyte levels of various molecular species in human blood serum drawn from subjects having Lyme disease of various stages, subjects having non-healthy non-Lyme control and healthy control.

To practice the methods of the present invention, appropriate cut-off levels for each of the biomarker analytes must be determined for Lyme disease samples in comparison with control samples. It is preferred that at least about 40 Lyme disease samples and 40 healthy control samples be used for this purpose, preferably case matched by age, sex and gender. Larger sample sets are preferred. A person skilled in the art would measure the level of each biomarker in the selected biomarker panel and then use an algorithm to compare the level of analytes in the Lyme disease samples with the level of analytes in the control samples. In this way, a predictive profile can be prepared based on informative cutoffs for the relevant disease type. The use of a separate validation set of samples is preferred to confirm the cut-off values so determined. Case and control samples can be obtained by obtaining consented (or anonymized) samples in a clinical trial or from repositories. Samples obtained in multiple sites are also preferred.

The results of analysis of patients' specimens using the disclosed predictive biomarker panels may be output for the benefit of the user or diagnostician, or may otherwise be displayed on a medium such as, but not limited to, a computer screen, a computer readable medium, a piece of paper, or any other visible medium.

EMBODIMENTS

The methods can further be understood by the following numbered paragraphs:

Paragraph 1: A method for aiding in the diagnosis of Lyme disease in a subject, said method comprising, consisting of, or consisting essentially of:

a. measuring the level of an antibody marker in a biological sample taken from the subject, wherein the antibody marker binds an antigen, the antigen selected from one or more of C6, GlpQ, p35, p66, OspC, DbpA, OppA2, ErpQ, OspE, OspC2, b. applying a first classification method to generate a first classification result for a first antibody marker;

c. applying a second classification method to generate a second classification result for a first antibody marker;

d. generating an antibody marker portrait based on the first classification result and second classification result; and e. comparing said antibody marker portrait to a diagnostic model to determine whether the individual has an increased likelihood of having Lyme disease compared to being a healthy control.

1. The method of paragraph 1, wherein the first classification result for a first antibody marker is based on fluorescence levels of IgG and the second classification result for a first antibody marker is based on fluorescence levels of IgM.

2. The method of any preceding paragraph, wherein the first classification method is based on fluorescence levels of one or more of C6/IgG; p35/IgG; p66/IgG; OspC/IgG; DbpA/IgG; OppA2/IgG; ErpQ/IgG; OspE/IgG; OspC2/IgG.

3. The method of any preceding paragraph, wherein the second classification method is based on fluorescence levels of one or more of C6/IgM; p35/IgM; p66/IgM; OspC/IgM; DbpA/IgM; OppA2/IgM; ErpQ/IgM; OspE/IgM; OspC2/IgM.

4. The method of any preceding paragraph, wherein the first and second classification method are not based on fluorescence levels of OspA/gG or OspA/IgM.

4.1 The method of any preceding paragraph, wherein the first and second classification method are not based on fluorescence levels of ErpQ/IgG or ErpQ/IgM.

4.2 The method of any preceding paragraph, wherein the first and second classification method are not based on fluorescence levels of BBJ09/IgG or BBJ09/IgM.

4.3 The method of any preceding paragraph, wherein the first and second classification method are not based on fluorescence levels of BB-A68/IgG or BB-A68/IgM.

4.3 The method of any preceding paragraph, wherein the first and second classification method are not based on fluorescence levels of GlpQ/IgG or GlpQ/IgM.

4.4 The method of any preceding paragraph, wherein if the first classification result for C6/IgG has a fluorescence level of greater than or equal to about 298 and if the second classification result for C6/IgM has a fluorescence level of greater than or equal to about 2645, the sample is classified as being positive for Lyme disease.

5. The method of any preceding paragraph, wherein if the first classification result for OspC/IgG has a fluorescence level of greater than or equal to about 436, the sample is classified as being positive for Lyme disease and/or if the second classification result for OspC/IgM has a fluorescence level of greater than or equal to about 400, the sample is classified as being positive for Lyme disease.

6. The method of any preceding paragraph, wherein if the first classification result for OspE/IgG has a fluorescence level of greater than or equal to about 305, the sample is classified as being positive for Lyme disease and/or if the second classification result for OspE/IgM has a fluorescence level of greater than or equal to about 293.8, the sample is classified as being positive for Lyme disease.

7. The method of any preceding paragraph, wherein if the first classification result for OppA2/IgG has a fluorescence level of greater than or equal to about 531, the sample is classified as being positive for Lyme disease and/or if the second classification result for OppA2/IgM has a fluorescence level of greater than or equal to about 332.3, the sample is classified as being positive for Lyme disease.

8. The method of any preceding paragraph, wherein if the first classification result for OspC2/IgG has a fluorescence level of greater than or equal to about 167.5, the sample is classified as being positive for Lyme disease and/or if the second classification result for OspC2/IgM has a fluorescence level of greater than or equal to about 342, the sample is classified as being positive for Lyme disease.

9. The method of any preceding paragraph, wherein if the first classification result for Dbpa/IgG has a fluorescence level of greater than or equal to about 346, the sample is classified as being positive for Lyme disease and/or if the second classification result for Dbpa/IgM has a fluorescence level of greater than or equal to about 535, the sample is classified as being positive for Lyme disease.

10. The method of any preceding paragraph, wherein if the first classification result for ErpQ/IgG has a fluorescence level of greater than or equal to about 362, the sample is classified as being positive for Lyme disease and/or if the second classification result for ErpQ/IgM has a fluorescence level of greater than or equal to about 128, the sample is classified as being positive for Lyme disease.

11. The method of any preceding paragraph, wherein if the first classification result for p35/IgG has a fluorescence level of greater than or equal to about 686, the sample is classified as being positive for Lyme disease and/or if the second classification result for p35/IgM has a fluorescence level of greater than or equal to about 2350, the sample is classified as being positive for Lyme disease.

12. The method of any preceding paragraph, wherein if the first classification result for p66/IgG has a fluorescence level of greater than or equal to about 689, the sample is classified as being positive for Lyme disease and/or if the second classification result for p66/IgM has a fluorescence level of greater than or equal to about 497, the sample is classified as being positive for Lyme disease.

13. The method of any preceding paragraph, further comprising, consisting of, or consisting essentially of applying a first classification method to generate a first classification result for a second antibody marker; applying a second classification method to generate a second classification result for a second antibody marker; generating an antibody marker portrait based on the first classification result and second classification result for the first antibody marker and second antibody marker; and comparing said antibody marker portrait to a diagnostic model to determine whether the individual has an increased likelihood of having Lyme disease compared to being a healthy control.

14. The method of any preceding paragraph, wherein if the antibody marker profile has a combined fluorescence value of IgM greater than or equal to 899, and/or the combined fluorescence value of IgG is greater or equal to 5955, the subject is diagnosed as having Lyme disease.

EXAMPLES

Example 1. Methods Detecting Lyme Disease Using Antigens: OspA, DbpA, OppA2, OspC, C6, OspE, ErpQ, D35, p66, BB-A68 and BBJ09

Measuring Activity of Antigens

Antigens OspA, DbpA, OppA2, OspC, an OspC variant, C6, OspE, ErpQ, p35, p66, BB-A68 and BBJ09 were examined in this study. Each antigen is bound to a bead of different color/wavelength. To identify activity against these antigens, two antibodies were used, IgG and IgM. Antibody reactivity was measured in fluorescence values, after the antibodies bound the antigens. These values ranged from less than 100, to over 15,000. See FIGS. 14A and 14B. The fluorescence values can be affected by different testing conditions, including variations in reagents and physical properties of the testing equipment. To account for variations between tests, 2-3 positive controls (data from different patients known to be positive for Lyme disease with high reactivity to these antigens) were used to 'normalize' all other fluorescence values from each of their respective plates. E.g., if the largest average fluorescence value of the positive controls for OspA was 100, and sample 1 had an OspA fluorescence value of 50, the new sample 1 value would become 50/100=0.5 (fictional values used for demonstration, not real data). Monoclonal antibodies targeting OspA, OspC and OppA2 are also included on each plate to minimize and quantify variations. Non-normalized data is shown in FIGS. 1A, 1B, 2A, 2B, 3A, and 3B. Normalized data is shown in FIGS. 4A and 4B. See also FIGS. 11A-D for GlpQ/IgG data.

Training a Decision Tree Model

After normalization, data was used to train a decision tree model. Decision trees are a useful model for classification of samples in clinical studies such as this. Decision trees give discrete cutoff values (or a range of cutoff values) that can be used to define a series of 'rules' that lead to a likelihood of the sample belonging to some class.

In brief, a decision tree model is trained by iteratively examining each column of data (here the normalized fluorescence values, where each column corresponds to a different antigen-antibody combination). A measure of variation is calculated for each column—often the 'entropy' or 'uncertainty' of each column. High entropy data corresponds to high uncertainty in the data, i.e., the data is split relatively evenly between high and low values. The data is then split based on the highest entropy column of data, where 'high' values send you down one path, and the 'low' values send you down another. The samples are then examined, if the data has been perfectly separated into the correct classes (or separated to within a certain level of tolerance for incorrect classification), the algorithm is finished, and no further processing occurs. Otherwise, the same process occurs again—each subset of data is examined for the column of data with the highest entropy, the data subset is then split again into another 'branch' in the 'tree'. Every 'branch' corresponds to a cut-off value (or a range of cutoff values) for the current antigen-antibody combination. Eventually the data is either classified to the previously defined acceptable level of correctness, or the tree reaches the previously defined maximum number of splits, and the final tree is returned. Example decision trees are shown in FIGS. 5A and 5B.

The data are then finally classified with the final tree, and the overall effectiveness of the model can be calculated—usually in the form of a 'confusion matrix'. A confusion matrix is a measure of the different classes—the number of samples a model correctly classified, and the number it classified incorrectly. In the case of a binary classification scheme this is a 2×2 matrix. Various classifications using this scheme are shown below (See FIG. 6):

True Positives (the correct class was 'true', and the model identified it as true)

False Negatives (the correct class was true, but the model incorrectly identified it as 'false')

True Negative (the correct class was false, and the model identified it as 'false')

False Positives (the correct class was false, but the model incorrectly identified it as 'true')

The data was split into 'training' and 'testing' subsets of samples. 80% of the data were used for training, and 20% of the data was withheld to test the resulting model. Second, a strategy of cross validation was used. Briefly during the training of the model, the data is further split into subsets. One of those subsets is left out, and a model is trained from the remaining data. Metrics of accuracy are calculated for that model, on the unused subset. Then the model is trained again, this time leaving out a different subset, and trained on the rest. This is performed multiple times. The model with the best result is returned as the final model. Then that model is used to classify the remaining 20% of the data. Example decision matrices are shown in FIGS. 6A-6C.

This strategy was implemented using R v4.2.2. Decision tree models were implemented with the R package rpart v4.1.19, cross validation with caret v6.0-93.

Example 2. Materials and Methods

Production of Antigens

To detect antibody/antigen interactions, the following protocols were used: OspA, OspC, BBA68 and DbpA were produced as glutathione S-transferase (GST) fusion proteins by inserting the genes of interest into the pGex 4T-1 vector (GE Healthcare). The C6 and OspC peptides were synthesized by GenScript. OppA2 was produced as a glutathione S-transferase (GST) fusion protein by Biomatik, Inc. OspE, ErpQ p35 and p66 were also made as GST fusion proteins by GenScript.

Detection of Specific Antibodies and Controls

The magnetic bead cocktail was prepared with assay buffer to achieve 50 μl per well. After optimizing of the ratio was performed, the final bead counts per well were 2,000 for C6 and OspC peptides, 1,000 for DbpA, 1,000 for OspA, 1,000 for OspC, 1,000 for OspE, 1,000 for BBA68, 1,000 for p35, 1,000 for p66 and 1,000 for OppA2. After the beads were added to a 96-well plate, they were washed twice with 200 μl wash buffer using a BioPlex Pro wash station. Samples were prepared for each plate as follows: per well, 50 μl of primary antibody was diluted in sample diluent. Serum (human or monkey) was diluted 1:200, and the anti-C6 and anti-OspC monoclonal antibodies were diluted 1:1,000 (or as otherwise specified). Anti-OspA was diluted 1:100.

Anti-C6 monoclonal 4B10 was produced by Genemed Synthesis and was diluted to 1.0 mg/ml in PBS. The anti-OspC hybridoma (B5.1) was kindly provided by Robert Gilmore (Centers for Disease Control and Prevention [CDC]) and was used as a dialyzed, concentrated hybridoma supernatant at a concentration of 0.4 mg/ml. The anti-OspA (CB10) was supplied by Jorge Benach and used as a hybridoma supernatant (undiluted).

Following addition of the primary (sample) antibody, plates were sealed with light protecting sealer, shaken at 1,100 rpm for 30 s, and incubated for 1 h at 300 rpm at room temperature. Beads were washed three times with 100 μl wash buffer. The secondary (detection) antibody was diluted 1:1,000 in detection antibody buffer, and 25 μl was added to each well. Secondary antibodies (all from Southern Biotech, Inc.) used for detection included the following: goat anti-rhesus IgG (heavy- and light-chain [H+L])-phycoerythrin (PE) (catalog no. 6200-09); goat anti-mouse IgG (H+L) R-phycoerythrin (RPE), human absorbed (catalog no. 1031-09); goat anti-human IgG-PE (catalog no. 2040-09); and mouse anti-human IgM-PE (catalog no. 9020-09). Plates were sealed with light protecting sealer and shaken at 1,100 rpm for 30 s, followed by 1 h of incubation at 300 rpm at room temperature. Beads were washed 3 times with 100 μl wash buffer. Finally, 125 μl of sheath buffer (Bio-Rad) was added to each well and the plate was sealed with new tape followed by shaking at 1,100 rpm for 30 s. Plates were stored at 4° C. and were covered with aluminum foil until analysis. Typically, the assay was performed 1 day and analyzed the next day. Prior to analysis, plates were shaken at 1,100 rpm. Samples were read on a Bio-Plex 200 suspension array system and analyzed using Bio-Plex Manager v6.1 software (Bio-Rad Laboratories).

Example 3. Multi-Antigen Diagnostic Test (5-Plex)

A multi-antigen diagnostic test that utilized the antigens OspA, OspC, DbpA, OppA-2 and C6 (5-plex) provided increased accuracy and specificity in diagnosing Lyme disease. The diagnostic test is carried out through an indirect antibody detection method. The antigen of interest is coupled to fluorometric beads. Binding of specific antibodies to the antigen of interest is detected by a secondary antibody that is conjugated to a fluorophore.

As shown in FIG. 9, using this 5-plex, there is improved performance over two-tier for Post-Treatment Lyme Disease Patients. The two tier assessment comprised an ELISA assay followed by a Western Blot assay for various antigens. FIGS. 8A and 8B show the diagnostic performance (specificity and sensitivity) of the antigens OppA2 (FIG. 8A) and C6 (FIG. 8B) relative to controls in diagnosing Post-Treatment Lyme Disease.

Example 4. Single Antigen Studies

Single antigen studies were performed on 312 samples. The samples were derived from the following patients:

11 look-a-like diseases (fibromyalgia, Rheumatoid arthritis, syphilis, multiple sclerosis, periodontitis)

140 healthy controls 109 confirmed Lyme Disease 52 early acute Lyme disease (tick bite and bulls-eye rash, 1-14 days post infection)

The antigens OspA, OspC, OspE, Oppa2, OspCV2, C6, Dbpa, ErpQ, p35, p66, BB-A68, and BB-J09 were each examined individually. Activity against these antigens was measured using two antibodies, IgG and IgM. Measuring antigen activity levels was determined using the protocol described under "Measuring Activity in Antigens" in Example 1.

Different fluorescence cutoff values were used for each antigen/antibody binding interaction (see below where the test of each antigen is described), to classify the sample as positive for Lyme disease or negative for Lyme disease.

Testing of OspA

Each of the 312 samples were tested for OspA activity. OspA activity in samples was measured using two classification methods: (1) fluorescence levels of OspA/IgG and (2) fluorescence levels of OspA/IgM. Fluorescence levels were determined using the protocol under "Measuring Activity of Antigens" described in Example 1. For classification method (1), a fluorescence level of greater than or equal to 333 resulted in a classification of the sample being positive for Lyme disease. For classification method (2), a fluorescence level of greater than or equal to 485 resulted in a classification of the sample being positive for Lyme disease.

Below, the results are shown for classification method (1) and classification method (2). In each classification method, each of the 247 tested samples were analyzed to determine if it was a true positive (TP), false positive (FP), true negative (TN), of false negative (FN). The data set was then analyzed to determine sensitivity, specificity, and accuracy of the test. Classification method (2) uses the XGBoost as described herein.

Results of Classification Method (1)

Table 1 shows the number of true positives, false positives, true negatives, and false negatives for the 247 samples tested for OspA activity using classification method (1). Table 2 shows the sensitivity, specificity, and accuracy of the data set.

TABLE 1

| True Positives (TP) | 63 |
| False Positives (FP) | 66 |
| True Negatives (TN) | 85 |
| False Negatives (FN) | 33 |

TABLE 2

| Sensitivity | 0.71875 |
| Specificity | 0.549668874172185 |
| Accuracy | 0.615384615384615 |

Results of Classification Method (2)

Table 3 shows the number of true positives, false positives, true negatives, and false negatives for the 247 samples tested for OspA activity using classification method (2). Table 4 shows the sensitivity, specificity, and accuracy of the data set.

TABLE 3

| True Positives (TP) | 72 |
| False Positives (FP) | 70 |
| True Negatives (TN) | 30 |
| False Negatives (FN) | 42 |

TABLE 4

| Sensitivity | 0.631578947368421 |
| Specificity | 0.3 |
| Accuracy | 0.476635514018692 |

Testing of OspC

Each of the 247 samples were tested for OspC activity. OspC activity in samples was measured using two classification methods: (1) fluorescence levels of OspC/IgG and (2) fluorescence levels of OspC/IgM. For classification method (1), a fluorescence level of greater than or equal to 436 resulted in a classification of the sample being positive for Lyme disease. For classification method (2), a fluorescence level of greater than or equal to 400 resulted in a classification of the sample being positive for Lyme disease.

Below, the results are shown for classification method (1) and classification method (2). In each classification method, each of the 247 tested samples were analyzed to determine if it was a true positive (TP), false positive (FP), true negative (TN), of false negative (FN). The data set was then analyzed to determine sensitivity, specificity, and accuracy of the test.

Results of Classification Method (1)

Table 5 shows the number of true positives, false positives, true negatives, and false negatives for the 247 samples tested for OspC activity using classification method (1). Table 6 shows the sensitivity, specificity, and accuracy of the data set.

TABLE 5

| True Positives (TP) | 79 |
| False Positives (FP) | 58 |
| True Negatives (TN) | 93 |
| False Negatives (FN) | 17 |

TABLE 6

| Sensitivity | 0.822916666666667 |
| Specificity | 0.615894039735099 |
| Accuracy | 0.696356275303644 |

Results of Classification Method (2)

Table 7 shows the number of true positives, false positives, true negatives, and false negatives for the 247 samples tested for OspC activity using classification method (2). Table 8 shows the sensitivity, specificity, and accuracy of the data set.

TABLE 7

| True Positives (TP) | 89 |
| False Positives (FP) | 53 |
| True Negatives (TN) | 47 |
| False Negatives (FN) | 25 |

TABLE 8

| Sensitivity | 0.780701754385965 |
| Specificity | 0.47 |
| Accuracy | 0.635514018691589 |

Testing of OspE

Each of the 247 samples were tested for OspE activity. OspE activity in samples was measured using two classification methods: (1) fluorescence levels of OspE/IgG and (2) fluorescence levels of OspE/IgM. For classification method (1), a fluorescence level of greater than or equal to 305 resulted in a classification of the sample being positive for Lyme disease. For classification method (2), a fluorescence level of greater than or equal to 293.8 resulted in a classification of the sample being positive for Lyme disease.

Below, the results are shown for classification method (1) and classification method (2). In each classification method, each of the 247 tested samples were analyzed to determine if it was a true positive (TP), false positive (FP), true negative (TN), of false negative (FN). The data set was then analyzed to determine sensitivity, specificity, and accuracy of the test.

Results of Classification Method (1)

Table 9 shows the number of true positives, false positives, true negatives, and false negatives for the 247 samples tested for OspE activity using classification method (1). Table 10 shows the sensitivity, specificity, and accuracy of the data set.

TABLE 9

| True Positives (TP) | 82 |
| False Positives (FP) | 47 |
| True Negatives (TN) | 104 |
| False Negatives (FN) | 14 |

TABLE 10

| Sensitivity | 0.854166666666667 |
| Specificity | 0.688741721854305 |
| Accuracy | 0.753036437246964 |

Results of Classification Method (2)

Table 11 shows the number of true positives, false positives, true negatives, and false negatives for the 247 samples tested for OspE activity using classification method (2). Table 12 shows the sensitivity, specificity, and accuracy of the data set.

TABLE 11

| True Positives (TP) | 86 |
| False Positives (FP) | 56 |
| True Negatives (TN) | 44 |
| False Negatives (FN) | 28 |

TABLE 12

| Sensitivity | 0.754385964912281 |
| Specificity | 0.44 |
| Accuracy | 0.607476635514019 |

Testing of Oppa2

Each of the 247 samples were tested for Oppa2 activity. Oppa2 activity in samples was measured using two classification methods: (1) fluorescence levels of Oppa2/IgG and (2) fluorescence levels of Oppa2/IgM. For classification method (1), a fluorescence level of greater than or equal to 531 resulted in a classification of the sample being positive for Lyme disease. For classification method (2), a fluorescence level of greater than or equal to 332.3 resulted in a classification of the sample being positive for Lyme disease.

Below, the results are shown for classification method (1) and classification method (2). In each classification method, each of the 247 tested samples were analyzed to determine if it was a true positive (TP), false positive (FP), true negative (TN), of false negative (FN). The data set was then analyzed to determine sensitivity, specificity, and accuracy of the test.

Results of Classification Method (1)

Table 13 shows the number of true positives, false positives, true negatives, and false negatives for the 247 samples tested for Oppa2 activity using classification method (1). Table 14 shows the sensitivity, specificity, and accuracy of the data set.

TABLE 13

| True Positives (TP) | 84 |
| False Positives (FP) | 53 |
| True Negatives (TN) | 98 |
| False Negatives (FN) | 12 |

TABLE 14

| Sensitivity | 0.875 |
| Specificity | 0.649006622516556 |
| Accuracy | 0.736842105263158 |

Results of Classification Method (2)

Table 15 shows the number of true positives, false positives, true negatives, and false negatives for the 247 samples tested for Oppa2 activity using classification method (2). Table 16 shows the sensitivity, specificity, and accuracy of the data set.

TABLE 15

| True Positives (TP) | 88 |
| False Positives (FP) | 54 |
| True Negatives (TN) | 46 |
| False Negatives (FN) | 26 |

TABLE 16

| Sensitivity | 0.771929824561403 |
| Specificity | 0.46 |
| Accuracy | 0.626168224299065 |

Testing of OspCV2

Each of the 247 samples were tested for OspCV2 activity, OspCV2 activity in samples was measured using two classification methods: (1) fluorescence levels of OspCV2/IgG and (2) fluorescence levels of OspCV2/IgM. For classification method (1), a fluorescence level of greater than or equal to 167.5 resulted in a classification of the sample being positive for Lyme disease. For classification method (2), a fluorescence level of greater than or equal to 342 resulted in a classification of the sample being positive for Lyme disease.

Below, the results are shown for classification method (1) and classification method (2). In each classification method, each of the 247 tested samples were analyzed to determine if it was a true positive (TP), false positive (FP), true negative (TN), of false negative (FN). The data set was then analyzed to determine sensitivity, specificity, and accuracy of the test.

Results of Classification Method (1)

Table 17 shows the number of true positives, false positives, true negatives, and false negatives for the 247 samples tested for OspCV2 activity using classification method (1). Table 18 shows the sensitivity, specificity, and accuracy of the data set.

TABLE 17

| True Positives (TP) | 91 |
| False Positives (FP) | 46 |
| True Negatives (TN) | 105 |
| False Negatives (FN) | 5 |

TABLE 18

| | |
|---|---|
| Sensitivity | 0.947916666666667 |
| Specificity | 0.695364238410596 |
| Accuracy | 0.793522267206478 |

Results of Classification Method (2)

Table 19 shows the number of true positives, false positives, true negatives, and false negatives for the 247 samples tested for OspCV2 activity using classification method (2). Table 20 shows the sensitivity, specificity, and accuracy of the data set.

TABLE 19

| | |
|---|---|
| True Positives (TP) | 89 |
| False Positives (FP) | 53 |
| True Negatives (TN) | 47 |
| False Negatives (FN) | 25 |

TABLE 20

| | |
|---|---|
| Sensitivity | 0.780701754385965 |
| Specificity | 0.47 |
| Accuracy | 0.635514018691589 |

Testing of C6

Each of the 247 samples were tested for C6 activity. C6 activity in samples was measured using two classification methods: (1) fluorescence levels of C6/IgG and (2) fluorescence levels of C6/IgM. For classification method (1), a fluorescence level of greater than or equal to 298 resulted in a classification of the sample being positive for Lyme disease. For classification method (2), a fluorescence level of greater than or equal to 2645 resulted in a classification of the sample being positive for Lyme disease.

Below, the results are shown for classification method (1) and classification method (2). In each classification method, each of the 247 tested samples were analyzed to determine if it was a true positive (TP), false positive (FP), true negative (TN), of false negative (FN). The data set was then analyzed to determine sensitivity, specificity, and accuracy of the test.

Results of Classification Method (1)

Table 21 shows the number of true positives, false positives, true negatives, and false negatives for the 247 samples tested for C6 activity using classification method (1). Table 22 shows the sensitivity, specificity, and accuracy of the data set.

TABLE 21

| | |
|---|---|
| True Positives (TP) | 89 |
| False Positives (FP) | 48 |
| True Negatives (TN) | 103 |
| False Negatives (FN) | 7 |

TABLE 22

| | |
|---|---|
| Sensitivity | 0.927083333333333 |
| Specificity | 0.682119205298013 |
| Accuracy | 0.777327935222672 |

Results of Classification Method (2)

Table 23 shows the number of true positives, false positives, true negatives, and false negatives for the 247 samples tested for C6 activity using classification method (2). Table 24 shows the sensitivity, specificity, and accuracy of the data set.

TABLE 23

| | |
|---|---|
| True Positives (TP) | 86 |
| False Positives (FP) | 56 |
| True Negatives (TN) | 44 |
| False Negatives (FN) | 28 |

TABLE 24

| | |
|---|---|
| Sensitivity | 0.754385964912281 |
| Specificity | 0.44 |
| Accuracy | 0.607476635514019 |

Testing of Dbpa

Each of the 247 samples were tested for Dbpa activity. Dbpa activity in samples was measured using two classification methods: (1) fluorescence levels of Dbpa/IgG and (2) fluorescence levels of Dbpa/IgM. For classification method (1), a fluorescence level of greater than or equal to 346 resulted in a classification of the sample being positive for Lyme disease. For classification method (2), a fluorescence level of greater than or equal to 535 resulted in a classification of the sample being positive for Lyme disease.

Below, the results are shown for classification method (1) and classification method (2). In each classification method, each of the 247 tested samples were analyzed to determine if it was a true positive (TP), false positive (FP), true negative (TN), of false negative (FN). The data set was then analyzed to determine sensitivity, specificity, and accuracy of the test.

Results of Classification Method (1)

Table 25 shows the number of true positives, false positives, true negatives, and false negatives for the 247 samples tested for Dbpa activity using classification method (1). Table 26 shows the sensitivity, specificity, and accuracy of the data set.

TABLE 25

| | |
|---|---|
| True Positives (TP) | 83 |
| False Positives (FP) | 54 |
| True Negatives (TN) | 97 |
| False Negatives (FN) | 13 |

TABLE 26

| | |
|---|---|
| Sensitivity | 0.864583333333333 |
| Specificity | 0.642384105960265 |
| Accuracy | 0.728744939271255 |

Results of Classification Method (2)

Table 27 shows the number of true positives, false positives, true negatives, and false negatives for the 247 samples tested for Dbpa activity using classification method (2). Table 28 shows the sensitivity, specificity, and accuracy of the data set.

TABLE 27

| | |
|---|---|
| True Positives (TP) | 86 |
| False Positives (FP) | 56 |
| True Negatives (TN) | 44 |
| False Negatives (FN) | 28 |

TABLE 28

| | |
|---|---|
| Sensitivity | 0.754385964912281 |
| Specificity | 0.44 |
| Accuracy | 0.607476635514019 |

Testing of ErpQ

Each of the 247 samples were tested for ErpQ activity. ErpQ activity in samples was measured using two classification methods: (1) fluorescence levels of ErpQ/IgG and (2) fluorescence levels of ErpQ/IgM. For classification method (1), a fluorescence level of greater than or equal to 362 resulted in a classification of the sample being positive for Lyme disease. For classification method (2), a fluorescence level of greater than or equal to 128 resulted in a classification of the sample being positive for Lyme disease.

Below, the results are shown for classification method (1) and classification method (2). In each classification method, each of the 247 tested samples were analyzed to determine if it was a true positive (TP), false positive (FP), true negative (TN), of false negative (FN). The data set was then analyzed to determine sensitivity, specificity, and accuracy of the test.

Results of Classification Method (1)

Table 29 shows the number of true positives, false positives, true negatives, and false negatives for the 247 samples tested for ErpQ activity using classification method (1). Table 30 shows the sensitivity, specificity, and accuracy of the data set.

TABLE 29

| | |
|---|---|
| True Positives (TP) | 63 |
| False Positives (FP) | 74 |
| True Negatives (TN) | 77 |
| False Negatives (FN) | 33 |

TABLE 30

| | |
|---|---|
| Sensitivity | 0.65625 |
| Specificity | 0.509933774834437 |
| Accuracy | 0.566801619433198 |

Results of Classification Method (2)

Table 31 shows the number of true positives, false positives, true negatives, and false negatives for the 247 samples tested for ErpQ activity using classification method (2). Table 32 shows the sensitivity, specificity, and accuracy of the data set.

TABLE 31

| | |
|---|---|
| True Positives (TP) | 87 |
| False Positives (FP) | 55 |
| True Negatives (TN) | 45 |
| False Negatives (FN) | 27 |

TABLE 32

| | |
|---|---|
| Sensitivity | 0.763157894736842 |
| Specificity | 0.45 |
| Accuracy | 0.616822429906542 |

Testing of D35

Each of the 247 samples were tested for p35 activity. P35 activity in samples was measured using two classification methods: (1) fluorescence levels of p35/IgG and (2) fluorescence levels of p35/IgM. For classification method (1), a fluorescence level of greater than or equal to 686 resulted in a classification of the sample being positive for Lyme disease. For classification method (2), a fluorescence level of greater than or equal to 2350 resulted in a classification of the sample being positive for Lyme disease.

Below, the results are shown for classification method (1) and classification method (2). In each classification method, each of the 247 tested samples were analyzed to determine if it was a true positive (TP), false positive (FP), true negative (TN), of false negative (FN). The data set was then analyzed to determine sensitivity, specificity, and accuracy of the test.

Results of Classification Method (1)

Table 33 shows the number of true positives, false positives, true negatives, and false negatives for the 247 samples tested for p35 activity using classification method (1). Table 34 shows the sensitivity, specificity, and accuracy of the data set.

TABLE 33

| | |
|---|---|
| True Positives (TP) | 59 |
| False Positives (FP) | 78 |
| True Negatives (TN) | 73 |
| False Negatives (FN) | 37 |

TABLE 34

| | |
|---|---|
| Sensitivity | 0.614583333333333 |
| Specificity | 0.483443708609272 |
| Accuracy | 0.534412955465587 |

Results of Classification Method (2)

Table 35 shows the number of true positives, false positives, true negatives, and false negatives for the 247 samples tested for p35 activity using classification method (2). Table 36 shows the sensitivity, specificity, and accuracy of the data set.

TABLE 35

| | |
|---|---|
| True Positives (TP) | 85 |
| False Positives (FP) | 57 |
| True Negatives (TN) | 43 |
| False Negatives (FN) | 29 |

TABLE 36

| | |
|---|---|
| Sensitivity | 0.745614035087719 |
| Specificity | 0.43 |
| Accuracy | 0.598130841121495 |

Testing of D66

Each of the 247 samples were tested for p66 activity. p66 activity in samples was measured using two classification methods: (1) fluorescence levels of p66/IgG and (2) fluorescence levels of p66/IgM. For classification method (1), a fluorescence level of greater than or equal to 689 resulted in a classification of the sample being positive for Lyme disease. For classification method (2), a fluorescence level of greater than or equal to 497 resulted in a classification of the sample being positive for Lyme disease.

Below, the results are shown for classification method (1) and classification method (2). In each classification method, each of the 247 tested samples were analyzed to determine if it was a true positive (TP), false positive (FP), true negative (TN), of false negative (FN). The data set was then analyzed to determine sensitivity, specificity, and accuracy of the test.

Results of Classification Method (1)

Table 37 shows the number of true positives, false positives, true negatives, and false negatives for the 247 samples tested for p66 activity using classification method (1). Table 38 shows the sensitivity, specificity, and accuracy of the data set.

TABLE 37

| | |
|---|---|
| True Positives (TP) | 85 |
| False Positives (FP) | 52 |
| True Negatives (TN) | 99 |
| False Negatives (FN) | 11 |

TABLE 38

| | |
|---|---|
| Sensitivity | 0.885416666666667 |
| Specificity | 0.655629139072848 |
| Accuracy | 0.744939271255061 |

Results of Classification Method (2)

Table 39 shows the number of true positives, false positives, true negatives, and false negatives for the 247 samples tested for p66 activity using classification method (2). Table 40 shows the sensitivity, specificity, and accuracy of the data set.

TABLE 39

| | |
|---|---|
| True Positives (TP) | 81 |
| False Positives (FP) | 61 |
| True Negatives (TN) | 39 |
| False Negatives (FN) | 33 |

TABLE 40

| | |
|---|---|
| Sensitivity | 0.710526315789474 |
| Specificity | 0.39 |
| Accuracy | 0.560747663551402 |

Testing of BB-A68

Each of the 247 samples were tested for BB-A68 activity. BB-A68 activity in samples was measured using two classification methods: (1) fluorescence levels of BB-A68/IgG and (2) fluorescence levels of BB-A68/IgM. For classification method (1), a fluorescence level of greater than or equal to 328 resulted in a classification of the sample being positive for Lyme disease. For classification method (2), a fluorescence level of greater than or equal to 387 resulted in a classification of the sample being positive for Lyme disease.

Below, the results are shown for classification method (1) and classification method (2). In each classification method, each of the 247 tested samples were analyzed to determine if it was a true positive (TP), false positive (FP), true negative (TN), of false negative (FN). The data set was then analyzed to determine sensitivity, specificity, and accuracy of the test.

Results of Classification Method (1)

Table 41 shows the number of true positives, false positives, true negatives, and false negatives for the 247 samples tested for BB-A68 activity using classification method (1). Table 42 shows the sensitivity, specificity, and accuracy of the data set.

TABLE 41

| | |
|---|---|
| True Positives (TP) | 84 |
| False Positives (FP) | 53 |
| True Negatives (TN) | 98 |
| False Negatives (FN) | 12 |

TABLE 42

| | |
|---|---|
| Sensitivity | 0.875 |
| Specificity | 0.649006622516556 |
| Accuracy | 0.736842105263158 |

Results of Classification Method (2)

Table 43 shows the number of true positives, false positives, true negatives, and false negatives for the 247 samples tested for BB-A68 activity using classification method (2). Table 44 shows the sensitivity, specificity, and accuracy of the data set.

TABLE 43

| | |
|---|---|
| True Positives (TP) | 77 |
| False Positives (FP) | 65 |
| True Negatives (TN) | 35 |
| False Negatives (FN) | 37 |

TABLE 44

| | |
|---|---|
| Sensitivity | 0.675438596491228 |
| Specificity | 0.35 |
| Accuracy | 0.523364485981308 |

Testing of BB-J09

Each of the 247 samples were tested for BB-J09 activity. BB-J09 activity in samples was measured using two classification methods: (1) fluorescence levels of BB-J09/IgG and (2) fluorescence levels of BB-J09/IgM. For classification method (1), a fluorescence level of greater than or equal to 642 resulted in a classification of the sample being positive for Lyme disease. For classification method (2), a fluorescence level of greater than or equal to 369 resulted in a classification of the sample being positive for Lyme disease.

Below, the results are shown for classification method (1) and classification method (2). In each classification method, each of the 247 tested samples were analyzed to determine if it was a true positive (TP), false positive (FP), true negative (TN), of false negative (FN). The data set was then analyzed to determine sensitivity, specificity, and accuracy of the test.

Results of Classification Method (1)

Table 45 shows the number of true positives, false positives, true negatives, and false negatives for the 247 samples tested for BB-J09 activity using classification method (1). Table 46 shows the sensitivity, specificity, and accuracy of the data set.

TABLE 45

| | |
|---|---|
| True Positives (TP) | 77 |
| False Positives (FP) | 60 |
| True Negatives (TN) | 91 |
| False Negatives (FN) | 19 |

TABLE 46

| Sensitivity | 0.802083333333333 |
|---|---|
| Specificity | 0.602649006622517 |
| Accuracy | 0.680161943319838 |

Results of Classification Method (2)

Table 47 shows the number of true positives, false positives, true negatives, and false negatives for the 247 samples tested for BB-J09 activity using classification method (2). Table 48 shows the sensitivity, specificity, and accuracy of the data set.

TABLE 47

| True Positives (TP) | 85 |
|---|---|
| False Positives (FP) | 57 |
| True Negatives (TN) | 43 |
| False Negatives (FN) | 29 |

TABLE 48

| Sensitivity | 0.745614035087719 |
|---|---|
| Specificity | 0.43 |
| Accuracy | 0.598130841121495 |

Example 5. Combined Antigen Studies

Combined antigen studies were performed 247 samples. The samples were derived from the following patients:
Disease control (DC):
Healthy Control (HC):
Lyme Disease (LD):
Lyme Disease Acute (LDA):

Activity of OspA, OspC, OspE, Oppa2, OspCV2, C6, Dbpa, ErpQ, p35, p66, BB-A68, and BB-J09 were measured using two antibodies, IgG and IgM. Measuring antigen activity levels was determined using the protocol under "Measuring Activity in Antigens" in Example 1. The fluorescence activity was measured using classification method (1) and classification method (2).

Under classification method (1), the combined fluorescence activity was measured of IgG/OspA, IgG/OspC, IgG/OspE, IgG/Oppa2, IgG/OspCV2, IgG/C6, IgG/Dbpa, IgG/ErpQ, IgG/p35, IgG/p66, IgG/BB-A68, and IgG/BB-J09. If the combined fluorescence value of each of these antibody/antigen interactions was greater than or equal to 5955, the sample was classified as positive for Lyme disease. If the combined fluorescence value of each of these antibody/antigen interaction was less than 5955, the sample was classified as negative for Lyme disease.

Under classification method (2), the combined fluorescence activity was measured of IgM/OspA, IgM/OspC, IgM/OspE, IgM/Oppa2, IgM/OspCV2, IgM/C6, IgM/Dbpa, IgM/ErpQ, IgM/p35, IgM/p66, IgM/BB-A68, and IgM/BB-J09. If the combined fluorescence value of each of these antibody/antigen interactions was greater than or equal to 899, the sample was classified as positive for Lyme disease. If the combined fluorescence value of each of these antibody/antigen interaction was less than 899, the sample was classified as negative for Lyme disease.

Results of Classification Method (1)

Table 49 shows the number of true positives, false positives, true negatives, and false negatives for the 247 samples tested using classification method (1). Table 50 shows the sensitivity, specificity, and accuracy of the data set.

TABLE 49

| True Positives (TP) | 84 |
|---|---|
| False Positives (FP) | 53 |
| True Negatives (TN) | 98 |
| False Negatives (FN) | 12 |

TABLE 50

| Sensitivity | 0.875 |
|---|---|
| Specificity | 0.649006622516556 |
| Accuracy | 0.736842105263158 |

Results of Classification Method (2)

Table 51 shows the number of true positives, false positives, true negatives, and false negatives for the 247 samples tested using classification method (2). Table 52 shows the sensitivity, specificity, and accuracy of the data set.

TABLE 51

| True Positives (TP) | 90 |
|---|---|
| False Positives (FP) | 52 |
| True Negatives (TN) | 48 |
| False Negatives (FN) | 24 |

TABLE 52

| Sensitivity | 0.789473684210526 |
|---|---|
| Specificity | 0.48 |
| Accuracy | 0.644859813084112 |

Example 6. Cross-Validation

Cross-validation studies were performed on the results from the combined antigen studies in Example 5.

Table 53 shows the number of true positives, false positives, true negatives, and false negatives of IgG fluorescence after cross-validation. Table 54 shows the sensitivity, specificity, and accuracy of the data set.

TABLE 53

| True Positives (TP) | 71 |
|---|---|
| False Positives (FP) | 19 |
| True Negatives (TN) | 132 |
| False Negatives (FN) | 25 |

TABLE 54

| Sensitivity | 0.739583333333333 |
|---|---|
| Specificity | 0.874172185430464 |
| Accuracy | 0.821862348178138 |

Table 55 shows the number of true positives, false positives, true negatives, and false negatives of IgM fluorescence after cross-validation. Table 56 shows the sensitivity, specificity, and accuracy of the data set.

TABLE 55

| True Positives (TP) | 75 |
|---|---|
| False Positives (FP) | 39 |
| True Negatives (TN) | 95 |
| False Negatives (FN) | 5 |

TABLE 56

| | |
|---|---|
| Sensitivity | 0.9375 |
| Specificity | 0.708955223880597 |
| Accuracy | 0.794392523364486 |

In the data provided there were 65 PTLDS cases (chronic) leaving a total of 312 total cases in the 'expanded cohort'. There are results from two distinct machine-learning classifiers to serve as an example. The first, used during development work, is an SVM (Support Vector Machines) binary classifier that was originally described by Vapnik and Chervonenkis in 1963. SVM transforms multiple features into higher dimensions to create a plane of separation called a hyperplane. That hyperplane is created to best separate the 'training' data. Here, the different antigens and the two immunoglobulins, IgG and IgM, are combined into one large dataset such that all antigens and both immunoglobulins are given to the SVM classifier. Based on the training data, the classifier decides where to draw the threshold in multidimensional space to best separate the training data. If the training data is sufficiently diverse and represents the diversity of the expected population of positive and negative disease cases, we expect all test data to provide the same performance as the training data. In the real world, this expectation is unlikely to be true as training datasets are limited by practicality. However, picking non-target-disease (Lyme) look-alike cases from similar febrile diseases challenges the classifier's specificity—this was done using both healthy controls and non-Lyme non-healthy controls. The classifier is trained on a subset of data, then tested on one or more held-out cases that the classifier never saw. The classifier predicts the health status of the held-out case(s) and if it matches the actual status of that person, that is a TP (for predicting Lyme positive in a Lyme case) or a TN (for predicting non-disease for a healthy or look-alike person).

The SVM method from the original data in the "combined SVM" tab from the "Lyme Final Report" file achieved a sensitivity of 0.90 and a specificity of 0.789 from a total of 150 test cases. This SVM was the simplest possible algorithm, written in 1994 and implemented in R using a 5-fold cross-validation and a p-value t-test to manually select 20 total features from both IgG and IgM. This is the most conservative test used during development to test feasibility. This old SVM algorithm is not suited for commercial use.

XGBoost (eXtreme Gradient Boosting) is a modern binary classifier introduced in 2014. It utilizes multiple decision trees that are built using weak learners (data that does not classify very well) to support mistakes made by strong learners (data that classifies by itself very well). This method uses as much data as possible to assess the diversity of the training set and better predict all cases by pruning tree branches through in a gradient manner, leaving branches with some supporting evidence un-pruned unless their support is outweighed by negative performance not covered by any other weak learner. This method is very widely used and has enormous commercial support.

An implementation of XGBoost as used in python (example shown below): data into features.

```
X=data.iloc[:, 1:−1]#Features
y=data['Class']#Labels
#Initialize XGBoost classifier
model=XGBClassifier( )
#Initialize 10-fold cross-validation
cv=StratifiedKFold(n_splits=10)
#Lists to store true positive rates, false positive rates, and
    thresholds
```

```
tpr_list=[ ]
fpr_list=[ ]
thresholds_list=[ ]
#Perform cross-validation
for train_index, test_index in cv.split(X, y):
X_train, X_test=X.iloc[train_index], X.iloc[test_index]
y_train, y_test=y.iloc[train_index], y.iloc[test_index]
``` we analyzed 312 patients including Hopkins PTLDS, DC, HC, LD and LDA-labeled patients using 4-fold cross-validation. When the full cohort was tested using a permutation test, we assessed AUC using 10-fold cross-validation (more stringent) and randomly swapped out the disease labels to show that the performance of the randomly-permuted labels is 50%, the AUC of the correctly labeled samples is ~0.88. Using 4-fold CV and XGBoost the results are as follows:

312-patients including PTLDS: Accuracy=0.9123, Sensitivity=0.9114, Specificity=0.9133

195 patients not including PTLDS: Accuracy=0.8769, Sensitivity=0.8182, Specificity=0.9000.

FIG. 12: The Area under the curve (AUC) is a combination of specificity and sensitivity demonstrating the combined performance of a diagnostic test. The XGBoost was trained and tested using 10-fold leave out for non-permuted labels and the same for permuted labels. The model was run 10,000 times. The average AUC was 0.8750. This method incorporates both IgG and IgM, and no feature-selection was done (all antigens were included, although the algorithm may choose to ignore the information-less ones).

| | Performance Stats PTLDS Included | Performance Stats no PTLDS |
|---|---|---|
| MCC | 0.8657123 | 0.730917655 |
| F1 | 0.9142857 | 0.789473684 |
| acc | 0.9123377 | 0.876923077 |
| FPR | 0.4814815 | 0.1 |
| TPR | 0.91 | 0.818181818 |
| FOR | 0.09 | 0.073529412 |
| FDR | 0.0828025 | 0.237288136 |
| sensitivity= | 0.9113924 | 0.818181818 |
| specificity= | 0.9133333 | 0.9 |
| PPV | 0.9171975 | 0.762711864 |
| NPV | 0.9072848 | 0.926470588 |
| FP | 13 | 14 |
| FN | 14 | 10 |
| TP | 144 | 45 |
| TN | 137 | 126 |
| Total patients | 308 | 195 |

Table X: Leave-One-Out Cross-validation of cohort with or without Hopkins-provided PTLDS cases.

Example 7. Combined Overlap of Cross-Validation Studies

The combined overlap of the cross-validation studies was assessed for the IgG and IgM antibodies. Table 57 shows the true positives, false positives, true negatives, and false negatives of this combined overlap. Table 58 shows the sensitivity, specificity, and accuracy of the data set.

TABLE 57

| | |
|---|---|
| True Positives (TP) | 84 |
| False Positives (FP) | 12 |
| True Negatives (TN) | 45 |
| False Negatives (FN) | 9 |

TABLE 58

| Sensitivity | 0.903225806451613 |
| Specificity | 0.789473684210526 |
| Accuracy | 0.86 |

Example 8. Verification Study

A total of 308 patient specimens were tested:
11 look-a-like diseases
140 healthy controls
105 clinically confirmed Lyme disease cases
52 early acute Lyme disease (tick bite and bulls-eye rash, 1-14 days post infection)
Table 59 shows the accuracy of the verification study.

| | Disease State | | |
| --- | --- | --- | --- |
| | Pos | Neg | Total |
| Pos | 144 | 13 | 157 |
| Neg | 14 | 137 | 151 |
| Total | 158 | 150 | 308 |

Sensitivity: 91.72%; Specificity: 90.73%; Accuracy: 91%

Samples used to determine the sensitivity of the disclosed methods were from patients with an EM rash, punch biopsy and/or PCR confirming infection. These would likely test negative with current serological assays that have less than 50% accuracy.

Significance of Verification Study Outcomes: Blood samples used in the verification study were obtained from the highly regarded Johns Hopkins Lyme Disease Research Center SLICE studies and from the CDC. The compositions and methods disclosed herein successfully differentiated Lyme disease from other infections caused by spirochetes (syphilis) and from "look-alike" diseases that Lyme patients are often misdiagnosed with (mononucleosis, multiple sclerosis, fibromyalgia, and rheumatoid arthritis). The compositions and methods disclosed herein correctly identified early Lyme disease cases that were confirmed by clinical diagnosis based on tick bite/skin rash. Standard serological tests for Lyme disease correctly identifies <30% of early Lyme cases.

Example 9. A Method for Aiding in the Diagnosis of Lyme Disease Using a Combination of Antibody Markers This example illustrates a method for aiding in the diagnosis of Lyme disease using a combination of antibody markers.

Antibodies against the bacterium *Borrelia burgdorferi sensu stricto* (e.g., C6, OspA; p35, p66, OspC, DbpA, OppA2, ErpQ; OspE, OspC2, BBJ09; and BB-A68) have been proven to be valuable biomarkers of Lyme disease. It was postulated that detecting a combination of these can be used to more accurately detect Lyme disease.

Methods: Provided herein is the development and validation of a method to aid in the diagnosis of Lyme disease by measuring the level of a first antibody and at least a second antibody in a sample from an individual, comparing the levels with control levels, and determining whether the individual has an increased likelihood of having Lyme disease. In this method, the serum levels of antibodies against antigens such as C6, OspA; p35, p66, OspC, DbpA, OppA2, ErpQ; OspE, OspC2, BBJ09; and BB-A68 can be measured in samples from healthy controls and patients with Lyme disease. A logistic regression machine learning algorithm can be performed with the data to select markers that are informative and predictive of a sample taken from a healthy control and an individual with Lyme disease.

The marker values for antibodies for the healthy control samples and the Lyme disease samples were calculated and analyzed by logistic regression modeling. The analysis generated an estimate for each marker which represents whether the level of the marker can predict Lyme disease. The estimate can have a positive value that signifies that the marker has a positive effect on the prediction of Lyme disease. An estimate with a larger positive value has a larger effect on discriminating Lyme disease. The estimate can have a large negative value that shows that the marker has a large negative effect on the prediction of Lyme disease. An estimate substantially close to 0 indicates that the marker does not contribute to the prediction of Lyme disease.

Example 10. Lyme Classifier

The Lyme disease cohort contains 12 antigens, two disease classes (Lyme N=160, not-Lyme N=150), 4 cohort groups (acute Lyme, persistent/chronic Lyme, healthy control non-healthy non-Lyme control). There are two methods by which a diagnosis can be made: first, select one of the 12 antigens, set a threshold above which a patient is called positive, below which a patient is called negative.

The second method is relying on the intensity of reactivity of multiple biomarkers simultaneously. FIG. 10 is a graphical representation of the fluorescence intensity per antigen and per patient for the IgG immunoglobulin fraction. The rows represent the 12 antigens, columns are patients. The patients on the left are negative, the patients on the right are positive. In some cases, the antigen provides little obvious class distinction (see p35) or consistent distinction (see OspA). Here, some patients are obviously reactive/positive, but not all. OspCV2 appears to be highly sensitive and selective, but in fact only achieves a sensitivity of 71.8%. In some density plots of the smoothed data from Lyme patients overlayed with non-Lyme patients clearly show almost no distinction between Lyme and non-Lyme. However, in some patients, those antigens with low sensitivity did in fact provide evidence of the disease when other more sensitive antigens did not. Each antigen has a certain level of performance individually, but it was determined that a combination of antigens enhanced the sensitivity and specificity of the diagnostic.

There are several methods of using ensemble properties of biomarkers to predict an outcome; herein XGBoost is used. The seminal paper "Greedy Function Approximation a Gradient Boosting Machine" (doi:10.1214/aos/1013203451) introduced gradient boosted trees, a supervised learning method where training data with multiple features is used to predict a target variable, usually a binary yes/no outcome, through complex interactions between and among the data. This learning method can typically outperform statistical classifiers or linear classifiers because a classification model is built, revised, optimized, and trimmed down to the most efficient and accurate relationship possible given the training and test data. Statistical and linear classifiers are not pruned or edited to remove non-supportive data relationships other than through feature selection and are therefore not as flexible when a classification requires a complex relationship among many variables. See FIG. 10 and FIGS. 11A-11D.

A tree-based ensemble model consists of a set of classification and regression trees (CART). Unlike standard tree approaches where a yes/no value is assigned to a leaf, XGBoost keeps the original antigen fluorescence values in each leaf, allowing that leaf to be ranked more realistically in its contribution to the whole model's performance. In the process of training the algorithm to predict patient outcome, a unique, independent tree is built from each antigen. Mixing the trees together brings every antigen into the solution. The training portion of the process builds error functions using simple mean squared error. These are no more than quadratic terms that become the goal of optimizing by leaf. During training, the real-world results are used to prune away terms that never contribute to the positive performance of the model. For some patients, pruning or boosting a term from the raw data to obtain an accurate diagnosis might cause two other patients to receive an incorrect diagnosis, so the optimizer selects the case where more patients receive a correct diagnosis, even at the expense of a single patient. The rank of each leaf's contribution to the entire model's performance is established iteratively, enabling the model to incorporate as many scenarios as possible (complete optimization). The pruning and boosting steps refine the performance of the model such that cross-validation of the training cases is optimized for both sensitivity and specificity.

To ensure there is no bias in the model building process we iteratively trained on randomly selected patients pulled from the entire dataset, split at the same ratio between case/control as the entire cohort. This conservative approach yielded an AUC of just below 90%, with 99-100% of the chronic patients called correctly each time.

Summary: The XGBoost method enables a set of features, in this case antigens, to be assessed for performance based on their learning ability. Some antigens for predicting Lyme disease would be removed from consideration as a diagnostic using standard frequentist statistics, a high p-value between case/control. These 'poor learners' are given a weight based on how well they classify each patient, not all patients, in a tree-based model building exercise. Any patient who was misclassified by an 'exceptional learner', that is an antigen that calls nearly every patient correctly, is given importance when evaluating poor learners. Any antigen that provides correct evaluation of a misclassified patient is ranked highly in that portion of the model that evaluates patients likely to be incorrectly diagnosed.

There are intermediate files produced by XGBoost that decompose the tree/leaf evaluation process, they cannot be interpreted without the context of the model. The model itself does not provide a step-by-step evaluation of each antigen for each patient because the prune/boost steps are only useful in the context of the ensemble performance of the many trees that are built. Therefore, only the cross-validation score is informative relative to the performance of the antigens, and every antigen contributes to the performance of the model.

The embodiments disclosed herein can be further understood by the following numbered paragraphs:

Paragraph 1: A method for aiding in the diagnosis of Lyme disease in a subject, said method comprising, consisting of, or consisting essentially of:

(a) measuring the level of an array of antibody markers in a biological sample taken from the subject, wherein the array comprises an antibody capable of binding OspC2, (b) applying a statistical analysis to the measured level of the array of antibody markers to generate an antibody marker profile; and (c) comparing said antibody marker profile to a diagnostic model to determine whether the individual has an increased likelihood of having Lyme disease compared to being a healthy control.

Paragraph 2: The method of Paragraph 1, wherein the array of antibody markers is capable of binding antigens selected from the group consisting of biomarkers against: OspC2, OspC, C6 and combination thereof.

The method of Paragraph 1, wherein the array of antibody markers is capable of binding antigens selected from the group consisting of biomarkers against: C6, GlpQ, p35, p66, OspC, DbpA, OppA2, ErpQ, OspE and combination thereof.

Paragraph 2A: The method of any preceding paragraph, wherein the antibody capable of binding OspC2 is IgG, IgM or both.

Paragraph 3: The method of any preceding paragraph, wherein the step of measuring the level of an array of antibody markers comprises:

contacting the sample with at least one antigen or an antigenic fragment thereof to transform the antibody present in the sample into a complex comprising, consisting of, or consisting essentially of the at least one antigen or the antigenic fragment thereof and the antibody;

contacting the complex with a detection antibody under conditions suitable to form a ternary complex comprising, consisting of, or consisting essentially of the at least one antigen or the antigenic fragment thereof, the antibody and the detection antibody;

and detecting the ternary complex which correlates to the level of at least one antibody marker.

Paragraph 4: The method of any preceding paragraph, wherein the statistical analysis transforms the level of the array of antibody markers into an antibody marker profile.

Paragraph 5: The method of any preceding paragraph, wherein if the antibody marker profile has a combined fluorescence value of IgM greater than or equal to 899, and/or the combined fluorescence value of IgG is greater or equal to 5955, the subject is diagnosed as having Lyme disease.

Paragraph 6: The method of any preceding paragraph, wherein the diagnostic model is established using a retrospective cohort with known outcomes of a clinical subtype of Lyme disease and healthy controls.

Paragraph 7. The method of Paragraph 6, wherein the antibody model is derived by applying logistic regression analysis to the level of one or more antibody markers determined in the retrospective cohort.

Paragraph 8: The method of any preceding paragraph, for the detection of Lyme disease at any stage: early Lyme disease, early disseminated Lyme disease, late disseminated Lyme disease, acute Lyme disease, and post-treatment Lyme disease.

Paragraph 9: The method of any preceding paragraph, wherein when the antibody marker profile has a combined fluorescence value of IgM greater than or equal to 899, and/or a combined fluorescence value of IgG greater or equal to 5955, the subject is diagnosed as having Lyme disease.

Paragraph 10: A method for aiding in the diagnosis of Lyme disease in a subject and treating the subject, said method comprising, consisting of, or consisting essentially of:

(a) measuring the level of an array of antibody markers in a biological sample taken from the subject, wherein the array is capable of binding OspC2, (b) applying a statistical analysis to the measured level of the array of antibody markers to generate an antibody marker profile;

(c) comparing said antibody marker profile to a diagnostic model to determine whether the individual has an increased likelihood of having Lyme disease compared to being a healthy control; and treating the subject determined to have Lyme disease.

The method of paragraph 10, further comprising, consisting of, or consisting essentially of treating the subject with any one or more of doxycycline, amoxicillin, azithromycin, penicillin G, cefotaxime, cefuroxime, and ceftriaxone.

Paragraph 11: A method, the method comprising, consisting of, or consisting essentially of:

contacting at least one antibody in a biological sample derived from a subject; detecting binding between the at least one antibody to at least one antigen in the sample, wherein the at least one antigen comprises: C6, GlpQ, p35, p66, OspC, DbpA, OppA2, ErpQ, OspE, and/or OspC2; and evaluating the reactivity to diagnose Lyme disease.

Paragraph 12: The method of paragraph 11, wherein the at least one antibody comprises IgG.

Paragraph 13: The method of any preceding paragraph, wherein evaluating the reactivity does not comprise detecting reactivity to OspA/IgG or OspA/IgM.

Paragraph 13.1: The method of any preceding paragraph, wherein evaluating the reactivity does not comprise detecting reactivity to ErpQ/IgG or ErpQ/IgM.

Paragraph 13.2: The method of any preceding paragraph, wherein evaluating the reactivity does not comprise detecting reactivity to BBJ09/IgG or BBJ09/IgM.

Paragraph 13.4: The method of any preceding paragraph, wherein evaluating the reactivity does not comprise detecting reactivity to BB-A68/IgG or BB-A68/IgM.

Paragraph 13.5: The method of any preceding paragraph, wherein evaluating the reactivity does not comprise detecting reactivity to GlpQ/IgG or GlpQ/IgM.

Paragraph 14: The method of paragraph 13-13.4, wherein when a combined fluorescence value is greater or equal to 5955, the biological sample is diagnosed as having Lyme disease.

Paragraph 15: The method of any preceding paragraph, wherein the at least one antibody comprises IgM.

Paragraph 16: The method of any preceding paragraph, wherein evaluating the reactivity comprises assessing the combined fluorescence value of IgM bound to each of the plurality of antigens in the sample.

Paragraph 17: The method of any preceding paragraph, wherein when the combined fluorescence value is greater than or equal to 899, the biological sample is diagnosed as having Lyme disease.

Paragraph 18: The method of any preceding paragraph 7, wherein when the combined fluorescence value of IgM bound to each of the plurality of antigens in the sample is greater than or equal to 899, and the combined fluorescence value of IgG bound to each of the plurality of antigens in the sample is greater or equal to 5955, the biological sample is diagnosed as having Lyme disease.

The embodiments disclosed herein can be further understood by the following numbered paragraphs:

Paragraph 1. A method of detecting the levels of antibodies in a sample of a subject having or suspected of having Lyme Disease, the method comprising:

(i) obtaining a serum, plasma, or blood sample from the subject;

(ii) exposing antibodies in the sample to at least two antigens selected from the group comprising C6, GlpQ, p35, p66, OspC, DbpA, OppA2, ErpQ, OspE, and/or OspC2; and (iii) detecting in said sample the levels of antibodies reactive with each of the at least two antigens by quantifying the amount of antigen-antibody complex formed for each antigen, wherein the amount of antigen-antibody complex is indicative of the level of each respective antibody in said sample.

2. The method of Paragraph 1, comprising detecting the levels of IgG antibodies reactive to C6, GlpQ, p35, p66, OspC, DbpA, OppA2, ErpQ, OspE, and/or OspC2 and levels of IgM antibodies reactive to C6, GlpQ, p35, p66, OspC, DbpA, OppA2, ErpQ, OspE, and/or OspC2 in said sample.

3. The method of Paragraph 1 or 2, wherein the antigens are provided in the form of an antigen array, or attached to a bead.

What is claimed is:

1. A set of reagents to measure the levels of biomarkers in a specimen, wherein the biomarkers are a binding molecules each binding molecule bound to an imaging agent, each binding molecule capable of binding one antigen in a panel of antigens, the panel selected from the group consisting of the following panels and each panel consisting of the specified antigens or measurable fragments thereof:

(a) outer surface protein C2 (OspC2), and an 26-amino acid peptide within the VlsE protein (C6);

(b) C6, glycerophosphodiester phosphodiesterase protein (GlpQ), protein p35 (p35), porin protein p66 or the protein p66 (p66), outer surface protein C (OspC) decorin-binding protein A (DbpA), periplasmic oligopeptide binding protein (OppA2), protein exported repeated protein Q (ErpQ), outer surface protein E (OspE), OspC2;

(c) C6, p35, p66, OspC, DbpA, OppA2, ErpQ, OspE, OspC2;

(d) OspC2, OspC, C6, and p35;

(e) OspC2, OspC, C6, and p66;

(f) OspC2, OspC, C6, and DbpA;

(g) OspC2, OspC, C6, and OppA2;

(h) OspC2, OspC, Co, and ErpQ; and (i) OspC2, OspC, C6, and OspE.

2. The set of reagents of claim 1, wherein the reagents are binding molecules.

3. The set of reagents of claim 2, wherein the binding molecules are antibodies.

4. A test kit comprising the set of reagents of claim 1.

5. A multianalyte panel assay comprising the set of reagents of claim 1.

6. A set of antigens fixed to a plurality of beads to measure the levels of biomarkers in a specimen, wherein the biomarkers are antibodies each antibody bound to an imaging agent, each antibody capable of binding one antigen in a panel of antigens selected from the group consisting of the following panels and each panel consisting of the specified antigens or measurable fragments thereof:

(a) OspC2, and C6;

(b) C6, GlpQ, p35, p66, OspC, DbpA, OppA2, ErpQ, OspE, OspC2;

(c) C6, p35, p66, OspC, DbpA, OppA2, ErpQ, OspE, OspC2;

(d) OspC2, OspC, Co, and p35;

(e) OspC2, OspC, C6, and p66;

(f) OspC2, OspC, C6, and DbpA;

(g) OspC2, OspC, C6, and OppA2;

(h) OspC2, OspC, C6, and ErpQ; and (i) OspC2, OspC, C6, and OspE.

* * * * *